United States Patent
Brosh, Sr. et al.

(10) Patent No.: US 11,078,496 B2
(45) Date of Patent: Aug. 3, 2021

(54) SYSTEM FOR F-BOX HORMONE RECEPTOR REGULATED PROTEIN EXPRESSION IN MAMMALIAN CELLS

(71) Applicants: ICAHN SCHOOL OF MEDICINE AT MOUNT SINAI, New York, NY (US); UNIVERSITY OF WASHINGTON THROUGH ITS CENTER FOR COMMERCIALIZATION, Seattle, WA (US)

(72) Inventors: Ran Brosh, Sr., New York, NY (US); Ihor R. Lemischka, New York, NY (US); Ning Zheng, Shoreline, WA (US)

(73) Assignees: ICAHN SCHOOL OF MEDICINE AT MOUNT SINAI, New York, NY (US); UNIVERSITY OF WASHINGTON THROUGH ITS CENTER FOR COMMERCIALIZATION, Seattle, WA (US)

( * ) Notice: Subject to any disclaimer, the term of this patent is extended or adjusted under 35 U.S.C. 154(b) by 0 days.

(21) Appl. No.: 16/093,436

(22) PCT Filed: Apr. 12, 2017

(86) PCT No.: PCT/US2017/027168
§ 371 (c)(1),
(2) Date: Oct. 12, 2018

(87) PCT Pub. No.: WO2017/180720
PCT Pub. Date: Oct. 19, 2017

(65) Prior Publication Data
US 2019/0316150 A1    Oct. 17, 2019

Related U.S. Application Data

(60) Provisional application No. 62/321,559, filed on Apr. 12, 2016.

(51) Int. Cl.
C07H 21/04 (2006.01)
C12N 15/86 (2006.01)
A61K 48/00 (2006.01)
C12N 7/00 (2006.01)

(52) U.S. Cl.
CPC .......... *C12N 15/86* (2013.01); *A61K 48/0066* (2013.01); *A61K 48/0083* (2013.01); *C12N 7/00* (2013.01); *C12N 2799/02* (2013.01)

(58) Field of Classification Search
CPC ........................... C12N 15/86; A61K 48/0066
See application file for complete search history.

(56) References Cited

U.S. PATENT DOCUMENTS

| | | |
|---|---|---|
| 9,297,017 B2 | 3/2016 | Sheard et al. |
| 2012/0017340 A1 | 1/2012 | Ohlrogge et al. |
| 2012/0142764 A1 | 6/2012 | Seol |
| 2012/0322852 A1 | 12/2012 | Dreyfuss et al. |
| 2013/0227716 A1 | 8/2013 | Sheard et al. |

OTHER PUBLICATIONS

PCT International Search Report and Written Opinion for corresponding PCT/US2017/027168, dated Jul. 17, 2017.
International Preliminary Report on Patentability for corresponding PCT/US2017/027168, dated Oct. 25, 2018.

*Primary Examiner* — Kimberly Chong
(74) *Attorney, Agent, or Firm* — Troutman Pepper Hamilton Sanders LLP (Rochester)

(57) ABSTRACT

The present invention relates to a system for F-box hormone receptor regulated protein expression in mammalian cells. The system includes a silencing nucleic acid molecule comprising a first promoter and an shRNA operably linked to the first promoter, where the shRNA silences expression of a target protein. The system also includes an expression nucleic acid molecule comprising a second promoter, an F-box hormone receptor operably linked to the second promoter, and a nucleic acid molecule encoding a fusion protein comprising a degron fused to the target protein, where the nucleic acid molecule encoding the fusion protein is operably linked to the second promoter. Also disclosed are vectors comprising the system of the present application and methods of use thereof.

22 Claims, 19 Drawing Sheets
Specification includes a Sequence Listing.

A

B

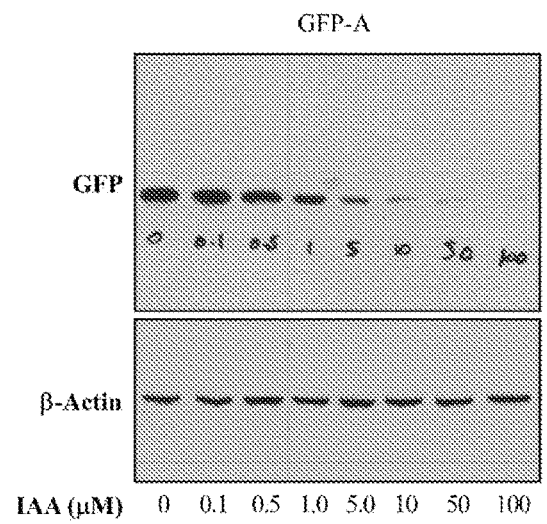
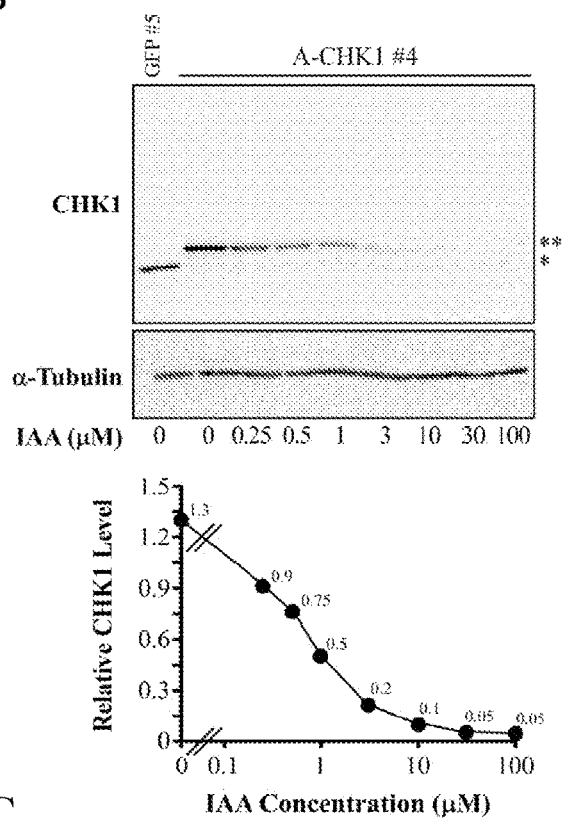
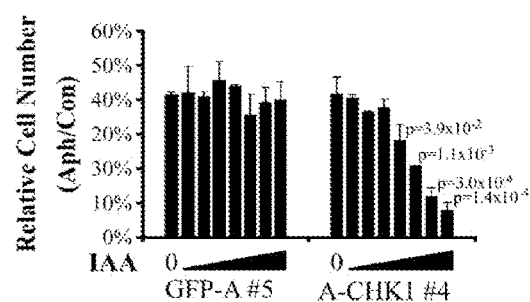
FIGS 8A-AC

A

B

C  D  E

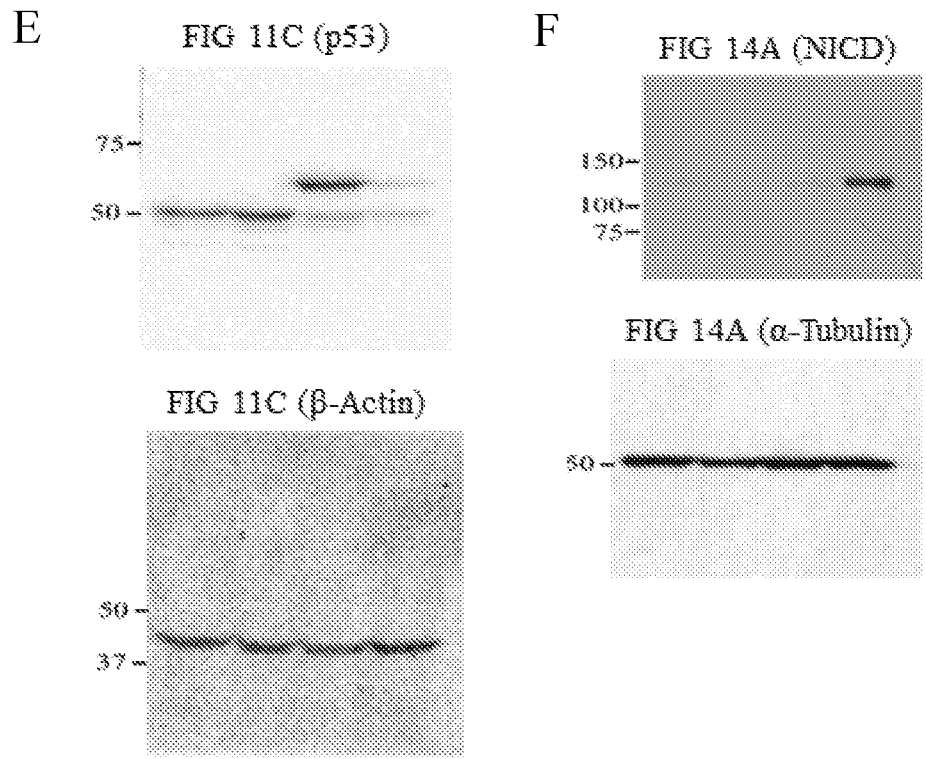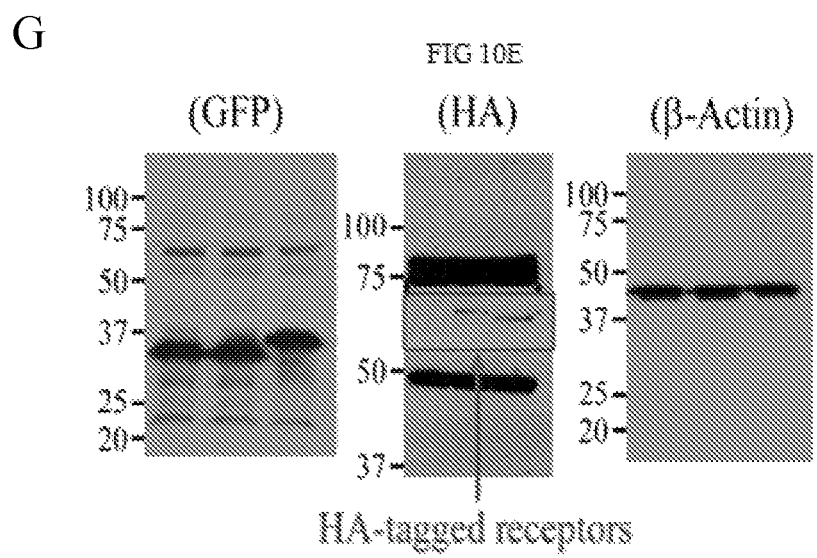
FIGs 15E-15G

H

SYSTEM FOR F-BOX HORMONE RECEPTOR REGULATED PROTEIN EXPRESSION IN MAMMALIAN CELLS

This application is a national stage application under 35 U.S.C. § 371 of PCT Application No. PCT/US2017/027168, filed Apr. 12, 2017, which claims the priority benefit of U.S. Provisional Patent Application Ser. No. 62/321,559, filed Apr. 12, 2016, each of which is hereby incorporated by reference in its entirety.

This invention was made with government support under grant numbers RO1GM078465 and 2RO1CA107134 awarded by the National Institutes of Health. The government has certain rights in the invention.

FIELD OF THE INVENTION

The present invention relates a system for F-box hormone receptor regulated protein expression in mammalian cells.

BACKGROUND OF THE INVENTION

Biologists are increasingly adopting holistic approaches, such as systems biology, to understand life's complexity. Nevertheless, reductionism still remains a primary driving force for scientific progress. Elucidating gene function underlies most biological discoveries and is frequently achieved using loss-of-function analyses. Yet, for mammalian cells in general, and even more so for mammalian stem cells, the biologist's toolbox is limited and primarily includes laborious genomic editing (Kim et al., "Genomic Editing Tools to Model Human Diseases with Isogenic Pluripotent Stem Cells," *Stem Cells Dev.* 23:2673-2686 (2014)), a limited set of often-nonspecific chemical inhibitors and RNA interference (RNAi). Recently developed tools augment experimental flexibility and accuracy (Auslander et al., "From Gene Switches to Mammalian Designer Cells: Present and Future Prospects," *Trends Biotechn.* 31:155-168 (2013) and Lienert et al., "Synthetic Biology in Mammalian Cells: Next Generation Research Tools and Therapeutics," *Nat. Rev. Mol. Cell. Biol.* 15:95-107 (2014)), but are still limited in applicability, reversibility, titratability, rapidity, and multiplicity (Table 1).

TABLE 1

Selected Methods to Regulate Gene Activity in Mammalian Cells.

| Method | Short Description | Relevant Advantages | Relevant Disadvantages |
|---|---|---|---|
| Chemical Inhibitors | Small molecules that inhibit protein activity. | [1] Fast, titratable and reversible. [2] Regulate protein activity. | [1] Limited mainly to enzymes. [2] Low specificity. |
| Genome Editing | Various tools to alter genomic sequences. Mainly used to inactivate or modify genes. Conditional approaches are also available. | [1] Specific. [2] Gene inactivation is complete. [3] Flexible design. | [1] Non-titratable. [2] Usually non-reversible. [3] Laborious. |
| RNAi | Gene silencing by mRNA degradation or translational inhibition. | [1] Simple. [2] Applicable to any gene. | [1] Low specificity (i). [2] Slow (ii). [3] Non-conditional. |
| Conditional RNAi | Vectors containing a conditional promoter (usually Tet-regulated) driving shRNA expression. | [1] Applicable to any gene. [2] Conditional. | [1] Low specificity (i). [2] Slow (ii). [3] Requires rtTA/tTA (iii). |
| RNAi + Tet-Ind. CDS Rescue3 | Lentiviral vector containing continuously-expressed shRNA and Tet-inducible CDS that rescues the phenotype exerted by the shRNA. | [1] Specific (iv). [2] Conditional, reversible. [3] Somewhat-titratable (v). [4] Rescue system (vi). | [1] Slow response (days). [2] Requires rtTA/tTA (iii). |
| pAID (Auxin Induced Degradation)* (See also comment xi) | Plasmid harboring TIR1 (auxin receptor), followed by IRES and degron to which a POI is fused. The degron-fused POI is ubiquitinated and degraded following auxin treatment. | [1] Acts on protein level. [2] Fast. [3] Simple-to-use. [4] Effective, titratable and reversible. | [1] No control over endogenous genes (vii). [2] Very large degron (viii). [3] Non-viral plasmid (ix). [4] CMV promoter (x). [5] No specialized selectable marker. [6] Two plasmids for N/C - terminus fusions. |
| Shield-1-Stabilized FKBP-POI6 | FKBP-POI6 A POI is destabilized by fusion to FKBP12 variant. A small molecule (Shield-1) restabilizes the POI. | [1] Acts on protein level. [2] Effective, titratable and reversible degradation. | [1] No control over endogenous genes (xii). [2] Large degron (107-AAs). [3] Relatively slow (several hours). |
| pRAIDRS and pJAZ | Each lentiviral vector is an independent rescue system containing continuously-expressed shRNA and an shRNA-immune hormone-degradable POI that rescues the phenotype exerted by the shRNA | [1] Acts on protein level. [2] Rescue system (vi). [3] Specific (iv). [4] Fast. [5] Titratable and reversible. [6] Short and stable degrons (xiii). [7] Lentiviral (effective delivery). [8] Independent (xiv). [9] In-frame selectable marker (xv). [10] Simple-to-use. | [1] Coronatine is expensive. [2] Efficiency depends on protein localization (xvi). [3] pJAZ ineffective in mESCs (xvii). |

TABLE 1-continued

Selected Methods to Regulate Gene Activity in Mammalian Cells.

| Method | Short Description | Relevant Advantages | Relevant Disadvantages |
| --- | --- | --- | --- |
| | | [11] One plasmid for N/C-terminal fusions. [12] Combinatorial. | |

*Nishimura et al., "An Auxin-Based Degron System for the Rapid Depletion of Proteins in Nonplant Cells," Nat. Methods 6: 917-922 (2009).
i. RNAi can affect hundreds of genes. To overcome this, different RNAi sequences targeting the same gene can be used to substantiate causality between silencing and observed phenotypes (Cullen et al., "Enhancing and Confirming the Specificity of RNAi Experiments," Nat. Methods 3: 677-681 (2006)).
ii. Effective gene silencing is usually obtained within 2-3 days (Brummelkamp et al., "A System for Stable Expression of Short Interfering RNAs in Mammalian Cells," Science 296: 550-553 (2002) and van de Wetering et al., "Specific Inhibition of Gene Expression Using a Stably Integrated, Inducible Small Interfering-RNA vector," EMBO Reports 4: 609-615 (2003)). With inducible systems, silencing can be obtained within 1-2 days and reversal of the effect usually takes longer.
iii. Tet-regulated systems require rtTA or tTA, which usually necessitates the delivery of a second plasmid encoding one of these proteins, or a specialized cell type that stably expresses it.
iv. If an RNAi-dependent phenotype is reversed by the CDS of the silenced gene, it is unlikely that the phenotype stemmed from an RNAi off-target effect (Cullen et al., "Enhancing and Confirming the Specificity of RNAi Experiments." Nat. Methods 3: 677-681 (2006)).
v. Tet-induced expression is usually hard to accurately titrate.
vi. A rescue (or genetic complementation) system enables the replacement of an endogenous gene with an exogenous version that can be regulated externally. Represents a type of a molecular switch.
vii. pAID allows expression of auxin-degradable proteins. However, it does not contain a component, such as an shRNA, that inactivates an endogenous gene and allows its replacement by the auxin-degradable protein.
viii. The AID degron used in pAID is the full-length A. thaliana IAA17 transcription factor. As a degron, it suffers from several disadvantages, including its large size (228-amino acids), its ability to confer nuclear localization to the fused POI (data 14 not shown) and, possibly, a tendency to be spontaneously cleaved-off from the POI. Notably, the observation of spontaneous cleavage of GFP-AID$^{228}$ in pRAIDRS-infected 293T cells (FIGS. 2A-2F) was not reported by other groups, who successfully used GFP-AID$^{228}$.
ix. Non-viral plasmids are hard to deliver into some types of mammalian cells, including hard-to-transfect cells (such as fibroblasts, ESCs, and many primary cell types) and slow-proliferating cells. Additionally, genomic integration of nonviral plasmids is an extremely rare event in many cell types.
x. The CMV promoter undergoes silencing in certain mammalian stem cells, such as human ESCs Xia et al., "Transgenes Delivered by Lentiviral Vector are Suppressed in Human Embryonic Stem Cells in a Promoter-Dependent Manner." Stem Cells and Development 16: 167-176 (2007) and Norrman et al., "Quantitative Comparison of Constitutive Promoters in Human ES Cells," PLoS ONE 5: e12413 (2010).
xi. Auxin-dependent degradation was utilized successfully in several studies of mammalian cells (Han et al.,, "Catalytic Assembly of the Mitotic Checkpoint Inhibitor BubR1-Cdc20 by a Mad2-Induced Functional Switch in Cdc20," Mol. Cell 51: 92-104 (2013); Holland et al., "Inducible, Reversible System for the Rapid and Complete Degradation of Proteins in Mammalian Cells," Proc. Natl. Acad. Sci. USA 109: E3350-3357 (2012); Lambrus et al., "p53 Protects Against Genome Instability Following Centriole Duplication Failure," J. Cell Biol. 210: 63-77 (2015); and Rodriguez-Bravo et al., "Nuclear Pores Protect Genome Integrity by Assembling a Premitotic and Mad1- Dependent Anaphase Inhibitor," Cell 156: 1017-1031 (2014)), albeit not in stem cells. Nevertheless, to engineer auxin-degradable proteins in mammalian cells the authors had to use several consecutive and rather-laborious steps. For example, Holland et al., "Inducible, Reversible System for the Rapid and Complete Degradation of Proteins in Mammalian Cells," Proc. Natl. Acad. Sci. USA 109: E3350-3357 (2012) as well as Han et al., "Catalytic Assembly of the Mitotic Checkpoint Inhibitor BubR1-Cdc20 by a Mad2-Induced Functional Switch in Cdc20," Mol. Cell 51: 92-104 (2013) first generated cell lines that overexpress the TIR1 receptor, then overexpressed an AID-fused POI, and finally transiently knocked-down the gene encoding for the endogenous POI. Similarly, Lambrus et al., "p53 Protects Against Genome Instability Following Centriole Duplication Failure," J. Cell Biol. 210: 63-77 (2015) sequentially targeted the AID degron to the two endogenous alleles of the POI, and then overexpressed TIR1.
xii. The system is limited to exogenously-expressed proteins, unless genome-editing is used to fuse the destabilizing FKBP domain to both alleles of an endogenous gene, or a form of rescue system is established by inactivating the endogenous gene and replacing it with an FKBP-fused version.
xiii. pRAIDRS and pJAZ harbor relatively short degrons (47-amino acids and 33-amino acids, respectively). Shorter degrons reduce the likelihood of steric interference with the POI's function, and supposedly, have less non-degron functions (such as interactions with additional proteins or DNA or effect on protein localization). Additionally, the shorter AID degron seem to suffer less from spontaneous cleavage from the POI compared with the full-length AID$^{228}$, at least in our experimental settings (FIGS. 2C-2D).
xiv. As opposed to the RNAi + Tet-Inducible CDS Rescue System, pRAIDRS and pJAZ contain all the necessary genetic elements to silence an endogenous gene and replace it by a hormone-degradable POI. They can be used in nonspecialized cells without additional components.
xv. In pRAIDRS and pJAZ the selectable markers (either PuroR or BSD genes) are cloned in-frame with the hormone receptor and degron-POI. Following translation and cleavage at the P2A peptides, the selectable marker is released and can render cells resistant to its corresponding drug. The expression of all components from a single promoter and as a single pre-processed protein reduces the likelihood that in drug-resistant cells will silencing or mutation the hormone receptor or degron-POI will occur.
xvi. Both pRAIDRS and pJAZ show increased efficiency with nuclear POIs compared to cytoplasmic POIs.
xvii. Coronatine-dependent degradation in mouse embryonic stem cells is ineffective (usually 50-80%, compared with >90% in other mouse cell types and all tested human cell types).

Thus, simple tools for rapid and multiple gene perturbation will facilitate the elucidation of gene functions and molecular networks.

Manipulation of protein levels represents a relatively new loss-of-function approach. To this end, harnessing the plant hormone-induced degradation pathways is particularly attractive due to its efficiency and specificity. The plant hormones auxin (indole-3-acetic acid, "IAA") and jasmonate-isoleucine (jasmonic acid-Ile, "JA-Ile") bind the intracellular F-Box proteins transport inhibitor response 1 ("TIR1") and coronatine insensitive 1 ("COI1"), respectively, and promote their association with target proteins containing specific degron motifs. TIR1 and COI1, via their F-box domains, assemble into the SCF (SKP1, CUL1 and F-box) E3 ubiquitin-ligase complex, which together with an E2 ubiquitin-conjugating enzyme, catalyses the polyubiquitination and subsequent proteasomal degradation of degron-containing proteins (Tan et al., "Mechanism of Auxin Perception by the TIR1 Ubiquitin Ligase," Nature 446:640-645 (2007); Sheard et al., "Jasmonate Perception by Inositol-phosphate-potentiated COI1-JAZ Co-Receptor," Nature 468:400-405 (2010); Dharmasiri et al., "The F-Box Protein TIR1 is an Auxin Receptor," Nature 435:441-445 (2005); Kepinski et al., "The Arabidopsis F-Box Protein TIR1 is an Auxin Receptor," Nature 435:446-451 (2005); Thines et al., "JAZ Repressor Proteins are Targets of the SCF(COI1) Complex During Jasmonate Signalling," Nature 448:661-665 (2007); and Chini et al., "The JAZ Family of Repressors is the Missing Link in Jasmonate Signalling," Nature 448:666-671 (2007)). Auxin-bound TIR1 targets proteins containing auxin-induced degradation ("AID") degrons, while JA-Ile-bound COI1 targets proteins containing JAZ degrons (FIG. 1A). Nishimura et al., "An Auxin-based Degron System for the Rapid Depletion of Proteins in Nonplant Cells," Nat. Methods 6:917-922 (2009) developed a system enabling conditional protein regulation by adapting the auxin-induced degradation pathway to non-plant cells. They reported that ectopic TIR1 can mediate auxin-dependent degradation of AID-fused proteins and demonstrated the system's feasibility with a simple plasmid (pAID) harboring a cytomegalovirus promoter-driven polycistronic mRNA encoding TIR1 and a plant protein carrying the AID degron. Fusing a protein-of-interest ("POI") to the degron enabled the degradation of the degron-fused POI following auxin treatment (Nishimura et al., "An Auxin-based Degron System for the Rapid Depletion of Proteins in Nonplant Cells," Nat. Methods 6:917-922 (2009)). Despite its simplicity, pAID has major limitations in terms of applicability to mammalian cells. These include a viral promoter prone to silencing in embryonic stem cells ("ESCs") (Norrman et al., "Quantitative Comparison of Constitutive Promoters in Human ES Cells," *PLoS ONE* 5:e12413 (2010) and Xia et al., "Transgenes Delivered by Lentiviral Vector are Suppressed in Human Embryonic Stem Cells in a Promoter-dependent Manner," *Stem Cells Dev.* 16:167-176 (2007)), a lack of a designated selectable marker, the inability to suppress endogenous genes and a large degron (228 amino acids) liable to interfere with the POI's function. For these and other reasons (Table 1), this technology has been primarily applied to yeast, where endogenous genes are easily disrupted and pAID-carrying clones are readily isolated. Of note, although auxin-dependent degradation was previously used to study mammalian cells, its implementation required multiple consecutive genetic manipulations and was mainly confined to cancer cell lines (Han et al., "Catalytic Assembly of the Mitotic Checkpoint Inhibitor BubR1-Cdc20 by a Mad2-Induced Functional Switch in Cdc20," *Mol. Cell* 51:92-104 (2013); Holland et al., "Inducible, Reversible System for the Rapid and Complete Degradation of Proteins in Mammalian Cells," *Proc. Natl. Acad. Sci. USA* 109:E3350-3357 (2012); Rodriguez-Bravo et al., "Nuclear Pores Protect Genome Integrity by Assembling a Premitotic and Mad1-dependent Anaphase Inhibitor," *Cell* 156:1017-1031 (2014); and Lambrus et al., "p53 Protects Against Genome Instability Following Centriole Duplication Failure," *J. Cell Biol.* 210:63-77 (2015)). In recent times, auxin-dependent degradation was also harnessed in vivo to study *Caenorhabditis elegans* (Zhang et al., "The Auxin-Inducible Degradation (AID) System Enables Versatile Conditional Protein Depletion in *C. elegans*," *Development* 142:4374-4384 (2015)).

Mammalian ESCs have gained much interest as a model for developmental biology and a therapeutic avenue. ESCs are unique in their unlimited self-renewal and pluripotency, a state maintained by a transcription factor network revolving around SOX2, OCT4 (POU5F1) and NANOG (Macarthur et al., "Systems Biology of Stem Cell Fate and Cellular Reprogramming," *Nat Rev Mol Cell Biol* 10:672-681 (2009)). Combining loss-of-function and genetic complementation (rescue) strategies, the ESC self-renewal network was broadened and characterized (Macarthur et al., "Systems Biology of Stem Cell Fate and Cellular Reprogramming," *Nat Rev Mol Cell Biol* 10:672-681 (2009); Gingold et al., "A Genome-wide RNAi Screen Identifies Opposing Functions of Snai1 and Snai2 on the Nanog Dependency in Reprogramming," *Mol Cell* 56:140-152 (2014); Lee et al., "Regulation of Embryonic and Induced Pluripotency by Aurora Kinase-p53 Signaling," *Cell Stem Cell* 11:179-194 (2012); Ang et al., "Wdr5 Mediates Self-Renewal and Reprogramming Via the Embryonic Stem Cell Core Transcriptional Network," *Cell* 145:183-197 (2011); and Ivanova et al., "Dissecting Self-Renewal in Stem Cells with RNA Interference," *Nature* 442:533-538 (2006)). There is a need for an improved experimental system that upgrades the stem cell biologist's toolbox and facilitates faster, tighter and combinatorial dissection of gene and protein function.

The present invention is directed to overcoming the above-noted deficiencies in the art.

SUMMARY OF THE INVENTION

The present invention relates to a system for F-box hormone receptor regulated protein expression. The system includes a silencing nucleic acid molecule comprising a first promoter and an shRNA operably linked to the first promoter, where the shRNA silences expression of a target protein. The system also includes an expression nucleic acid molecule comprising a second promoter, an F-box hormone receptor operably linked to the second promoter, and a nucleic acid molecule encoding a fusion protein comprising a degron fused to the target protein, where the nucleic acid molecule encoding the fusion protein is operably linked to the second promoter.

The present invention also relates to a vector comprising the system of the present application, where the silencing nucleic acid molecule is coupled directly or indirectly to the expression nucleic acid molecule.

The present invention further describes a method for F-box hormone receptor regulated protein degradation in a mammalian host cell. This method involves providing a mammalian host cell; introducing the system of the present application into the mammalian host cell to produce a transgenic mammalian host cell; culturing said transgenic mammalian host cell under conditions that result in (i) silencing expression of the target protein and (ii) expression of the fusion protein; and contacting said transgenic mammalian host cell with a molecule that binds the F-box hormone receptor so that said fusion protein undergoes degradation.

The present invention also describes a method for F-box hormone receptor regulated target protein degradation in a mammalian host cell. This method involves providing a mammalian host cell and infecting, into the mammalian host cell, a first lentiviral vector comprising (i) a first silencing nucleic acid molecule comprising a primary first promoter and a first shRNA operably linked to the primary first promoter, where the first shRNA silences expression of a first target protein and (ii) a first expression nucleic acid molecule comprising a primary second promoter, a Transport Inhibitor Response 1 ("TIR1") receptor operably linked to the primary second promoter, and a nucleic acid molecule encoding a first fusion protein comprising an auxin-induced degradation ("AID") degron fused to a first target protein, where the nucleic acid molecule encoding the first fusion protein is operably linked to the primary second promoter. The method further involves infecting, into the mammalian host cell, a second lentiviral vector comprising (i) a second silencing nucleic acid molecule comprising a secondary first promoter and a second shRNA operably linked to the secondary first promoter, where the second shRNA silences expression of a second target protein and (ii) a second expression nucleic acid molecule comprising a secondary second promoter, a Coronatine Insensitive 1 ("COI1") receptor operably linked to the secondary second promoter, and a nucleic acid molecule encoding a second fusion protein comprising a JAZ degron fused to a second target protein, where the nucleic acid molecule encoding the second fusion protein is operably linked to the secondary second promoter. The method further involves culturing the infected mammalian host cell under conditions that result in (i) silencing expression of the first and second target proteins and (ii) expression of the first and second fusion proteins; contacting the infected mammalian host cell with a molecule that binds the TIR1 receptor so that said first fusion protein undergoes degradation; and contacting the infected mammalian host cell with a molecule that binds the COI1 receptor so that said second fusion protein undergoes degradation.

The examples of the present application describe a mammalian dual-protein rescue system that harnesses the auxin and JA-Ile pathways, and may be specifically tailored to ESCs. For each hormone, a lentiviral vector harboring a short hairpin RNA ("shRNA"), a hormone receptor, a short degron and a selectable marker was engineered. Using a two-step cloning protocol, each vector is easily modified to contain the desired shRNA and degron-fused POI, which enables silencing of a gene-of-interest and its replacement by a POI whose degradation is induced by the appropriate hormone. The combination of these two vectors offers simultaneous control over two proteins in the same cell. By applying this system to study key ESC decision-making proteins, such as NANOG, CHK1, p53 and NOTCH1, the system's potential to facilitate experimental designs that were previously unfeasible or overcomplicated are demonstrated.

BRIEF DESCRIPTION OF THE DRAWINGS

FIG. 1A is a schematic illustration of plant hormone-induced protein degradation pathways. The plant SCF E3 ubiquitin ligase complex comprises SKP1, CUL1, and an F-box hormone receptor. On binding its cognate hormone, the receptor recruits the SCF complex to a target protein containing a degron motif. A recruited E2 ubiquitin-conjugating enzyme ubiquitinates the target, leading to its rapid proteasomal degradation. Hormone ("H"); ubiquitin ("Ub"). FIG. 1B, upper panel is a schematic representation of the pRAIDRS and pJAZ vector structure. FIG. 1B, bottom, shows pre- and post-P2A-mediated processing of the translated components. The two-headed arrow indicates that the degron can be fused to either terminus of the POI. Ampicillin resistance β-lactamase ("AmpR"); long-terminal repeat ("LTR"); multiple cloning site ("MCS"); protein-of-interest ("POI"); Psi packaging signal ("Psi"); Rev response element ("RRE"). See also FIGS. 2A-2F.

FIG. 2A is a graph showing Green Fluorescent Protein ("GFP") expression of cells infected with lentiviral vectors using pRAIDRS harboring either a PGK-1 or an EF1α promoter and GFP-AID$^{47}$ into CCE and R1 mESCs or H9 hESCs. Cells were selected, treated with 0.01% EtOH ("Con") or 50 μM auxin ("IAA") and analyzed for GFP fluorescence by flow cytometry. For each cell type, values were normalized to the "pPGK-1, Con" sample. Data represent averages and standard deviation of 2 biological replicates. FIG. 2B is a sequence alignment showing a conserved region among three *A. thaliana* auxin-degradable proteins (AtIAA14, NP_193191 (SEQ ID NO: 1); AtIAA7, NP_188945 (SEQ ID NO: 2); AtIAA17, NP_171921 (SEQ ID NO: 3)) (Villalobos et al, "A Combinatoria TIR1/AFB-Aux/IAA Co-Receptor System for Differential Sensing of Auxin," *Nat. Chem. Biol.* 8:477-485 (2012), which is hereby incorporated by reference in its entirety) and three versions of AtIAA17 that were tested as degrons in pRAIDRS. Conserved residues are highlighted in red. Superscript numbers in degron names indicate length in amino acids. FIG. 2C is a graph showing auxin-induced degradation mediated by different AID degrons. HEK-293T cells were infected with pRAIDRS vectors harboring a GFP fused to degrons of different sizes. Cells were treated with increasing concentrations of IAA and analyzed 24 hours later (left panel) or with 500 μM IAA for the indicated time periods (right panel). GFP fluorescence was analyzed by flow cytometry. Data series are color-coded as in FIG. 2B. Experiment was conducted twice and representative results are displayed. FIG. 3D shows a western blot analysis of GFP in pRAIDRS-infected HEK-293T cells. Untreated cells are expressing GFP fused to either the full-length AtIAA17 ("AID$^{228}$") or to AID$^{47}$. The bands corresponding to GFP-AID$^{228}$ and GFP-AID$^{47}$ are marked with a single asterisk at an expected molecular weight of 58 and 36 kDa, respectively. An additional band (two asterisks) corresponds to cleaved (unfused) GFP protein with the expected molecular weight of 27 kDa. Experiment was conducted 2 times and representative results are displayed. Note the complete absence of cleaved GFP in the right lane, indicating that this spontaneous cleavage occurs only with AID$^{228}$. This phenomenon can explain the biphasic kinetics of GFP-AID$^{228}$ degradation (FIG. 2B) whereas the fused GFP is rapidly degraded, while the unfused is insensitive to auxin. FIG. 2E is a graph showing the effect of nuclear localization on auxin-induced degradation of GFP-AID$^{47}$. HEK-293T cells were infected with pRAIDRS containing either GFP-AID$^{47}$ or NLS-GFP-AID$^{47}$. Cells were treated with increasing concentrations of IAA and analyzed after 24 hours (left panel), or with 50 μM IAA for the indicated time periods (right panel). GFP fluorescence was analyzed by flow cytometry. The experiment was conducted 3 times, and representative results are displayed. FIG. 2F shows GFP and DAPI microscopic images of HEK-293T cells infected with pRAIDRS containing either GFP-AID$^{47}$ or NLS-GFP-AID$^{47}$.

FIGS. 3A-3D illustrate an auxin-degradable NANOG rescue system in mESCs. CCE mESCs were infected with pRAIDRS AID$^{47}$-NANOG (A-NANOG) or GFP-AID$^{47}$ ("GFP-A") and selected clones with ESC morphology were analyzed for the effect of auxin ("IAA") treatment. FIG. 3A is a western blot analysis depicting endogenous NANOG (*) and A-NANOG (**) in parental mESCs, and in the indicated clones. β-Actin serves as a loading control. Experiment was repeated three times and a representative blot is presented. FIG. 3B are images of mESC clones plated at low density, grown in the presence of ethanol ("Con") or auxin ("IAA") for 3-4 days and assayed for AP activity. GFP-A mESCs reached the desired confluency a day earlier and therefore the images were taken on different days. FIG. 3C are bright-field images showing representative morphology of A-NANOG mESCs following 3 days of ethanol ("Con") or auxin ("IAA") treatment (upper part) and merged bright-field and GFP fluorescence images of ethanol or auxin-treated GFP-A mESCs (lower part). Scale bars, 100 μm. FIG. 3D shows a heatmap of mESC clones treated with auxin for the indicated number of days. All cells were subjected to the same concentration of ethanol for the duration of experiment. Quantitative real-time PCR analysis was performed for selected self-renewal and differentiation markers, and normalized expression levels are represented as a heatmap. For FIGS. 3B-3D, the differentiation experiment was repeated two times and representative results are displayed. See also FIGS. 4A-4F and FIG. 15.

In FIG. 4A, A-NANOG #2 mESCs were treated with 50 μM auxin ("IAA") for the indicated time periods. Western blot analysis demonstrates complete depletion of ANANOG following 30 minutes of auxin treatment. Endogenous NANOG and exogenous A-NANOG are marked by * and **, respectively. The experiment was conducted 3, times and representative results are displayed. FIG. 4B shows selected mRNA expression patterns from the heatmap in FIG. 3D displayed as bar charts. Error bars represent standard deviation of three technical replicates. FIGS. 4C-4D illustrate shRNA-mediated knockdown of NANOG in CCE mESCs. Cells were infected with pLKO.1-Puro-IRESmCherry harboring either a Luciferase shRNA ("sh-Con") or a Nanog shRNA ("sh-Nanog"). Two days post infection cells were selected with 1 μg/ml Puromycin for the indicated number of days. On the third day of selection, cells were collected for the first QRT-PCR analysis time point and the rest of the cells were replated for the following time points. FIG. 4C is a western blot analysis of cells collected on the fifth day of selection. FIG. 4D shows QRT-PCR data presented as a heatmap. Experiment was conducted twice and representative results are displayed. In FIG. 4E, mESCs were infected with either pRAIDRS GFP-AID$^{47}$ ("GFP-A"), pRAIDRS AID$^{47}$-NANOG ("A-NANOG") or pRAIDRS OsJAZ$^{33}$-NANOG ("J-NANOG"), which harbors a Nanog shRNA and a Nanog coding sequence fused to the OsJAZ$^{33}$ degron. In the latter cells, endogenous Nanog is replaced by an exogenous Nanog that does not contain an AID degron and, therefore, should be auxin resistant. A western blot analysis depicts endogenous NANOG (*) and exogenous degron-fused NANOG (**) in a pool of GFP-A mESCs and clones of ANANOG and J-NANOG mESCs. Experiment was conducted once. FIG. 4F are images of GFP-A (pool) and clones of A-NANOG and JNANOG mESCs were plated at low density, grown in the presence of EtOH ("Con") or auxin ("IAA") for 4 days and assayed for alkaline phosphatase activity. Low magnification pictures were taken using a bright-field microscope. Note that only A-NANOG mESCs demonstrated reduction in AP-positive colony number upon auxin treatment.

FIG. 5A is a western blot analysis depicting endogenous CHK1 (*) and AID$^{47}$-CHK1 (A-CHK1, **) in four selected clones and in parental non-infected mESCs. P3-Actin serves as a loading control. Experiment was repeated three times for clones #1 and #2, and a representative blot is presented. In FIG. 5B, A-CHK1 #2 mESCs were treated with ethanol ("Con") or auxin ("IAA") for 1 day. Cells were then treated with the indicated concentrations of aphidicolin ("Aph"). Equal concentrations of DMSO were applied to all conditions. The next day, cells were stained with crystal violet and plates were scanned. The experiment was repeated three times, and a representative result is displayed. In FIG. 5C, mESC clones were pretreated with 1 mM aphidicolin for 1 day and were then treated with auxin for the indicated time periods. Left panel: mitotic index was calculated as the percentage of H3$^{pS10}$-positive cells with 4N DNA content, measured by flow cytometry. Right panel: dot plots for A-CHK1 #2 mESCs treated with auxin for 0 or 45 minutes. Mitotic cells are gated. FIG. 5D show bright-field microscope images of cells treated as in FIG. 5C. Images show synchronous cell rounding, a feature of late mitotic cells, 2 hours following auxin treatment in aphidicolin-treated A-CHK1 #2 cells. FIG. 5E is a western blot analysis of cells treated as in FIG. 5C. Tyr15 phosphorylation of CDK1 ("CDK1pY$^{15}$") was detected using a phospho-specific antibody. β-Actin serves as a loading control. FIG. 5F shows quantitative real-time PCR analysis of Fas mRNA in cells treated as described in FIG. 5C. Error bars represent standard deviation of three technical replicates. For FIGS. 5C-5F, kinetic experiments was repeated three times and representative results are displayed. See also FIGS. 6A-6E, 7A-7G, 8A-8C, and 15.

FIG. 6A show images of cells assayed for alkaline phosphatase activity. CCE mESCs were infected with pRAIDRS GFP-A or A-CHK1 and selected in the presence of EtOH ("Con") or auxin ("IAA"). After colonies emerged, cells were assayed for alkaline phosphatase activity. Left, low magnification scans. Right, bright-field microscope images. Scale bars, 100 μm. The experiment was conducted 3 times, and representative results are displayed.

FIG. 6B are graphs showing populations doubling, following selection, of the indicated clones cultured in the presence of 0.01% EtOH (solid lines) or 50 μM IAA (dashed lines). Cells were counted and replated every 3-4 days and population doublings were calculated as $Log_2$ (cell output/cell input). Experiment was conducted once for these clones. In FIG. 6C, CCE A-CHK1 clone #2 cells were subjected to a competition assay (Lee et al., "Combining Competition Assays with Genetic Complementation Strategies to Dissect Mouse Embryonic Stem Cell Self-Renewal and Pluripotency," Nat. Protoc. 7:729-748 (2012), which is hereby incorporated by reference in its entieritey.) Cells were labeled with mCherry fluorescence protein and co-cultured with control GFP-A CCE cells in the presence of 0.01% EtOH or 50 μM IAA. Cells were collected every 2-3 days and assayed for GFP and mCherry fluorescence by flow cytometry. The percentage of A-CHK1 cells was calculated for each time point and the values for the auxin-treated cells were normalized to those of EtOH-treated cells. An average growth rate decrease of 8% per day was calculated for auxin-treated A-CHK1 cells compared to the EtOH-treated controls. For comparison, a similar assay performed by Ivanova et al. reported drastic reduction in cell proportion following knock-down of genes involved in mESC self-renewal (Ivanova et al., "Dissecting Self-Renewal in Stem Cells with RNA Interference," Nature 442: 533-538 (2006), which is hereby incorporated by reference in its entirety). The experiment was conducted twice, and representative results are displayed. In FIG. 6D, the indicated clones were treated with 0.01% EtOH (orange histograms) or 50 μM IAA (blue histograms) for 2 days and analyzed for cell surface pluripotency marker SSEA-1 expression by flow cytometry. Red histogram, isotype control. Numbers indicate percentages of SSEA-1 positive cells and are color-coded similarly to the histograms. Experiment was conducted once. In FIG. 6E, the indicated clones were treated with 0.01% EtOH or 50 μM auxin ("IAA") for 3 days and analyzed for the expression of self-renewal and differentiation markers by QRT-PCR. Bars represent $Log_2$ (fold change[IAA/EtOH]). Error bars represent standard deviation of 3 technical replicates. Auxin-induced differentiation experiment was performed 3 times and representative results are displayed. On the right, data from retinoic acid ("RA", 5 μM, 3 days) and EtOH ("Con", 0.05%, 3 days) treated mESCs serve as a positive control for mESC differentiation transcriptional alterations.

FIG. 7A are images of cell stained with crystal violet. The indicated clones were pre-treated with 0.01% EtOH or 50 μM auxin ("IAA") for one day. Cells were then treated with the indicated concentrations of aphidicolin ("Aph"). Equal concentrations of DMSO were applied in all conditions. The next day, cells were stained with crystal violet and plates were scanned. FIG. 7B shows cell stained with crystal violet. The indicated clones were pre-treated with 0.01% EtOH or 50 μM auxin ("IAA") for one day. Cells were then treated with 1 μM aphidicolin ("Aph") or 0.01% DMSO for 12 hours, trypsinized, resuspended in fresh media and 5% of the total volume was replated. Replated cells were grown in the absence of aphidicolin for two days, stained with crystal violet and microscope images were acquired. Scale bars, 200 μm. Experiment was conducted 2 times and representative results are displayed. In FIG. 7C, the indicated mESC clones were pre-treated with EtOH or auxin (IAA) for one day.

Cells were then treated with 1 μM 5 aphidicolin ("Aph") or 0.001% DMSO for 12 hours and analyzed for DNA content using propidium iodide ("PI"). The percentage of cells with less than 2N DNA content (% SubG1 cells) was plotted. The experiment was repeated 2 times, and representative results are displayed. FIGS. 7D-7E show that CHK1 depletion in aphidicolin-treated cells leads to induction of p53 transcriptional targets and differentiation markers. The indicated mESC clones were pre-treated with 0.01% EtOH or 50 μM IAA for one day and were then treated with 1 μM aphidicolin ("Aph") or 0.01% DMSO for 12 or 24 hours. QRT-PCR analysis was performed for selected markers, including p53 target genes (Fas, Mdm2, p21, Noxa), endodermal differentiation markers (Gata4, Sox17), mesodermal differentiation markers (T, Mixl1), ectodermal differentiation marker (Nestin) and trophectodermal differentiation markers (Cdx2, Hand1). FIG. 7D shows a heat map of normalized average expression levels. FIG. 7E are bar charts showing the expression levels of selected genes. Experiment was repeated 3 times and representative results are displayed. FIG. 7F is a graph of the apoptotic index of the cells. The indicated clones were pre-treated with 1 μM aphidicolin for one day and were then treated with EtOH ("Con") or auxin ("IAA") for the indicated time periods. Apoptotic index was calculated as the percentage of Annexin V-positive, 7-AAD-negative cells. Experiment was repeated twice and representative results are displayed. In FIG. 7G, cells were treated as described above. Bright-field microscope images showing synchronous cell rounding, a feature of late mitotic cells, two hours following auxin treatment in aphidicolin-treated ACHK1#2 cells, but not in GFP-A #5 cells. Experiment was performed more than 3 times and representative results are displayed.

FIGS. 8A-8C show that pRAIDRS Enables Titratable Regulation of Protein Level. FIG. 8A shows a western blot image and chart of the protein levels of HEK-293T cells infected with pRAIDRS GFP-AID$^{47}$ and treated with the indicated concentrations of IAA for one day. 13-Actin was used as a loading control. Protein levels were quantified and normalized levels were presented in the chart shown below the western blot image. Experiment was performed 3 times and representative results are displayed. FIG. 8B shows a western blot image and chart of the protein levels of CCE mESCs clones GFP-A #5 and A-CHK1 #4 treated with the indicated concentrations of IAA for one day. α-Tubulin was used as a loading control. Protein levels were quantified and relative levels of total CHK1 (calculated as the level of endogenous CHK1 (*) plus the level of A-CHK1(**) divided by the level of α-Tubulin and normalized so that endogenous CHK1 in GFP #5 was set to 1) are plotted (bottom). In FIG. 8C, cells were treated with increasing concentrations of auxin (as in FIG. 8B). The next day, media was supplemented with 1 μM aphidicolin ("Aph") or 0.01% DMSO ("Con") for 24 hours. Cells were stained with crystal violet, washed, and the remaining crystal violet was extracted with acetic acid and quantified using a spectrophotometer at 590 nm. Relative cell number was calculated as the ratios of Aph/Con-treated samples. Error bars represent standard deviation of 3 technical replicates. Statistical significance was calculated using a non-paired t-test for each IAA concentration compared with concentration 0 μM and statistically significant p-values (<0.05) are proved next to their corresponding bars. Experiment was performed twice and representative results are displayed.

FIG. 9A is a western blot analysis of p53 and p21 of cells washed three times and incubated with fresh media in the absence of auxin for the indicated time periods. β-Actin serves as a loading control. FIG. 9B is a quantification of protein levels presented in FIG. 9A. Values were normalized such that the level of each protein at the 24-hour time point was set to 100%. FIG. 9C shows quantitative real-time PCR analysis of the p53 target genes p21 ("CDKN1A") and MDM2. Cells were treated as described above prior to analysis. Error bars represent standard deviation of three technical replicates. The experiment was repeated three times, and representative results are displayed. FIG. 9D shows the populations doublings of cells grown in the presence of ethanol ("Con") or auxin ("IAA") and counted every day for 4 days. Media was replaced daily. Population doublings ("PDLs") were calculated as $Log_2$ (cell output/cell input). Error bars represent standard deviation of three technical replicates. The experiment was repeated twice, and representative results are displayed. See also FIG. 15.

FIG. 10A is a sequence alignment of O. sativa coronatine-degradable proteins (Tan et al., "Mechanism of Auxin Perception by the TIR1 Ubiquitin Ligase," Nature 446:640-645 (2007), which is hereby incorporated by reference in its entirety) OsJAZ1 (NP_001064513.1; SEQ ID NO: 4), OsJAZ2 (NP_001049167.1; SEQ ID NO: 5), OsJAZ7 (NP_001063273.1; SEQ ID NO: 6), OsJAZ3 (NP_001049166.1; SEQ ID NO: 7), and A. thaliana AtJAZ1 (NP_564075; SEQ ID NO: 8). Degron sequences used in this study are highlighted and degron names indicated on the right. FIG. 10B is a sequence alignment of the F-box domains used in the present application: hsSKP2 (NP_005974; SEQ ID NO: 9) amino acids 95-132, AtCOI1 (NP_565919; SEQ ID NO: 10) amino acids 1-51 and OsTIR1 (NP_001052659.1; SEQ ID NO: 11) amino acids 1-39. FIG. 10C is a schematic representation of the hormone receptor structure of different pJAZ versions. Each receptor is composed of combinations of: human SKP2 FBox domain ("HsSKP2$^{F-box}$"), either full-length human SKP1 ("HsSKP1") or HsSKP1 lacking its F-box binding region (amino acids 1-129, "HsSKP1$^{Δ1-129}$"), rice TIR1 F-box domain ("OsTIR1$^{F-box}$") and A. thaliana COI1 Leucine-Rich Repeats ("AtCOI1$^{LRR}$"). FIG. 10D is a graph showing the percent degradation in HEK-293T cells infected with the pJAZ versions depicted in FIG. 10C. All pJAZ vectors harbored GFP-AtJAZ$^{23}$. Cells were treated with 0.1% DMSO or 50 μM coronatine for 24 hours. GFP level was analyzed by flow cytometry and % degradation was calculated as described in the Methods. The experiment was conducted twice, and error bars represent standard deviation of biological replicates. FIG. 10E shows a western blot analysis of HEK-293T cells infected with pJAZ 2 (harboring OsTIR1$^{F-box}$-AtCOI1$^{LRR}$ and GFP-AtJAZ23), pJAZ 2$^{HA}$ (harboring HA-OsTIR1$^{F-box}$-AtCOI1$^{LRR}$ and GFP-AtJAZ$^{23}$) or pRAIDRS7$^{HA}$ (harboring HA-OsTIR1 and GFP-AID$^{47}$). β-Actin serves as loading control. The experiment was conducted twice, and representative results are displayed. See FIG. 15 for un-cropped blots. FIG. 10F show GFP fluorescence histograms derived from flow cytometric analysis of HEK-293T cells infected with the indicated pJAZ versions, selected and treated with either 0.1% DMSO ("Con") or 50 μM coronatine ("Cor"). Parental HEK-293T cells were analyzed as a control for background autofluorescence. An arrow points to a population of GFP$^{low}$ cells in control-treated cells infected with pJAZ 6-Os23. The top three and bottom two panels derive from different experiments. FIG. 10G are GFP and DAPI microscopic images of HEK-293T cells infected with pJAZ 6 harboring GFP fused to the indicated degrons. FIG. 10H show the relative median fluorescence of HEK-293T cells infected with pJAZ 7 harboring either GFP-OsJAZ[33] or NLS-GFP-OsJAZ[33]. Cells were selected and treated with increasing concentrations of coronatine ("Cor") and analyzed after 24 hours (left panel), or with 50 µM coronatine for the indicated time periods (right panel). GFP fluorescence was analyzed by flow cytometry. The experiment was conducted twice, and representative results are displayed. FIG. 10I shows that NLS-GFP-OsJAZ33 degradation is dependent on the presence of coronatine and coronatine receptor. HEK-293T cells were infected in duplicates with pJAZ (version 7) containing an NLS-GFP-OsJAZ[33] or with the same vector lacking coronatine receptor ("CorR"). To control for the structure and size of the vector, CorR (OsTIR1$^{F-box}$-OsCOI1B$^{LRR}$) was replaced with an auxin receptor (OsTIR1). Cells were selected and treated with 50 µM coronatine ("Cor") or 0.1% DMSO. GFP fluorescence was measured using a flow cytometer and was normalized to the relative level of GFP mRNA in each sample in order to control for differences in vector copy number and expression levels. Notably, the normalized fluorescence level of GFP was not affected by the presence of CorR in the absence of coronatine, indicating lack of coronatine-independent degradation. Moreover, coronatine treatment led to GFP degradation in CorR-dependent manner. Error bars represent the standard deviation of two biological replicates. FIGS. 10J-10K show that coronatine treatment does not affect proliferation in human ESCs. H9 mESCs expressing pJAZ NLS-GFP-OsJAZ[33] were grown in the presence of 50 µM coronatine ("Cor") or 0.1% DMSO ("Con"). In FIG. 10J, flow cytometry was used to validate coronatine-dependent GFP degradation after 1 day of treatment. Cells were counted daily and growth curves are plotted in FIG. 10K. The experiment was performed in triplicate, and a two-tailed paired t-test was used to calculate statistical significance. p-values are presented for each time point. Error bars represent standard deviation of technical replicates. FIGS. 10L-10M show that coronatine treatment does not affect global gene expression patterns in human ESCs. H9 mESCs expressing pJAZ NLS-GFP-OsJAZ33 were treated for 2 days with 50 µM coronatine or 0.1% DMSO and collected for mRNA-Seq analysis. Experiment was performed twice (RepA and RepB). FIG. 10L is a pairwise Spearman analysis showing perfect correlation between all samples. FIG. 10M show that only two genes (HISTIH4H and LINC01547) demonstrated differential expression between coronatine and control samples. As controls, Fragments Per Kilobase of transcript per Million mapped reads values ("FPKM") are listed for Brachyury (T) and OCT4 (POU5F), representing a differentiation marker (not expressed in hESCs) and a pluripotency marker (highly expressed in hESCS), respectively. These data suggest that HISTIH4H and LINC01547 are expressed at very low levels, and are unlikely significant to hESCs biology. Moreover, when the same search criteria were applied to identify genes that are differentially regulated between RepA and RepB (regardless of coronatine treatment), 7 genes were identified. This suggests that the two genes differentially expressed following coronatine treatment do not represent a significant transcriptional response, and are likely a result of inherent experimental noise.

FIG. 11A shows the percent degradation in HEK-293T cells infected with the indicated pJAZ versions, selected and treated for 1 day with coronatine. GFP fluorescence was measured by flow cytometry and % degradation was calculated. The corresponding components and biological replicate number (n) are indicated. The bar for pJAZ 6-Os23 is in grey color, to indicate reduced GFP fluorescence in non-treated cells (FIG. 10F). FIG. 11B shows the relative median fluorescence of HEK-293T cells infected with pRAIDRS NLS-GFP-AID[47] or pJAZ (version 7) NLS-GFP-OsJAZ[33], treated with the indicated concentrations of the corresponding hormone for 24 hours (left panel) or with 50 µM of hormone for the indicated time periods (right panel). GFP fluorescence was measured using flow cytometry. The experiment was repeated three times, and representative results are presented. In FIGS. 11C-11D, H9 hESCs were infected with pJAZ NLS-GFP-OsJAZ[33] ("GFP-J") or pJAZ OsJAZ[33]-p[53] ("J-p53") that harbors an shRNA targeting the 3'-UTR of p53 and an OsJAZ[33] degron-fused p53 coding sequence lacking UTRs. Selected hESCs were treated with 50 µM coronatine ("Cor") or 0.1% DMSO ("Con") for 1 day. FIG. 11C shows western blot analysis (upper panel) and protein level quantification (lower panel) demonstrating knockdown of endogenous p53 (*) and expression of J-p53 (**), as well as effective (90%) coronatine-dependent degradation of J-p53. FIG. 11D shows quantitative real-time PCR analysis for p53 target genes. Error bars represent the standard deviation of three technical replicates. P-values were calculated using unpaired Student's t-test. The experiment was repeated twice, and representative results are displayed. In FIGS. 11E-11G, H9 hESCs were infected with pJAZ NLS-GFP-OsJAZ[33] (harboring PuroR) and pRAIDRS NLS-mOrange-AID[47] (harboring BSD), selected and cloned. Cells were treated with either ethanol and DMSO ("Con"), auxin and DMSO ("IAA"), ethanol and coronatine ("Cor"), or auxin and coronatine ("IAA+Cor"). After 24 hours, microscopic bright-field ("BF") and fluorescence images were taken (FIG. 11E, scale bars, 100 µm) and cells were subjected to flow analysis (FIG. 11F, contour plots; FIG. 11G, quantification, error bars represent standard deviation.). Parental cells ("Par") are presented as autofluorescence control. Experiment was repeated three times and representative results are displayed. See also FIGS. 10A-10M, 12A-12G, and 15.

In FIG. 12G, the indicated cell types were infected, selected, and treated as above. Cells were subjected to flow cytometric analysis and quantification of median fluorescence levels is presented.

In FIGS. 13A-13D, H9 hESCs harboring pRAIDRS NLS-GFP-AID[47] ("GFP-A") or pRAIDRS NICD-AID[47] ("NICD-A") were maintained in mTeSR™1 media in the presence of 250 µM IAA. Cells were then washed twice and incubated for 3-5 days in the presence of 250 µM IAA (+) or 0.05% EtOH (-). FIG. 13A is a western blot analysis demonstrating the knockdown of the full-length NOTCH1 receptor (detected with the anti-NICD antibody as a protein migrating between 200 and 250 kDa) in pRAIDRS NICD cells and the accumulation of GFP-AID[47] following auxin removal. The diagonal line on the right side of the GFP blot was caused by a nick in the membrane. The accumulation of NICD-AID[47] following auxin removal is displayed in FIG. 14A. ca-Tubulin serves as a loading control. Un-cropped blots are displayed in FIG. 15. The experiment was performed twice, and representative results are displayed. FIG. 13B show the relative expression of endogenous NOTCH1 in pRAIDRS NICD-A cells. QRT-PCR performed with primers that amplify only the endogenous NOTCH1 gene demonstrates its knockdown at the mRNA level in pRAIDRS NICD-A cells. Experiment was performed 3 times and representative results are displayed. Error bars represent the standard deviation of 3 technical replicates. FIG. 13C shows bright field ("BF") and GFP fluorescence microscopic images, as well as microscope images of alkaline phosphatase ("AP")-assayed cells, demonstrating loss of ESC morphology and AP activity in pRAIDRS NICD-A cells in the absence of auxin. 4× digitally-magnified images of the outlined areas are presented as well. Scale bars, 100 µm. FIG. 13D shows QRT-PCR analysis of selected differentiation markers, as well as of the known NOTCH1 target HEY1. Results demonstrate the induction of differentiation in pRAIDRS NICD-A cells in the absence of auxin. The experiment was performed 3 times, and representative results are displayed. Error bars represent standard deviation of 3 technical replicates. FIG. 13E shows a heat map. H9 hESCs with the indicated pRAIDRS and pJAZ constructs were cultured for 4 days with mTeSR™-E8™, which contains FGF2 and TGFβ, or mTeSR™-E6 media, which lacks FGF2 and TGFβ, and treated with 250 µM IAA and 50 µM coronatine, where indicated. QRT-PCR analysis was performed for selected genes and GAPDH-normalized values are represented as a heatmap. Two biological replicates are displayed, with the gene symbols corresponding to each repeat colored black and red. For each biological replicate, QRT-PCR analysis was performed in triplicates and heatmap represent average values. For cells harboring pRAIDRS NICD-A and pJAZ dnM1-GFP-J, white rectangles mark instances where dnMAML1-GFP-J attenuated NICD-dependent activity by at least 2 fold (compared with the expression value in pRAIDRS NICD-A pJAZ GFP-J cells under the same condition). White circles indicate instances where coronatine treatment restored NICD-A-dependent activation by at least 2 fold.

FIG. 14A is a western blot analysis of pRAIDRS GFP-A and NICD-A hESCs maintained in the presence of 250 µM auxin ("IAA"), washed and incubated for 4 h in the presence (+) or absence (-) of auxin. The western blot demonstrates NICD-A accumulation following auxin removal. α-Tubulin serves as a loading control. The experiment was repeated twice, and a representative blot is displayed. FIG. 14B shows images of hESCs harboring pRAIDRS NICD-A and pJAZ dnM1-GFP-J were treated with 50 µM coronatine (+) or 0.1% DMSO (-) for 1 day. Bright-field ("BF") and fluorescence microscopic images demonstrate effective coronatine-dependent degradation of dnM1-GFP-J. Scale bars, 100 µm. Dashed lines mark colony borders. The experiment was conducted more than three times, and representative images are displayed. FIG. 14C shows the relative expression of hESCs harboring pRAIDRS NICD-A or GFP-A and pJAZ GFP-J or dnM1-GFP-J cultured for 4 days with TeSR™-E8™, which contains FGF2 and TGFβ, or TeSR™-E6 media, which lacks FGF2 and TGFβ, and treated with 250 µM auxin and 50 µM coronatine where indicated. Quantitative real-time PCR analysis was performed for selected genes and GAPDH-normalized values are displayed (error bars represent standard deviation of three technical replicates). Dashed lines indicate instances where coronatine-mediated dnM1-GFP-J degradation restored NICD-A-dependent activity by at least twofold. The experiment was repeated three times, and representative results are displayed. See also FIGS. 13A-13E and 15.

FIGS. 15A-15H are images of un-cropped immunoblots from FIG. 3A (FIG. 15A), FIG. 5A (FIG. 15B), FIG. 5E (FIG. 15C), FIG. 9A (FIG. 15D), FIG. 11C (FIG. 15E), FIG. 14A (FIG. 15F), FIG. 10E (FIG. 15G), and FIG. 13A (FIG. 15H). Numbers on the left of each blot represent molecular weight in KDa.

DETAILED DESCRIPTION OF THE INVENTION

Figure 1A:
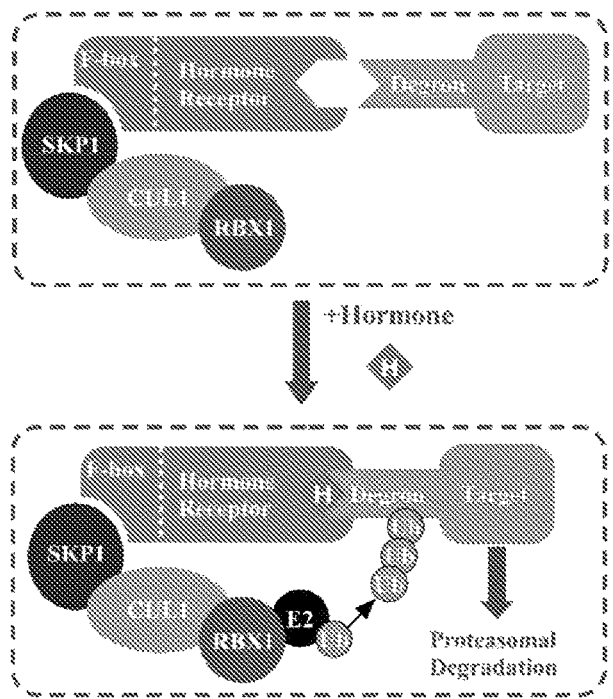
FIGS. 1A-1B illustrate a mechanisms of plant hormone-induced degradation and the structure of plant hormone-induced degradation vectors.

In plants, auxin (indole-3-acetic acid; "IA" A) induces degradation of a family of short-lived transcriptional repressors, the IAA proteins, by mediating the interaction of a degron domain in the target protein with the substrate recognition domain of an F-box protein, TIR1 (Hayashi et al., "The Interaction And Integration of Auxin Signaling Components," *Plant Cell Physiol.* 53: 965-975 (2012), which is hereby incorporated by reference in its entirety). Productive interaction of IAA proteins and TIR1 in the presence of auxin leads to ubiquitynation of the target by recruitment of a Skp1-Cullin-F box protein ("SCF") ubiquitin E3 ligase complex, followed by proteasomal degradation. The SCF complex is highly conserved among eukaryotes (Zimmerman et al., "Structural Assembly of Cullin-RING Ubiquitin Ligase Complexes," *Curr. Opin. Struct. Biol.* 20: 714-721 (2010), which is hereby incorporated by reference in its entirety), such that constitutive expression of TIR1 allows a reconstitution of the auxin induced degradation system in vertebrate cells. Due to the lack of an auxin-responsive system in animals, the hormone as well as the F-box protein are otherwise biologically silent and cause no measurable physiological changes in the absence of a target, thus minimizing possible side-effects of the treatment (Nishimura et al., "An Auxin-Based Degron System for the Rapid Depletion of Proteins in Nonplant Cells," *Nat. Methods* 6: 917-922 (2009), which is hereby incorporated by reference in its entirety). The role of auxin signaling through the F-box protein TIR-1 is analogous to the role of COI1-mediated jasmonate ZIM-domain ("JAZ") degradation in jasmonic acid ("JA") signaling.

The phytohormone JA and its metabolites regulate a wide spectrum of plant physiology, participating in normal development and growth processes as well as defense responses to environmental and pathogenic stressors. JA is activated upon specific conjugation to the amino acid L-isoleucine, which produces the highly bioactive hormonal signal (3R, 7S)-jasmonyl-L-isoleucine ("JA-Ile"). Coronatine ("COR") is a *Pseudomonas syringae* virulence factor that structurally mimics JA-Ile.

The discovery of coronatine-insensitive mutants enabled the identification of COI1 as a key player in the JA pathway. *Arabidopsis* COI1 is an F-box protein that functions as the substrate-recruiting module of the SCF ubiquitin E3 ligase complex. Like other E3 ligases, $SCF^{CO1}$ is involved in the ubiquitination of proteins, which targets the proteins for subsequent degradation by the 26S proteasome.

*Arabidopsis* JAZ proteins such as JAZ1, JAZ6, JAZ7, and JAZ8 are $SCF^{CO1}$ substrate targets that associate with COI1 in a hormone-dependent manner. In the absence of hormone signal, the JAZ proteins actively repress the transcription factor MYC2, which binds to cis-acting elements ofjasmonate-response genes. In response to cues that upregulate JA-Ile synthesis, the hormone stimulates the specific binding of JAZ proteins to COI1, leading to poly-ubiquitynation and subsequent degradation of the JAZ proteins by the 26S proteasome. JAZ degradation relieves repression of MYC2 and probably other transcription factors, permitting the expression of JA-responsive genes.

The present invention relates to a system for F-box hormone receptor regulated protein expression. The system includes a silencing nucleic acid molecule comprising a first promoter and an shRNA operably linked to the first promoter, where the shRNA silences expression of a target protein. The system also includes an expression nucleic acid molecule comprising a second promoter, an F-box hormone receptor operably linked to the second promoter, and a nucleic acid molecule encoding a fusion protein comprising a degron fused to the target protein, where the nucleic acid molecule encoding the fusion protein is operably linked to the second promoter.

As used herein, the term "promoter" refers to an untranslated DNA sequence usually located upstream of a coding region, which contains the binding site for RNA polymerase and initiates transcription of the gene downstream of the promoter into mRNA. The promoters of the present invention may be constitutive promoters, which constitutively induce the expression of a target gene. The promoters of the present invention may also be inducible promoters, which induce the expression of a target gene at a specific site and a specific time.

In one embodiment, the first promoter is an RNA polymerase III promoter. Exemplary RNA polymerase III promoters include, without limitation, U6 and H1 promoters. In some embodiments, the RNA polymerase III promoter is a U6 promoter.

In one embodiment, the second promoter is an RNA polymerase II promoter. The RNA polymerase II promoter may be a non-viral promoter. Exemplary non-viral RNA polymerase II promoters include, without limitation, phosphoglycerate kinase-1 ("PGK-1") and elongation factor 1α ("EF1α") promoters.

In another embodiment, the second promoter is a mammalian promoter. Suitable mammalian promoters include, without limitation, human, murine, bovine, canine, feline, ovine, porcine, ursine, and simian promoters. In one embodiment, the promoter is a human promoter.

The system of the present invention enables the genetic silencing of an endogenous protein of interest and its replacement with a degron-fused target protein in a mammalian cell. Silencing of the endogenous protein of interest is achieved through the expression of short hairpin RNA from the silencing nucleic acid molecule.

As used herein, the term "short hairpin RNA" or "shRNA" refers to an RNA molecule that leads to the degradation of mRNAs in a sequence-specific manner dependent upon complimentary binding of the target mRNA. shRNA-mediated gene silencing is well known in the art (see, e.g., Moore et al., "Short Hairpin RNA (shRNA): Design, Delivery, and Assessment of Gene Knockdown," *Methods Mol. Biol.* 629: 141-158 (2010), which is hereby incorporated by reference in its entirety).

As used herein, the term "target protein" refers to a protein of interest. The silencing nucleic acid molecule of the present invention enables the silencing of an endogenous protein of interest. The expression nucleic acid molecule of the present invention enables the expression of a protein of interest whose degradation is induced by a molecule that binds to an F-box hormone receptor. Proteins of interest include all cellular proteins, including, but not limited to, proteins involved in embryonic stem cell division, proliferation, and differentiation.

The shRNA may target the 5'-untranslated region ("5'-UTR"), the coding region, or the 3'-untranslated region ("3'-UTR") of a target protein. In one embodiment, the shRNA targets the 3'-UTR of the target protein. In another embodiment, the shRNA targets the 5'-UTR of the target protein. In yet another embodiment, the shRNA targets the coding region of the target protein.

In another embodiment, the shRNA targets a coding region of the target protein. In accordance with this embodiment, the fusion protein is resistant to silencing by the shRNA. For example, the nucleic acid molecule encoding the fusion protein may comprise silent mutations in the coding region of the target protein recognized by the shRNA (see, e.g., Jiang Y et al., "Rescue of the TTF2 Knockdown Phenotype with an siRNA-Resistant Replacement Vector," *Cell Cycle* 3:1151-1153 (2004) and Kim et al., "Coupling of RNAi-Mediated Target Downregulation with Gene Replacement," *Antisense Nucleic Acid Drug Dev.* 13:151-155 (2003), which are hereby incorporated by reference in their entirety).

As used herein, the term "F-box hormone receptor" refers to a plant protein or peptide containing at least one F-box domain that mediates the degradation of a degron-fused target protein in the presence of its respective hormone. The F-box hormone receptor may be codon-optimized for expression in mammalian cells. F-box hormone receptors are well known in the art (see, e.g., Spartz et al., "Plant Hormone Receptors: New Perceptions," *Genes Dev.* 22(16): 2139-2148 (2008), which is hereby incorporated by reference in its entirety).

In one embodiment, the F-box hormone receptor is selected from the group consisting of an auxin receptor or a jasmonate-isoleucine receptor. In another embodiment, the F-box hormone receptor is an auxin receptor. The auxin receptor may be Transport Inhibitor Response 1 ("TIR1"). Exemplary TIR1 receptors include, without limitation, *Oryza sativa* TIR1 ("OsTIR1"; NP_001052659; SEQ ID NO: 11), *Arabidopsis thaliana* TIR1, *Arabidopsis lyrata* TIR1, and TIR1 homologs from other plant species, e.g., grape, tomato, corn, rubber tree, pea, wild tobacco, soybean, sorghum, or wheat. In one embodiment, the TIR1 receptor is OsTIR1. In accordance with this embodiment, the OsTIR1 receptor is a codon-optimized for expression in mammalian cells.

When the OsTIR1 receptor is a codon-optimized for expression in mammalian cells, the expression nucleic acid molecule may comprise SEQ ID NO: 12.

In another embodiment, the F-box hormone receptor is a jasmonate-isoleucine receptor. The jasmonate-isoleucine receptor may be Coronatine Insensitive 1 ("COI1"). Exemplary COI1 receptors include, without limitation, *Arabidopsis thaliana* COI1 ("AtCOI1"; NP_565919; SEQ ID NO: 10), *Arabidopsis lyrata* COI1, *Oryza sativa* COI1B ("OsCOI1B"; NP_001055700), and COI1 homologs from other plant species, e.g., grape, tomato, corn, rubber tree, pea, wild tobacco, soybean, sorghum, or wheat. In one embodiment, the COI1 receptor is AtCOI1.

As used herein, the term "chimeric protein" refers to a protein or polypeptide comprising two or more heterologous domains which are not found in the same relationship to one another in nature. The F-box hormone receptor of the present invention may be a chimeric F-box hormone receptor. Exemplary chimeric F-box hormone receptors may comprise amino acids sequences from *Oryza sativa*, *Arabidopsis thaliana*, *Arabidopsis lyrata*, or any other plant species having orthologous F-box hormone receptors.

Chimeric F-box hormone receptors may also comprise amino acid sequences from human F-box hormone receptors including, but not limited to, SKP2 (SEQ ID NO: 9).

In one embodiment, the chimeric F-box hormone receptor comprises amino acids 2-39 of SEQ ID NO: 11 coupled to amino acids 59-597 of SEQ ID NO: 13 (OsCOIB; NP_001055700.1). In accordance with this embodiment, the chimeric F-box hormone receptor has the amino acid sequence of SEQ ID NO: 14 (OsTIR$^{F-box}$-OsCOI1B$^{LRR}$):

```
MYPYDVPDYATYFPEEVVEHIFSFLPAQRDRNTVSLVCKVWYEIE
RLSRKHVTVPFCYAASPAHLLARFPRLESLAVKGKPRAAMYGLIPEDWGA
YARPWVAELAAPLECLKALHLRRMVVTDDDLAALVRARGHMLQELKLDKC
SGFSTDALRLVARSCRSLRTLFLEECSIADNGTEWLHDLAVNNPVLETLN
FHMTELTVVPADLELLAKKCKSLISLKISDCDFSDLIGFFRMAASLQEFA
GGAFIEQGELTKYGNVKFPSRLCSLGLTYMGTNEMPIIFPFSALLKKLDL
QYTFLTTEDHCQLIAKCPNLLVLAVRNVIGDRGLGVVADTCKKLQRLRVE
RGDDDPGLQEEQGGVSQVGLTTVAVGCRELEYIAAYVSDITNGALESIGT
FCKNLCDFRLVLLDREERITDLPLDNGVRALLRGCTKLRRFALYLRPGGL
SDTGLGYIGQYSGIIQYMLLGNVGETDDGLIRFALGCENLRKLELRSCCF
SEQALARAIRSMPSLRYVWVQGYKASKTGHDLMLMARPFWNIEFTPPSSE
NANRMREDGEPCVDSQAQILAYYSLAGKRSDCPRSVVPLYPA.
```

The amino acid sequence of OsTIR$^{F-box}$-OsCOI1B$^{LRR}$ comprises a start codon (amino acid 1 of SEQ ID NO: 13), an HA Tag (amino acids 2-9 of SEQ ID NO: 13), and amino acids 2-39 of SEQ ID NO: 11 coupled to amino acids 59-597 of SEQ ID NO: 13.

As used herein, the term "degron" refers to a signal that targets a protein to a ubiquitin ligase complex in a hormone-dependent manner. Exemplary degrons include, without limitation, auxin-induced degradation ("AID") degrons and jasmonate ZIM-domain ("JAZ") degrons. The degrons of the present invention may comprise a full length wild type degron sequence or a portion of a full length wild-type sequence. In some embodiments, the degron is codon-optimized for expression in mammalian cells.

When the auxin receptor is Transport Inhibitor Response 1 ("TIR"), the degron is an auxin-induced degradation ("AID") degron. Exemplary AID degrons include, without limitation, *Arabidopsis thaliana* IAA14 (AtIAA14; SEQ ID NO: 1), *Arabidopsis thaliana* IAA7 (AtIAA7; SEQ ID NO: 2), *Arabidopsis thaliana* IAA17 (AtIAA14; SEQ ID NO: 3). In one embodiment, the AID degron comprises amino acids 63-109 of SEQ ID NO: 3 (AID$^{47}$). In another embodiment, the AID degron consists of amino acids 63-109 of SEQ ID NO: 3 (AID$^{47}$). In accordance with this embodiment, AID$^{47}$ is codon optimized for expression in mammalian cells.

When the jasmonate-isoleucine receptor is Coronatine Insensitive 1 ("COI1"), the degron is a jasmonate ZIM-domain ("JAZ") degron. Exemplary JAZ degrons include, without limitation, *Oryza sativa* JAZ1 (OsJAZ1; SEQ ID NO: 4), *Oryza sativa* JAZ2 (OsJAZ2; SEQ ID NO: 5), *Oryza sativa* JAZ3 (OsJAZ3; SEQ ID NO: 7), *Oryza sativa* JAZ7 (OsJAZ7; SEQ ID NO: 6), and *Arabidopsis thaliana* JAZ1 (AtJAZ1; SEQ ID NO: 8). The JAZ degron may comprise amino acids 109-141 or 104-146 of SEQ ID NO: 4. In one embodiment, the JAZ degron consists of SEQ ID NO: 15 (OsJAZ$^{33}$):

```
HAAALPEMPIARKASLQRFLQKRKHRITTTSEP.
```

In yet another embodiment, the JAZ degron consists of SEQ ID NO: 16 (OsJAZ$^{43}$):
```
PPQPAHAAALPEMPIARKASLQRFLQKRKHRITTTSEPYKKAA.
```

As used herein, the term "nuclear localization signal" or "NLS" refers to an amino acid sequence that directs import of a protein into the nucleus of the cell. The fusion protein of the present invention may further comprise a nuclear localization signal ("NLS"). When the degron is a JAZ degron, the fusion protein may further comprise a NLS. Nuclear localization signals are well known in the art and include, without limitation, the SV40 large T-antigen NLS (PKKKRKV; SEQ ID NO: 17).

In one embodiment, the fusion protein comprises a target protein fused to the amino terminus of the degron. In another embodiment, the fusion protein comprises a target protein fused the carboxyl-terminus of the degron.

In some embodiments, the expression nucleic acid molecule further encodes a selectable marker operably linked to the second promoter. Suitable selectable markers include, without limitation, puromycin N-acetyl-transferase ("PAC"), blasticidin-S deaminase ("BSD"), 3'-glycosyl phosphotransferase ("Neo"), and Hygromycin B phosphotransferase ("Hpt"). In one embodiment, the selectable marker is selected from the group consisting of puromycin N-acetyl-transferase and blasticidin-S deaminase.

The expression nucleic acid molecules of the present invention may further encode one or more self-cleaving peptides. The use of self-cleaving peptides in multi-gene expression systems ("MGES") is well known in the art and is discussed further in, e.g., Wang et al., "2A Self-Cleaving Peptide-Based Multi-Gene Expression System in the Silkworm *Bombyx mori*," *Scientific Reports* 5:16273 (2015) and Kim et al., "High Cleavage Efficiency of a 2A Peptide Derived from Porcine Teschovirus-1 in Human Cell Lines, Zebrafish and Mice," *PLoS ONE* 6:e18556 (2011), which are hereby incorporated by reference in their entirety. Self-cleaving peptides enable the simultaneous expression of multiple proteins from a single nucleic acid molecule.

In one embodiment, the expression nucleic acid molecule further encodes: (i) a first self-cleaving peptide between the F-box hormone receptor and the fusion protein and (ii) a second self-cleaving peptide between the fusion protein and the selectable marker. The first and second self-cleaving peptides may comprise porcine teschovirus-1 2A peptides.

The present invention also relates to a vector comprising the system of the present application, where the silencing nucleic acid molecule is coupled directly or indirectly to the expression nucleic acid molecule. The vector may be a lentiviral vector. As described above, lentiviral vectors enable the delivery of an independent rescue system containing continuously-expressed shRNA and an shRNA-immune hormone-degradable protein of interest that rescues the phenotype exerted by the shRNA. In some embodiments, the present invention relates to a mammalian cell infected with the lentiviral vector of the present application.

As used herein, the term "embryonic stem cells" refers to cells derived from embryonic sources that can self-renew and differentiate into multiple lineages.

As used herein, the term "cell line" or "cell lines" refers to a population of cultured cells derived from an identified parental cell type.

As used herein, the term "primary cell" or "primary culture" refers to a cell or a culture of cells that have been explanted directly from an organism, organ, or tissue. Primary cultures are typically neither transformed nor immortal.

In one embodiment, the mammalian cell is selected from the group consisting of embryonic stem cells, cell lines, and primary cells. Exemplary embryonic stem cells include, without limitation, cells from already established lines, embryo carcinoma cells, embryonic fibroblasts including murine embryonic cells, other embryo-like cells, cells of embryonic origin or cells derived from embryos, many of which are known in the art and available from the American Type Culture Collection, Manassas, Va. 20110-2209, USA, and other sources. Additional suitable cells include, without limitation, mouse and human induced-pluripotent cells, epiblast cells, epliblast-like cells, and primary fibroblasts.

The present invention further describes a method for F-box hormone receptor regulated protein degradation in a mammalian host cell. This method involves providing a mammalian host cell; introducing the system of the present application into the mammalian host cell to produce a transgenic mammalian host cell; culturing said transgenic mammalian host cell under conditions that result in (i) silencing expression of the target protein and (ii) expression of the fusion protein; and contacting said transgenic mammalian host cell with a molecule that binds the F-box hormone receptor so that said fusion protein undergoes degradation.

The silenced target protein may be endogenous to the mammalian host cell. As described above, the mammalian host cell may be selected from the group consisting of embryonic stem cells, cell lines, and primary cells.

In one embodiment, the F-box hormone receptor is Transport Inhibitor Response 1 ("TIR1"), the degron comprises amino acids 63-109 of SEQ ID NO: 3 ("AID$^{47}$"), and the molecule that binds the F-box hormone receptor is auxin (Indole-3-acetic acid, "IAA").

In another embodiment, the F-box hormone receptor is Transport Inhibitor Response 1 ("TIR1"), the degron comprises amino acids 63-109 of SEQ ID NO: 3 ("AID$^{47}$"), and the molecule that binds the F-box hormone receptor is 1-Naphthaleneacetic acid ("NAA").

The degron may consist of amino acids 63-109 of SEQ ID NO: 3 ("AID$^{47}$").

In one embodiment, the F-box hormone receptor has the amino acid sequence of OsTIR$^{F\text{-}box}$-OsCOI1B$^{LRR}$ (SEQ ID NO: 14), the degron comprises amino acids 109-141 of SEQ ID NO: 4, and the molecule that binds the F-box hormone receptor is coronatine. The degron may consist of SEQ ID NO: 15 (OsJAZ$^{33}$) or SEQ ID NO: 16 (OsJAZ$^{43}$). When the degron comprises a JAZ degron, the fusion protein may further comprises a nuclear localization signal.

In a further embodiment, the silencing nucleic acid molecule is coupled directly or indirectly to the expression nucleic acid molecule within a vector.

In one embodiment, the introducing is carried out by infecting the mammalian cell with a vector. The vector may be a lentiviral vector.

The present invention also describes a method for F-box hormone receptor regulated target protein degradation in a mammalian host cell. This method involves providing a mammalian host cell and infecting, into the mammalian host cell, a first lentiviral vector comprising (i) a first silencing nucleic acid molecule comprising a primary first promoter and a first shRNA operably linked to the primary first promoter, where the first shRNA silences expression of a first target protein and (ii) a first expression nucleic acid molecule comprising a primary second promoter, a Transport Inhibitor Response 1 ("TIR1") receptor operably linked to the primary second promoter, and a nucleic acid molecule encoding a first fusion protein comprising an auxin-induced degradation ("AID") degron fused to a first target protein, where the nucleic acid molecule encoding the first fusion protein is operably linked to the primary second promoter. The method further involves infecting, into the mammalian host cell, a second lentiviral vector comprising (i) a second silencing nucleic acid molecule comprising a secondary first promoter and a second shRNA operably linked to the secondary first promoter, where the second shRNA silences expression of a second target protein and (ii) a second expression nucleic acid molecule comprising a secondary second promoter, a Coronatine Insensitive 1 ("COI1") receptor operably linked to the secondary second promoter, and a nucleic acid molecule encoding a second fusion protein comprising a JAZ degron fused to a second target protein, where the nucleic acid molecule encoding the second fusion protein is operably linked to the secondary second promoter. The method further involves culturing the infected mammalian host cell under conditions that result in (i) silencing expression of the first and second target proteins and (ii) expression of the first and second fusion proteins; contacting the infected mammalian host cell with a molecule that binds the TIR1 receptor so that said first fusion protein undergoes degradation; and contacting the infected mammalian host cell with a molecule that binds the COI1 receptor so that said second fusion protein undergoes degradation.

The first and second silenced target proteins may be endogenous to the mammalian host cell. As described above, the mammalian host cell may be selected from the group consisting of embryonic stem cells, cell lines, and primary cells.

In one embodiment, the first expression nucleic acid molecule further encodes a selectable marker operably linked to the primary second promoter and (ii) the second expression nucleic acid molecule further encodes a selectable marker operably linked to the secondary second promoter. As described above, the selectable marker may be selected from the group consisting of puromycin N-acetyltransferase ("PAC") and blasticidin-S deaminase ("BSD").

As described above, the nucleic acid molecules of the present invention may further encode one or more self-cleaving peptides. When the first and second expression nucleic acid molecules further encode a selectable marker, the first and second nucleic acid molecules may also encode (i) a first self-cleaving peptide between the F-box hormone receptor and the fusion protein and (ii) a second self-cleaving peptide between the fusion protein and the selectable marker. In one embodiment, the first and second self-cleaving peptides are porcine teschovirus-1 2A peptides.

Infection of the first lentiviral vector and the second lentiviral vector may occur sequentially or simultaneously.

The infected mammalian host cell can be contacted with a molecule that binds TIR1 receptor and with a molecule that binds the COI1 receptor sequentially or simultaneously.

In one embodiment, the AID degron consists of amino acid 63-109 of SEQ ID NO: 3.

In another embodiment, the COI1 receptor is OsTIR1$^{F-box}$-OsCOIB1$^{LRR}$ (SEQ ID NO: 14).

The JAZ degron may comprise amino acids 109-141 of SEQ ID NO: 4. The JAZ degron may also consist of SEQ ID NO: 15 (OsJAZ$^{33}$) or SEQ ID NO: 16 (OsJAZ$^{43}$). When the degron comprises a JAZ degron, the fusion protein may further comprises a nuclear localization signal.

EXAMPLES

Material and Methods for Examples 1-4

Cell Culture.

HEK-293T, HCT-116 and NIH/393 cells were cultured in DMEM supplemented with 10% fetal bovine serum (FBS, Corning), 1 mM sodium pyruvate, 2 mM L-glutamine and PenStrep (all from Gibco). NCI-H358 and NCI-H1299 cells (obtained from the American Type Culture Collection) were cultured in RPMI-1640 (Cellgro) supplemented with 10% FBS, 1 mM sodium pyruvate, 2 mM L-glutamine and PenStrep. Validated, *mycoplasma*-free hESCs and mESCs were obtained from the Pluripotent Stem Cell Core Facility at ISMMS. ESCs were routinely monitored for ES-like morphology and expression of Nanog and Oct4 (Pou5f1) using quantitative real-time PCR. CCE and R1 mESCs, as well as P19 mouse embryonal carcinoma cells, were cultured in DMEM supplemented with 15% FBS, 1 mM sodium pyruvate, 2 mM L-glutamine, non-essential amino acids, PenStrep, 10 nM 2-mercaptoethanol and 100 U ml$^{-1}$ LIF (ESGRO) on plates coated with 0.1% gelatin (Millipore, catalogue number ES-006-B). H9 hESCs were cultured with mTeSR™ 1 (Stem Cell Technologies) on plates coated with Matrigel (BD Biosciences, catalog number 354234). For controlling the presence of FGF2 and TGFβ, TeSR™-E8™ and TeSR™-E6, which contain and lack FGF2/TGFb, respectively, were used. All cells were grown at 37° C. in a humidified atmosphere of 5% CO$_2$ and passaged on average twice per week. All cells were tested negative for *mycoplasma* using the e-Myco *Mycoplasma* PCR Detection Kit (iNtRON). Where indicated, cell numbers were recorded with each passage and population doublings were calculated as Log$_2$ (cell output/cell input).

Lentiviral Infection and Selection.

For the production of lentiviral particles, 1×10$^7$ HEK-293T cells were resuspended in growth media (as described above) and transfected with 20 mg lentiviral vector, 20 mg psPAX2 packaging plasmid and 10 mg pMD2.G envelope plasmid using the calcium phosphate method. Cells were then plated in a 10-cm dish and cultured for 1 day. On the second day, media were replaced and cells were incubated at 32° C. Viral supernatants were collected on the morning and evening of the third and fourth days, passed through a 0.22- or 0.45-mm cellulose acetate filter and concentrated ~25-fold using an Amicon Ultra-15 Centrifugal Filter (Millipore). Cells were infected with concentrated virus diluted in their appropriate media in the presence of 8 mg ml$^{-1}$ polybrene (Sigma) for ~16 h at 37° C. Selection was applied 2 days following infection with either 1-2 mg ml$^{-1}$ Puromycin (Fisher Scientific) or 10-20 mg ml$^{-1}$ Blasticidin-S (Fisher Scientific). Where indicated, colonies (clones) of mESCs and hESCs with typical ESC morphology were manually isolated and expanded.

Chemicals and Treatments.

Auxin (IAA, Fisher Scientific, catalogue number AC12216) was dissolved in ethanol to a final concentration of 500 mM. Cells were treated with 50 μM IAA or 0.01% ethanol as a control, unless otherwise indicated. Coronatine (Sigma, catalogue number C8115) was first dissolved in dimethylsulfoxide ("DMSO") to a concentration of 50 mM and then diluted in DMEM to a final concentration of 5 mM. Cells were treated with 50 μM coronatine or with 0.1% DMSO as a control, unless otherwise indicated. Aphidicolin (Fisher Scientific, catalogue number AC61197) was diluted in DMSO to a final concentration of 10 mM. Cells were treated with 1 μM aphidicolin or with 0.01% DMSO as a control, unless otherwise indicated. All trans-retinoic acid (Fisher Scientific, catalogue number 302-79-4) was dissolved in ethanol.

Staining.

Stemgent's Alkaline Phosphatase staining kit (catalog number 00-009) was used according to the manufacturer's protocol. Crystal violet (CV) staining was performed by incubating cells for 5 minutes with CV solution (10 mM CV, 10% ethanol in water), followed by three to five gentle washes with water. For both AP and CV staining, plates were scanned using a standard desktop scanner and images were digitally adjusted for brightness and contrast. Acetic acid was used to extract CV, which was then quantified using a spectrophotometer at 590 nm. DAPI (4',6-diamidino-2-phenylindole) staining was performed by fixing cells (plated on cover slips) with 4% paraformaldehyde in PBS for 30 minutes, washing twice with PBS (for 5 minutes), treating with 0.2% Triton X-100 and 1% BSA in PBS for 30 min, washing with PBS and incubating with 0.2 mg ml$^{-1}$ DAPI for 10 minutes. Cells were then washed once with PBS and mounted on microscope slides. Images acquired with a microscope were digitally adjusted for brightness and contrast. All images from the same experiment were processed identically.

Flow Cytometry.

Flow cytometry was performed on a BD LSRII machine. For GFP and mOrange fluorescence analysis, cells were trypsinized, neutralized with FBS-containing media, supplemented with 0.2 mg ml$^{-1}$ DAPI and kept on ice. Cells were gated on forward scatter area ("FSC-A") and side scatter area ("SSC-A"), on FSC width ("FSC-W") and FSC-A to eliminate cell aggregates, and on FSC-A and DAPI to eliminate dead cells. GFP and mOrange fluorescence intensities were detected using the fluorescein isothiocyanate ("FITC") and DsRed channels, respectively. Background autofluorescence was measured using parental noninfected cells. Background-subtracted median fluorescence was normalized to the control-treated sample, to calculate relative median fluorescence. To calculate % degradation, relative median fluorescence was subtracted from 1. For measurement of apoptotic index, cells were collected by trypsinization together with all cells floating in the media, counted and $3\times10^5$ cells per sample were washed twice with PBS and stained using Annexin V:PE Apoptosis Detection Kit I (BD Biosciences, catalog number 559763) according to the manufacturer's protocol. Cells were gated on FSC-A and SSC-A, and on FSC-W and FSC-A to eliminate cell aggregates. 7-aminoactinomycin D ("7-AAD") was detected using the PerCP-Cy5.5 filter. Apoptotic index was calculated as the percentage of cells that are 7-AAD negative and Annexin V-Phycoerythrin positive. For measurement of mitotic index, cells were collected by trypsinization together with all cells floating in the media, neutralized with FBS-containing media, washed and fixed by slowly adding ice-cold 70% ethanol/Hank's balanced salt solution while vortexing. Cells were kept for at least 2 hours at −20° C., washed with PBS, incubated for 15 minutes on ice with 0.25% Triton X-100 in PBS and resuspended in 100 ml PBS-BA (PBS supplemented with 1% BSA and 0.02% sodium azide) containing 2 ml anti-Phospho-Histone H3 Ser10 antibody (Cell Signaling, catalog number 9706). Cells were incubated for 2 hours at room temperature with gentle rocking, washed twice with PBS-BA, resuspended in 100 ml PBS-BA supplemented with Alexa Fluor 546 secondary antibody (1:200, Life Technologies), incubated for 30 minutes at room temperature in the dark with gentle rocking, washed with PBS-BA, resuspended in 400 ml PBS containing 50 mg ml$^{-1}$ RNAse-A and incubated 30 minutes at 37° C. in the dark. Samples were then cooled, supplemented with DAPI to a final concentration of 2 mg ml$^{-1}$ and incubated on ice for 15 minutes. Unstained and secondary-antibody only samples served as controls. For analysis of cell-surface SSEA-1 expression, cells were trypsinized, washed three times with PBS supplemented with 0.5% BSA (PBSB) and $1\times10^5$ cells were resuspended in 25 ml PBSB and 10 ml PE-conjugated anti-SSEA-1 antibody (R&D Systems, catalog number FAB2155P) or IgG-PE for isotype control, incubated 30 minutes on ice, washed twice with PBSB, filtered and supplemented with DAPI to a final concentration of 0.2 mg ml$^{-1}$.

Quantitative Real-Time PCR and Expression Heatmaps.

Total RNA was extracted using TRIZOL (Ambion) and 1-2 µg were reverse transcribed using the High Capacity Reverse Transcription Kit (Life Technologies, catalog number 4368814) according to the manufacturer's protocol. QRT-PCR was performed in triplicates or quadruplicates using the Fast SYBR Green Master Mix (Life Technologies, catalog number 4385612) on a LightCycler480 Real-Time PCR System (Roche). Expression was calculated using the ACt method. Relative expression was calculated by dividing the average level of each gene to that of the housekeeping gene GAPDH measured in the same cDNA sample. Gene-specific primers are listed in Table 2. When data are displayed as bar charts, error bars represent the standard

TABLE 2

QRT-PCR Primers.

| Target | Forward Primer Sequence (5'-3') | SEQ ID NO. | Reverse Primer Sequence (5'-3') | SEQ ID NO. |
|---|---|---|---|---|
| Human GAPDH | acccactcctccacctttga | 18 | ctgttgctgtagccaaattcgt | 19 |
| Human HPRT1 | gaccagtcaacaggggacat | 20 | cctgaccaaggaaagcaaag | 21 |
| Human MDM2 | gaatcatcggactcaggtacatc | 22 | tctgtctcactaattgctctcct | 23 |
| Human p21 (CDKN1A) | tgtccgtcagaacccatgc | 24 | aaagtcgaagttccatcgctc | 25 |
| Human HEY1 | aggagagtgcggacgagaat | 26 | aacctagagccgaactcaagt | 27 |
| Human HES5 | accgcatcaacagcagcat | 28 | gaaggctttgctgtgcttcag | 29 |
| Human T (Brachyury) | cagtggcagtctcaggttaagaagga | 30 | cgctactgcaggtgtgagcaa | 31 |
| Human SOX1 | tttcccctcgctttctca | 32 | tgcaggctgaattcggtt | 33 |
| Human GATA3 | gcccctcattaagcccaag | 34 | ttgtggtggtctgacagttcg | 35 |
| Human GATA6 | gcgggctctacagcaagatg | 36 | acagttggcacaggacaatcc | 37 |
| Human NANOG | cctgaagacgtgtgaagatgag | 38 | gctgattaggctccaaccatac | 39 |

TABLE 2-continued

QRT-PCR Primers.

| Target | Forward Primer Sequence (5'-3') | SEQ ID NO. | Reverse Primer Sequence (5'-3') | SEQ ID NO. |
|---|---|---|---|---|
| Human PAX6 | aggtattacgagactggctcc | 40 | tcccgcttatactgggctattt | 41 |
| Human CXCR4 | atgaaggaaccctgtttccgt | 42 | agatgatggagtagatggtggg | 43 |
| Human Endogenous NOTCH1 | cctgcccgttcttgaaatgt | 44 | ggagcatcttcttcggaacct | 45 |
| Mouse Cdx2 | caaggacgtgagcatgtatcc | 46 | gtaaccaccgtagtccgggta | 47 |
| Mouse Cxcl12 | tgcatcagtgacggtaaacca | 48 | ttcttcagccgtgcaacaatc | 49 |
| Mouse Esrrb | caggcaaggatgacagacg | 50 | gagacagcacgaaggactgc | 51 |
| Mouse Fas (CD95, APO-1) | tatcaaggaggcccattttgc | 52 | tgtttccacttctaaaccatgct | 53 |
| Mouse Gapdh | agaacatcatccctgcatcc | 54 | cacattggggtaggaacac | 55 |
| Mouse Gata4 | ccctacccagcctacatgg | 56 | acatatcgagattggggtgtct | 57 |
| Mouse Gata6 | ttgctccggtaacagcagtg | 58 | gtggtcgcttgtgtagaagga | 59 |
| Mouse Hand1 | cccctcttccgtcctcttac | 60 | ctgcgagtggtcacactgat | 61 |
| Mouse Mdm2 | tgtctgtgtctaccgagggtg | 62 | tccaacggactttaacaacttca | 63 |
| Mouse Mixl1 | atccgcccggaccctccaaa | 64 | tcggttctggaaccacacctgga | 65 |
| Mouse Nestin (Nes) | aggagaagaagaaccaagaatggagga | 66 | tcggcttctggacctcccagt | 67 |
| Mouse Noxa (Pmaip1) | aaaagagcaggatgaggagcc | 68 | gtccttcaagtctgctggcac | 69 |
| Mouse p21 (Cdkn1a) | cctggtgatgtccgacctg | 70 | ccatgagcgcatcgcaatc | 71 |
| Mouse Pax3 | gcagcgcaggagcagaacca | 72 | gcactcgggcctcggtaagc | 73 |
| Mouse Sox1 | atgcaccgctacgacatggg | 74 | gctccgacttgaccagagatcc | 75 |
| Mouse Sox17 | cgcacggaattcgaacagta | 76 | gtcaaatgtcggggtagttg | 77 |
| Mouse Sox7 | cccccgaccttcaggggacaag | 78 | ggacagtgtcagcgccttccat | 79 |
| Mouse T (Brachyury) | gcttcaaggagctaactaacgag | 80 | ccagcaagaaagagtacatggc | 81 |
| Mouse Tcl1 | aaattccaggtgatcttgcg | 82 | tgtccttggggtacagttgc | 83 |
| eGFP-1 | agccgctaccccgaccacat | 84 | cggttcaccagggtgtcgcc | 85 |
| eGFP-2 | gacggcgacgtaaacggcca | 86 | cagcttgccggtggtgcaga | 87 | deviation of technical replicates. To generate gene expression heatmaps, normalized average expression levels were analysed using the Gene Cluster 3.0 Software (de Hoon et al., "Open Source Clustering Software," *Bioinformatics* 20:1453-1454 (2004), which is hereby incorporated by reference in its entirety). Data were log transformed and genes were mean centered. Genes were then hierarchically clustered using uncentered correlation similarity metric and average linkage.

Western Blot Analysis.

Figures 15A, 15B, 15C, 15D:
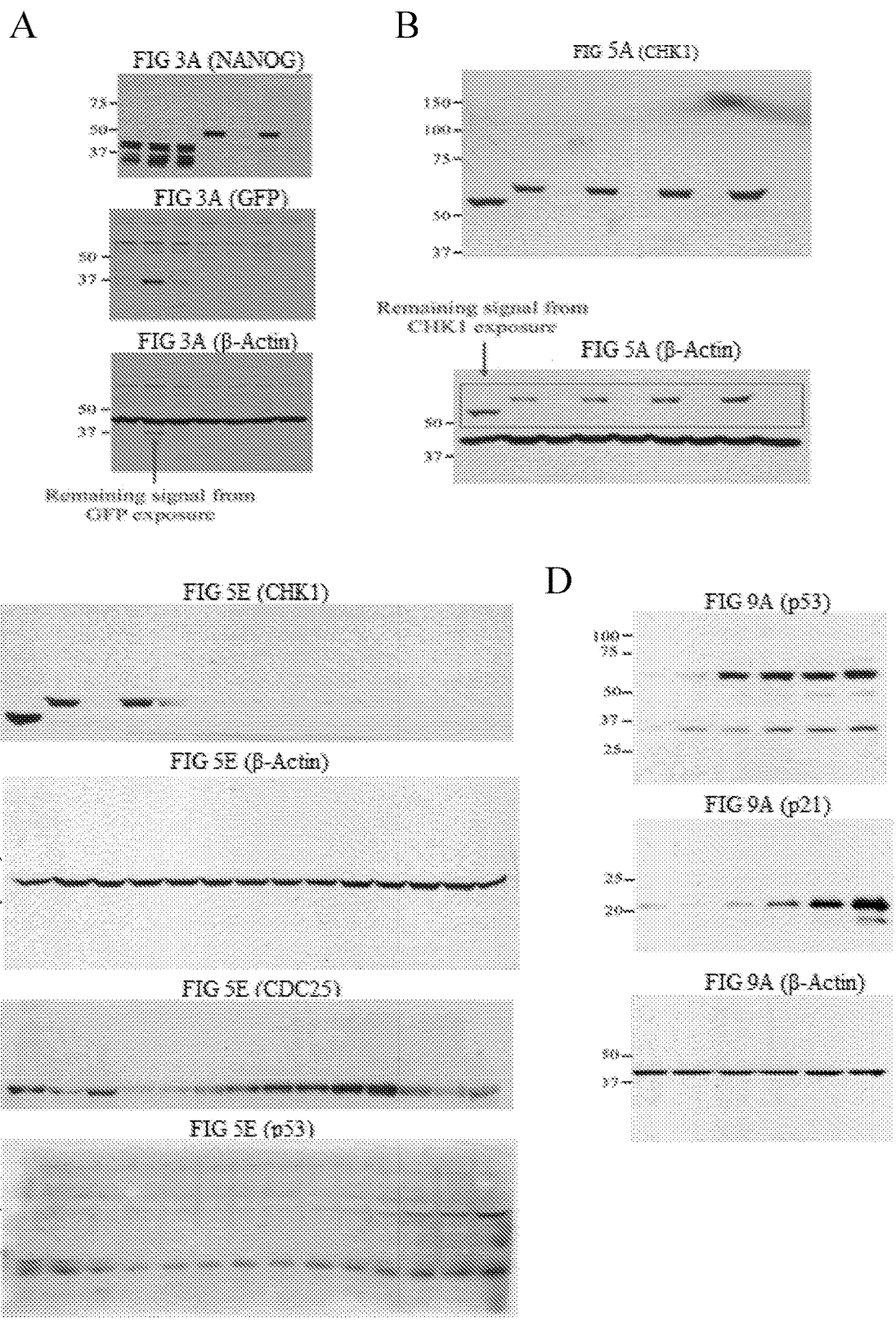
Figure 15H:
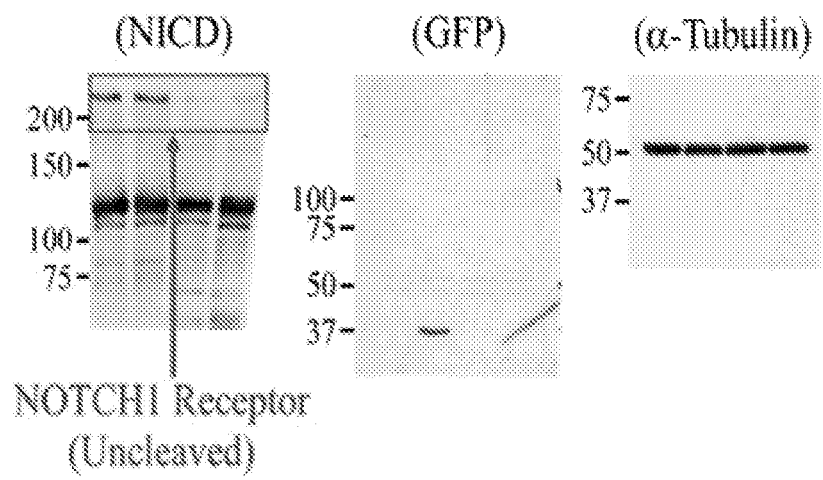

Cells were lysed in RIPA-B buffer (20 mM $Na_2HPO_4$ pH 7.4, 150 mM NaCl and 1% Triton X-100) supplemented with Protease Inhibitor Cocktail (Roche) for 30 minutes on ice with occasional vortexing, followed by 30 minutes centrifugation at 13,000 relative centrifugal force at 4° C. For $CDK^{pY15}$ detection, lysis buffer was supplemented with 1 mM dithiothreitol, 50 mM NaF, 30 mM tetrasodium pyrophosphate, 0.1 mM sodium orthovanadate, 10 mM β-glycerophosphate, and 15 mM para-nitrophenylphosphate. The BCA Protein Assay Kit (Thermo Scientific, catalog number 23225) was used to determine protein concentration. Next, 20-75 µg protein were separated by SDS-PAGE and transferred to polyvinylidene difluoride membranes (Bio-Rad). Membranes were blocked with TBST (10 mM Tris-HCl pH 7.9, 150 mM NaCl and 0.05% Tween-20) containing 3% skim milk, incubated with primary antibodies overnight, washed three times with TBST, incubated with horseradish peroxidase-conjugated secondary antibodies (Amersham), washed three times with TBST and subsequently reacted with ECL or ECL Prime (GE Healthcare). Luminescence was detected with X-ray films, which were scanned, or using the Bio-Rad ChemiDoc MP System. Blots were processed digitally by adjusting the brightness and contrast, and by rotating and cropping, when necessary. The following primary antibodies were used: rabbit anti-GFP (Invitrogen, catalog number A-6455, 1:500), mouse anti- CHK1 (FL-393, Santa Cruz Biotechnology, catalog number sc-8408, 1:1,000), mouse anti-β-actin (Sigma, catalog number A2066, 1:4,000), rabbit anti-p53 (DO-1, Santa Cruz Biotechnology, catalog number sc-6243, 1:1,000), mouse anti-p53 (Santa Cruz Biotechnology, catalog number sc-126, 1:500), rabbit anti-p21 (Santa Cruz Biotechnology, catalog number sc-397, 1:500), rabbit anti-NANOG (Millipore, catalog number AB5731, 1:1,000), mouse anti-HA (Abcam, catalog number ab 16918, 1:4,000), rabbit anti-phospho Cdc2 (CDK1) Tyr15 (Cell Signaling, catalogue number 9111, 1:500), mouse anti-CDC25A (Santa Cruz Biotechnology, catalog number sc-7389, 1:250), sheep anti-Notch-1 Intracellular Domain (R&D Systems, catalog number AF3647, 1:200), and mouse anti-α-Tubulin (Sigma, catalog number T9026, 1:1,500). Quantification of protein level was performed using the ImageJ software (Schneider et al., "NIH Image to ImageJ: 25 Years of Image Analysis," *Nat. Methods* 9:671-675 2012), which is hereby incorporated by reference in its entirety). Uncropped immunoblot scans are displayed in FIG. 15.

mRNA-Seq.

For testing the global transcriptional effect of coronatine treatment, H9 hESCs expressing pJAZ NLS-GFP-OsJAZ[33] and pRAIDRS NLS-mOrange-AID[47] were treated for 2 days with 50 µM coronatine (Cor) or 0.1% DMSO (Con). The experiment was repeated twice (replicates A and B). RNA was extracted with TRIZOL (Ambion). Sample preparation and sequencing was performed by Girihlet Inc. Briefly, total RNA was evaluated for quality and quantity using the Agilent RNA 6000 Nano Kit on an Agilent Bioanalyzer. Libraries were prepared using TruSeq RNA Library Prep Kit (Illumina). mRNA was isolated from 500 ng of total RNA using poly T beads and cDNA was synthesized using SuperScript Reverse Transcriptase (ThermoFisher Scientific) and random primers. The cDNA ends were blunted, 'A' base added and adapters ligated. A total of 15 cycles of PCR were performed to generate cDNA libraries. The libraries' concentration was measured using an Agilent DNA 1000 Kit on an Agilent Bioanalyzer. Libraries were sequenced on a NextSeq 500 machine (Illumina) with 1*75 bp reads.

Data Analysis.

The resulting fastq files were mapped to the human genome (version hg19) using the TopHat programme (with Bowtie2). The output .bam files were processed through the Cuffquant programme to generate normalized read counts. The resulting .cxb files were processed through the Cuffdiff programme to generate fragments per kilobase of transcript per million mapped reads (FPKM) values. Raw data (fastq files), as well as FPKM values, were uploaded to the GEO database (GSE74457). On average, there were $7.7 \times 10^7$ reads per sample, which mapped to 23,622 human genes. Lowly expressed genes with an average FPKM value <0.1 were excluded, narrowing the total gene count to 15,928. The BRB-Array Tools software (Simon et al., "Analysis of Gene Expression Data Using BRB-Array Tools," *Cancer Inform.* 3:11-17 (2007), which is hereby incorporated by reference in its entirety) was used to calculate Spearman pairwise correlation between all samples (FIG. 11L). To identify genes that were differentially regulated following coronatine treatment (FIG. 10M), the gene list was filtered to include genes that meet the following criteria: (1) genes that scored a P-value <0.05 in a two-tailed paired t-test comparing coronatine-treated samples with control samples; (2) genes that had a fold change >2 between coronatine and control samples in both replicates; and (3) coding genes and long non-protein-coding RNAs (excluding small RNAs). Using these criteria, only two genes demonstrated differential expression between coronatine and control samples. When the same criteria were applied to search for genes that were differentially regulated between the two biological replicates, seven such genes were identified.

Construction of pRAIDRS and pJAZ.

Initially, pRAIDRS and pJAZ vectors were synthesized as a cassette containing the following components (restriction enzyme-binding sites, REBSs, are italicized): *AscI*/pPGK-1 (partial sequence)/*SalI*/Kozak Sequence/Hormone Receptor/*EcoRV*/5'-P2A/5'-MC S/Degron/3'-MC S/3'-P2A/*NsiI*/Selectable Marker/*AatII* . . . *KpnI*. Cassettes were cloned using AscI+KpnI into an empty pLKO. 1-Puro lentiviral vector (Moffat et al., "A Lentiviral RNAi Library for Human and Mouse Genes Applied to an Arrayed Viral High-content Screen," *Cell* 124:1283-1298 (2006), which is hereby incorporated by reference in its entirety). Different versions of the vectors were then constructed by shuffling components between existing versions or adding new components using restriction enzymes. Specifically, degrons were cloned using XmaI+XbaI, hormone receptors with SalI+EcoRV and selectable markers with PstI+AatII. When indicated, restriction-free cloning (RFC) (Ulrich et al., "Exponential Megapriming PCR (EMP) Cloning-Seamless DNA Insertion into Any Target Plasmid without Sequence Constraints," *PLoS ONE* 7:e53360 (2012), which is hereby incorporated by reference in its entirety) was used. Primers and shRNA sequences are listed in Tables 3 and 4, respectively.

TABLE 3

Cloning Primers.

| | Name | Primer Sequence (5' to 3') | SEQ ID NO. |
|---|---|---|---|
| 1 | F-Box-RF-F1 | caggggatcgtcgacgccaccatgacctacttccccgagg | 88 |
| 2 | F-Box-RF-R1 | gggccattgtcacatgctcgcggctcagtctctcgatctcg | 89 |
| 3 | JAZ1-31-F1-XmaI | atattacccgggcctacacctctgacagagctgcctatcgccag | 90 |
| 4 | JAZ1-31-R1-XbaI | atactatctagaaggagccttgctggtcactctgtccttccgc | 91 |
| 5 | JAZ1-FL-F1-XmaI | acgtggcccgggatgtcgagttctatggaatg | 92 |
| 6 | JAZ1-FL-R1-XbaI | cgcggctctagatatttcagctgctaaaccgag | 93 |
| 7 | OsJAZ-33-F1 | tatattcccgggcacgccgctgccctgcctgagatgcctatcgccag | 94 |
| 8 | OsJAZ-33-R1 | tgactgtctagatggctcgcttgtggtggtgattctgtgcttccgc | 95 |

TABLE 3-continued

Cloning Primers.

| | Name | Primer Sequence (5' to 3') | SEQ ID NO. |
|---|---|---|---|
| 9 | HA-OsTir1-F1 | gtctgagtcgacgccaccatgtacccatacgatgttccagattacgctacctacttccccgaggaag | 96 |
| 10 | P2A-BstBI-R | atcttattcgaaggggccggggttctc | 97 |
| 11 | F-Box-RF-F3 | caggggatcgtcgacgccaccatgtacccatacgatgttccag | 98 |
| 12 | F-Box-RF-R3 | aaggcacggtcacgtgctttctgctcagtctctcgatctcg | 99 |
| 13 | NheI-NLS-GFP-F | gcagccgctagcccaaaaaagaaaagaaaagttatggtgagcaagggcgaggag | 100 |
| 14 | GFP-R2-XmaI | gatgtgcccgggcttgtacagctcgtccatgcc | 101 |
| 15 | mOrange-R1-XmaI | atcagtcccgggcttgtacagctcgtccatgc | 102 |
| 16 | GFP-F2-NheI | gatgtggctagcatggtgagcaagggcgaggag | 103 |
| 17 | mOrange-NheI-F1 | atcagagctagcatggtgagcaagggcgaggag | 104 |
| 18 | F-Box-RF-F2 | ggggatcgtcgacgccaccatggtttcatgggactcccttcc | 105 |
| 19 | F-Box-RF-R2 | ttgtcacatgctcgcgtgtctcagacgctaggcgatacca | 106 |
| 20 | HsSkp1-RF-F | caggggatcgtcgacgccaccatgccttcaattaagttgcagagt | 107 |
| 21 | HsSkp1-RF-R(a) | ccacttcctcggggaagtaggtcttctcttcacaccactggt | 108 |
| 22 | HsSkp1-RF-R(b) | gggccattgtcacatgctcgcgcttctcttcacaccactggt | 109 |
| 23 | HsSkp1-RF-R(c) | ccacttcctcggggaagtaggtccccttgatcatattggcaaca | 110 |
| 24 | HsSkp1-RF-R(d) | gggccattgtcacatgctcgcgccccttgatcatattggcaaca | 111 |
| 25 | pEF1α-RF-F | actttggccgcggctcgaggggctccggtgcccgtcag | 112 |
| 26 | pEF1α-RF-R | catggtggcgtcgacgatcccctcacgacacctgaaatggaa | 113 |
| 27 | mNanog-F1-XbaI | tgtcagtctagaatgagtgtgggtcttcctgg | 114 |
| 28 | mNanog-R1-BamHI | tgtcagggatcctatttcacctggtggagtc | 115 |
| 29 | mp53-F2-BstBI | tgtcagttcgaaatgactgccatggaggagtc | 116 |
| 30 | mp53-R2-NheI | tgtcaggctagcgtctgagtcaggccccactt | 117 |
| 31 | mChk1-F1-XbaI | ggtcagtctagaatggcagtgccttttgtgg | 118 |
| 32 | mChk1-R1-BamHI | ggtcagggatcctgtaacaggaaaccaaacc | 119 |
| 33 | mutAgeI-F3 | gaggggtcggcaattgaagcggtgcctagagaaggtg | 120 |
| 34 | mutAgeI-R3 | caccttctctaggcaccgcttcaattgccgaccccctc | 121 |
| 35 | FLAG-Tir1-F1 | gtctgagtcgacgccaccatggactacaaagacgatgacgacaagacctacttccccgaggaag | 122 |
| 36 | 3Myc-Tir1-F1 | gtctgagtcgacgccaccatggagcagaaactcattagcgaggaggacctgaacagcgaacagaaactcattccgaagaggatctcaactccgagcagaagctgatcagcgaggaggacctgagatccacctacttccccgaggaag | 123 |
| 37 | hNICD-F1-NheI | attctagctagcatgcggcggcagcatggccag | 124 |
| 38 | hNICD-R3-SnaBI | ctcggatacgtacttgaaggcctccggaatgc | 125 |
| 39 | hdnMAML1-F2-BstBI | attctattcgaactgccgcgggcacagcgcggtc | 126 |
| 40 | hdnMAML1-R2-NheI | attaaagctagcgtgcttcccggcgcgcttgg | 127 |
| 41 | hp53-F1-XbaI | agcttctagaatggaggagccgcagtcag | 128 |
| 42 | hp53-R1-BamHI | agctggatccgtctgagtcaggcccttctg | 129 |

TABLE 4 shRNA Oligonucleotides

| # | Name | Primer Sequence (5' to 3') | SEQ ID NO. |
|---|---|---|---|
| 101 | mNanog-shRNA-F | ccgggccaacctgtactatgtttaactcgagttaaacatagtacaggaggcttttg | 130 |
| 102 | mNanog-shRNA-R | aattcaaaaagccaacctgtactatgtttaactcgagttaaacatagtacaggttggc | 131 |
| 103 | mChk1-shRNA-F | ccggcccatgtagtagtatcactttctcgagaaagtgatactactacatgggtttt | 132 |
| 104 | mChk1-shRNA-R | aattaaaaaccatgtagtagtatcactttctcgagaaagtgatactactacatggg | 133 |
| 105 | hNOTCH1-shRNA-F | ccggctttgtttcaggttcagtattctcgagaatactgaacctgaaacaaagttttg | 134 |
| 106 | hNOTCH1-shRNA-R | aattcaaaaactttgtttcaggttcagtattctcgagaatactgaacctgaaacaaag | 135 |
| 107 | Luciferase-shRNA-F | ccggcttacgctgagtacttcgactcgagtcgaagtactcagcgtaagttttg | 136 |
| 108 | Luciferase-shRNA-R | aattcaaaaacttacgctgagtacttcgactcgagtcgaagtactcagcgtaag | 137 |
| 109 | hp53-shRNA-F | ccgggagggatgtttgggagatgtactcgagtacatctcccaaacatccctctttttg | 138 |
| 110 | hp53-shRNA-R | aattcaaaaagagggatgtagggagatgtactcgagtacatctcccaaacatccctc | 139 |

Sequences were codon-optimized (using the GeneArt algorithm) to increase their human Codon Adaptation Index ("CAI"), while avoiding the generation of any REBS that would render unique REBSs in the other parts of the vector non-unique. Components were designed and constructed as follows: OsTIR1 is a codon-optimized (CAI=0.95): *O. sativa* (rice) TIR1 gene (encoding NP_001052659; SEQ ID NO: 11), excluding the STOP codon. AtCOI1 is a codon-optimized (CAI=0.96) *A. thaliana* COI1 gene (encoding NP_565919; SEQ ID NO: 10), excluding the STOP codon. OsTIR1$^{F-box}$-AtCoi1$^{LRR}$: a chimeric receptor composed of an OsTIR1 F-box domain (Tan et al., "Mechanism of Auxin Perception by the TIR1 Ubiquitin Ligase," *Nature* 446:640-645 (2007), which is hereby incorporated by reference in its entirety) (amino acids 1-39) and an AtCOI1 leucine-rich repeat (Sheard et al., "Jasmonate Perception by Inositol-phosphate-potentiated COI1-JAZ Co-Receptor," *Nature* 468:400-405 (2010), which is hereby incorporated by reference in its entirety) (amino acids 52-592) was constructed using RFC. Megaprimers were generated using pRAIDRS as a template and primers 1+2. These megaprimers were used with pJAZ 1 as a template, to generate pJAZ 2. OsCOI1B is a codon-optimized (CAI=0.95) rice COI1B (encoding NP_001055700.1; SEQ ID NO: 13). OsTIR1$^{F-box}$-OsCOI1B$^{LRR}$ (SEQ ID NO: 14): a chimeric receptor composed of a Met-HA-tagged OsTIR1 F-box domain (Tan et al., "Mechanism of Auxin Perception by the TIR1 Ubiquitin Ligase," *Nature* 446:640-645 (2007), which is hereby incorporated by reference in its entirety) (amino acids 2-39 of SEQ ID NO: 11) and an OsCOI1B leucine-rich repeat (Sheard et al., "Jasmonate Perception by Inositol-phosphate-potentiated COI1-JAZ Co-Receptor," *Nature* 468:400-405 (2010), which is hereby incorporated by reference in its entirety) (amino acids 59-597 of SEQ ID NO: 13) was constructed using RFC. Megaprimers were generated using pJAZ 2$^{HA}$ as a template and primers 11+12. These megaprimers were used with pJAZ 5-Os23 or 5-At23 as a template, to generate versions 6-Os23 or 6-At23, respectively. 5'-P2A is a 2A peptide derived from porcine teschovirus-1. Codons were edited to achieve low degree (81%) of homology with the 3'-P2A sequence, to reduce recombination likelihood. 5'-MCS: four tandemly arranged 6-bp REBSs (BstBI, NheI/BmtI, SnaBI, and XmaI/SmaI). AID[47] is a codon-optimized (CAI=0.93) 47-amino acid segment that corresponds to amino acids 63-109 of *A. thaliana* IAA17 (AtIAA17, NP_171921; SEQ ID NO: 2). AID (corresponding to AtIAA17 amino acids 63-95) was generated by PCR amplification using AID[47] as a template and primers containing REBSs enabling replacement of the degron segment. AtJAZ[23] is a codon-optimized (CAI=0.96) 23-amino acid segment that corresponds to amino acids 199-221 of *A. thaliana* JAZ1 (AtJAZ1, NP_973862; SEQ ID NO: 8). AtJAZ[31] is an extended version of AtJAZ[23] and was PCR-amplified with AtJAZ[23] as a template and primers 3+4, and then cloned with XmaI+XbaI. AtJAZ$^{FL}$ is the full-length *A. thaliana* JAZ1 protein (non-codon optimized) and was PCR-amplified from a JAZ1-containing plasmid (Sheard et al., "Jasmonate Perception by Inositol-phosphate-potentiated COI1-JAZ Co-Receptor," *Nature* 468:400-405 (2010), which is hereby incorporated by reference in its entirety) with primers 5+6, and cloned with XmaI+XbaI. OsJAZ[23] is a codon-optimized (CAI=0.98) 23-amino acid segment corresponding to amino acids 114-136 of *O. sativa* JAZ1 (OsJAZ1, NP_001064513; SEQ ID NO: 4). OsJAZ[33] is an extended version of OsJAZ[23] (corresponding to OsJAZ1 amino acids 109-141) and was PCR amplified with OsJAZ[23] as a template and primers 7+8, and cloned with XmaI+XbaI. 3'-MCS: four tandemly arranged 6-bp REBSs (XbaI, HpaI, BamHI and PstI). It is noteworthy that PstI is not unique in vectors containing pEF1α or OsCOI1B$^{LRR}$. 3'-P2A is identical to 5'-P2A, except for different codon usage. PuroR is a codon-optimized (CAI=0.92) N-acetyltransferase gene. BSD is a codon-optimized (CAI=0.96) Blasticidin-S deaminase gene. HA tag: to generate pRAIDRS 7$^{HA}$, an HA tag (YPYDVPDYA), preceded by a methionine (Met), was inserted upstream of OsTIR1 by cassette PCR amplification with pRAIDRS as the template and primers 9+10, and cloning this cassette into pRAIDRS with SalI+BstBI. To generate pJAZ 2$^{HA}$, a Met-preceded HA tag was cloned upstream of the OsTIR1$^{F-box}$-AtCOI1$^{LRR}$ by cassette PCR amplification with pJAZ 2 as the template and primers 9+10, and cloning this cassette into pJAZ with SalI+BstBI. GFP: enhanced GFP was PCR amplified from pLKO.1-Puro-IRES-GFP with primers 16+14 and cloned into pJAZ or pRAIDRS using NheI+XmaI. mOrange was PCR amplified from pFUW-mOrange with primers 17+15 and cloned into pJAZ or pRAIDRS with NheI+XmaI. NLS: an SV40 large T-antigen NLS (PKKKRKV; SEQ ID NO: 17) was fused to the amino terminus of GFP or mOrange by PCR amplifying an NLS-GFP cassette with primers 13+14 or an NLS-mOrange cassette with primers 13+15, and cloning into pJAZ or pRAIDRS with NheI+XmaI. HsSKP2$^{F-box}$-AtCOI1$^{LRR}$: a chimeric receptor composed of an *Homo sapiens* SKP2 ("HsSKP2") F-box domain (amino acids 95-132 of SEQ ID NO: 9) and AtCOI1 leucine-rich repeat (Sheard et al., "Jasmonate Perception by Inositol-phosphate-potentiated COI1-JAZ Co-Receptor," *Nature* 468:400-405 (2010), which is hereby incorporated by reference in its entirety) (amino acids 50-592 of SEQ ID NO: 10) was constructed using RFC. Megaprimers were generated using HsSKP2-containing plasmid (Zheng et al., "Structure of the Cul1-Rbx1-Skp1-F boxSkp2 SCF Ubiquitin Ligase Complex," *Nature* 416:703-709 (2002), which is hereby incorporated by reference in its entirety) as a template and primers 18+19. These megaprimers were used with pJAZ 1 as a template to generate pJAZ 3. HsSKP1-AtCOI1$^{LRR}$ fusions: chimeric receptors composed of either full-length HsSKP1 or an N-terminal-truncated HsSKP1 lacking amino acids 1-129 (HsSKP1$^{Δ1-129}$) and either AtTIR1$^{F-box}$-AtCOI1$^{LRR}$ or just AtCOI1$^{LRR}$ were constructed using RFC. Megaprimers were generated using pCDNA3.1-SKP1-HA as a template and the following primer combinations: 20+21 for HsSKP1-OsTIR1$^{F-box}$-AtCOI1$^{LRR}$, 20+22 for HsSKP1-AtCOI1$^{LRR}$, 20+23 for HsSKP1$^{Δ1-129}$-OsTIR1F-box-AtCOI1$^{LRR}$ and 20+24 for HsSKP1$^{Δ1-129}$-AtCOI1$^{LRR}$. Megaprimers were used with pJAZ 2 as a template to generate pJAZ 4a-d. pEF1α: human EF1α promoter was cloned using RFC: megaprimers were generated using pEF1α-BirA-V5-His as a template and primers 25+26. These megaprimers were used to switch pPGK-1 into pEF1α in pRAIDRS and pJAZ. Site-directed mutagenesis (Zheng et al., "An Efficient One-Step Site-Directed and Site-Saturation Mutagenesis Protocol," *Nucleic Acids Res.* 32:e115 (2004), which is hereby incorporated by reference in its entirety) was performed with primers 33+34 to eliminate the AgeI site in pEF1α.

Construction of Rescue Systems.

Figure 16:
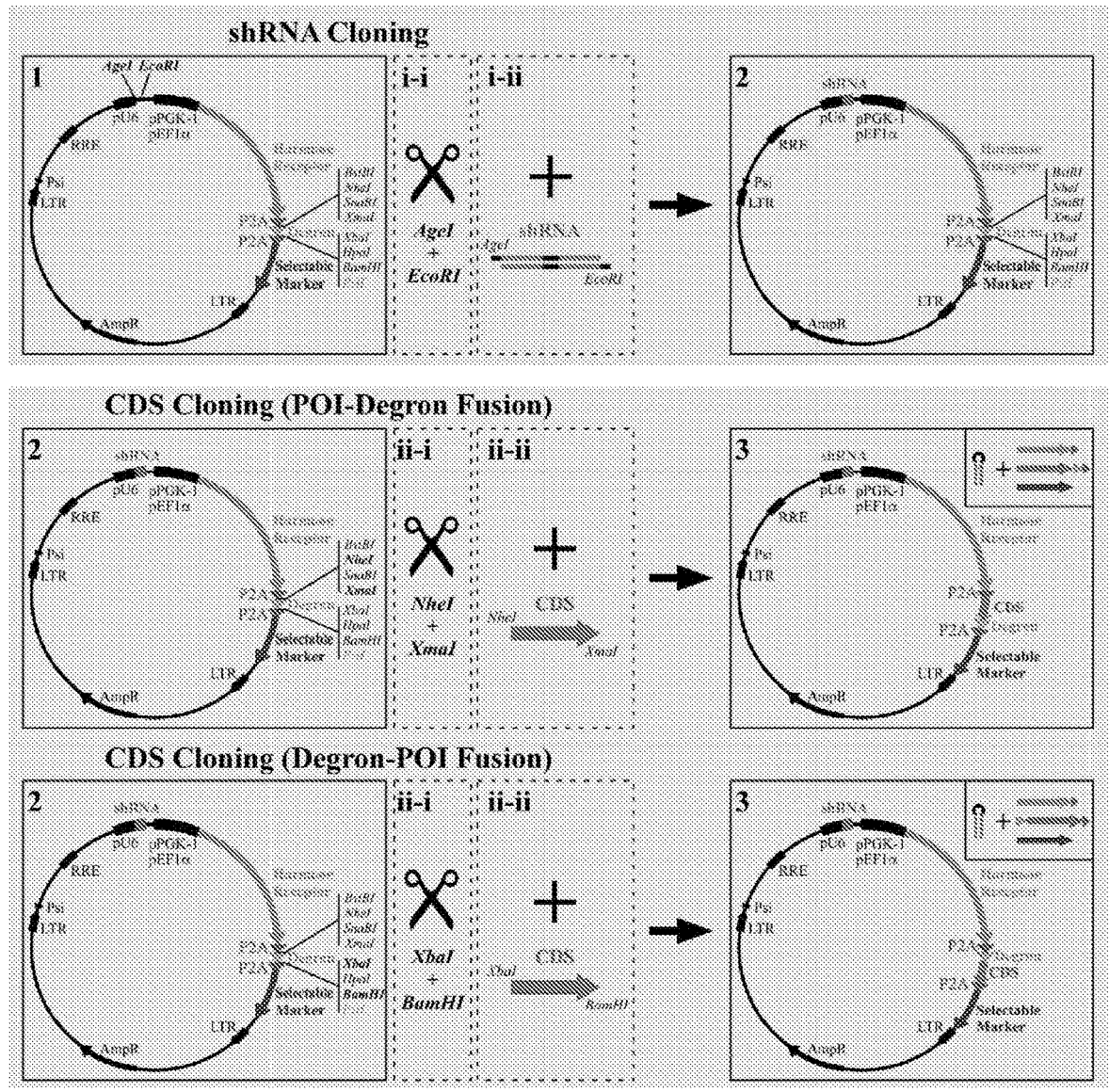
FIG. 16 shows a two-step cloning protocol. The strategy for constructing pRAIDRS/pJAZ rescue system plasmids is shown. In the first step, an empty pRAIDRS/pJAZ plasmid (Box 1) is restricted with AgeI+EcoRI (step i-i), purified and ligated with a small hairpin dsDNA duplex containing AgeI and EcoRI overhangs (step i-ii), which will give rise to the shRNA. In the second step, the POI's CDS is fused upstream or downstream of the degron, generating a POI-degron or degron-POI fusion, respectively. For example, to generate a POI-degron fusion, the shRNA-harboring plasmid (Box 2) is restricted with any desired combination of one or two REs from the 5'-MCS (e.g., NheI+XmaI) (step ii-i), purified, and ligated (step ii-ii) with the POI's CDS, which was previously PCR-amplified using primers containing NheI+XmaI sites, and restricted with these NheI+XmaI. Inlet boxes depict the post-processing components harbored by each version. All elements expressed from the PGK-1/EF1a promoter, including the RE sites, are in-frame. Hence, the cloned CDS must not include a STOP codon or any frame-shifting elements. The size of an empty pRAIDRS/pJAZ is ~9 kb (~6 kb between LTRs). Cloning extremely long CDSs may result in oversized viral genomes, which can hinder packaging and infection. Vectors harboring CDSs of 2 kb were sufficiently infectible. Testing multiple shRNA sequences before cloning the CDS is recommended. If possible, the shRNA should target the gene-of-interest's UTRs to avoid targeting of the exogenous CDS. If this is impossible, the exogenous CDS should contain 3-4 synonymous mutations in the central shRNA binding region in order to avoid targeting by the shRNA, as described by Lee et al. (Lee et al., "Combining Competition Assays with Genetic Complementation Strategies to Dissect Mouse Embryonic Stem Cell Self-Renewal and Pluripotency," *Nat. Protoc.* 7:729-748 (2012), which is hereby incorporated by reference in its entirety) PstI is not unique in vectors containing pEF1α or OsCOI1B[LRR].

In general, rescue system vectors were constructed using the two-step cloning protocol (FIG. 16). The specific components used were as follows: for pRAIDRS AID$^{47}$-NANOG (A-NANOG): an shRNA cassette targeting mouse Nanog 3'-UTR was generated by annealing oligonucleotides 101+102, as previously described (Lee et al., "Combining Competition Assays with Genetic Complementation Strategies to Dissect Mouse Embryonic Stem Cell Self-renewal and Pluripotency," *Nat. Protoc.* 7:729-748 (2012), which is hereby incorporated by reference in its entirety), and cloning into pRAIDRS with AgeI+EcoRI. Mouse Nanog CDS was amplified from pCR4-Nanog using primers 27+28 and cloned into the shRNA-containing pRAIDRS with XbaI+BamHI. For pRAIDRS p53-AID$^{47}$(p53-A): mouse p53 CDS was amplified from pSIN-EF2-Myc-Trp53 using primers 29+30 and cloned into pRAIDRS with BstBI+NheI. For pRAIDRS AID$^{47}$-CHK1 (A-CHK1): an shRNA cassette targeting mouse Chk1 3'-UTR was generated by annealing oligonucleotides 103+104 and cloning into pRAIDRS with AgeI+EcoRI. Mouse Chk1 CDS was amplified from pGEM-T-Chk1 using primers 31+32 and cloned into pRAIDRS with XbaI+BamHI. For pRAIDRS NICD-AID$^{47}$ (NICD-A): an shRNA cassette targeting human NOTCH1 3'-UTR was generated by annealing oligonucleotides 105+106 and cloning into pRAIDRS with AgeI+EcoRI. Human NICD CDS was amplified from EF.hICN1.Ubc.GFP (Addgene Plasmid 17626) using primers 37+38 and cloned into pRAIDRS with NheI+SnaBI. For pJAZ OsJAZ$^{33}$-p53 (J-p53): an shRNA cassette targeting human TP533'-UTR was generated by annealing oligonucleotides 109+110 and cloning into pLKO.1 Puro with AgeI+EcoRI. Next, the cassette was transferred to pJAZ with EcoRI+SphI. Human p53 CDS was amplified from pLenti6/V5-p53_wt p53 (Addgene Plasmid 22945) using primers 41+42 and cloned into pJAZ with XbaI+BamHI. For pJAZ dnMAML1-NLS-GFP-OsJAZ$^{33}$ (dnM1-GFP-J): dominant-negative human MAML1 (dn-MAML1) (Yu et al., "Notch Signaling Activation in Human Embryonic Stem Cells is Required for Embryonic, but not Trophoblastic, Lineage Commitment," *Cell Stem Cell* 2:461-471 (2008), which is hereby incorporated by reference in its entirety), corresponding to MAML1 AAs 13-74, was cloned from pHAGE-N-V5-MAML1-FL (Addgene Plasmid 37048) using primers 39+40 and cloned into pJAZ NLS-GFP-OsJAZ$^{33}$ with BstBI+NheI.

Example 1—pRAIDRS Functions as an Auxin-Induced Degradation Rescue System

Figure 1B:
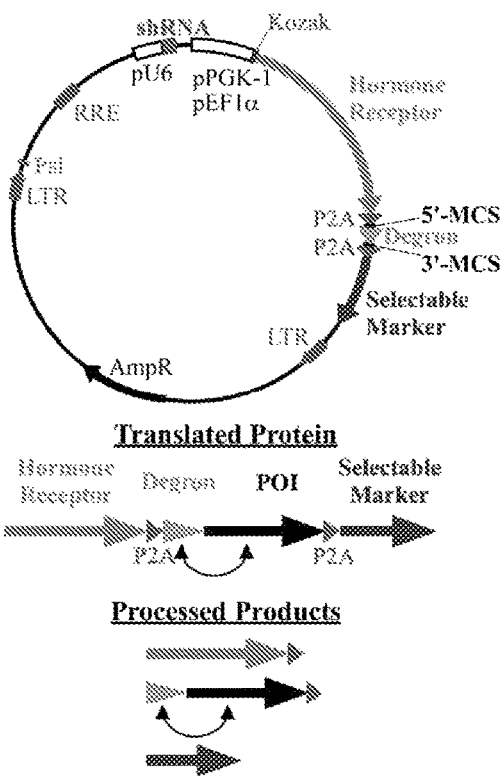

Applicants aimed to design a vector that enables depletion of an endogenous gene-of-interest and its replacement by an exogenous POI whose degradation is induced by auxin. Such an approach represents a genetic complementation (rescue) system, in which a phenotype exerted by silencing a gene-of-interest is conditionally reversed by exogenous expression of that gene product. To this end, pRAIDRS (RNAi and auxin-induced degradation rescue system), a lentiviral vector containing all elements for construction of an auxin-regulated rescue system was engineered. As depicted in FIG. 1B, a U6 promoter drives the expression of an shRNA that silences an endogenous gene-of-interest. A second promoter, either phosphoglycerate kinase-1 ("pPGK-1") or the stronger elongation factor 1α ("pEF1α") (FIG. 2A), followed by a Kozak sequence, drives the expression of an mRNA encoding three in-frame proteins separated by two porcine teschovirus-1 2A (P2A) peptides. The first protein is a codon-optimized *Oryza sativa* (rice) TIR1 auxin receptor (OsTIR1). The second component is a shortened AID degron derived from *Arabidopsis thaliana* IAA17 ("AtIAA17"), which can be fused to either terminus of the POI. The last component is a selectable marker, either puromycin N-acetyl-transferase ("PuroR") or blasticidin-S deaminase ("BSD"), conferring puromycin or blasticidin resistance, respectively. Mammalian cells transduced with pRAIDRS express OsTIR1, which associates with SKP1 and forms a functional SCF$^{TIR1}$ complex (Nishimura et al., "An Auxin-based Degron System for the Rapid Depletion of Proteins in Nonplant Cells," *Nat. Methods* 6:917-922 (2009), which is hereby incorporated by reference in its entirety). Following auxin treatment, SCF$^{TIR1}$ mediates degron polyubiquitination, leading to degradation of the POI (FIG. 1A).

Figures 2A, 2B, 2C, 2D, 2E, 2F:
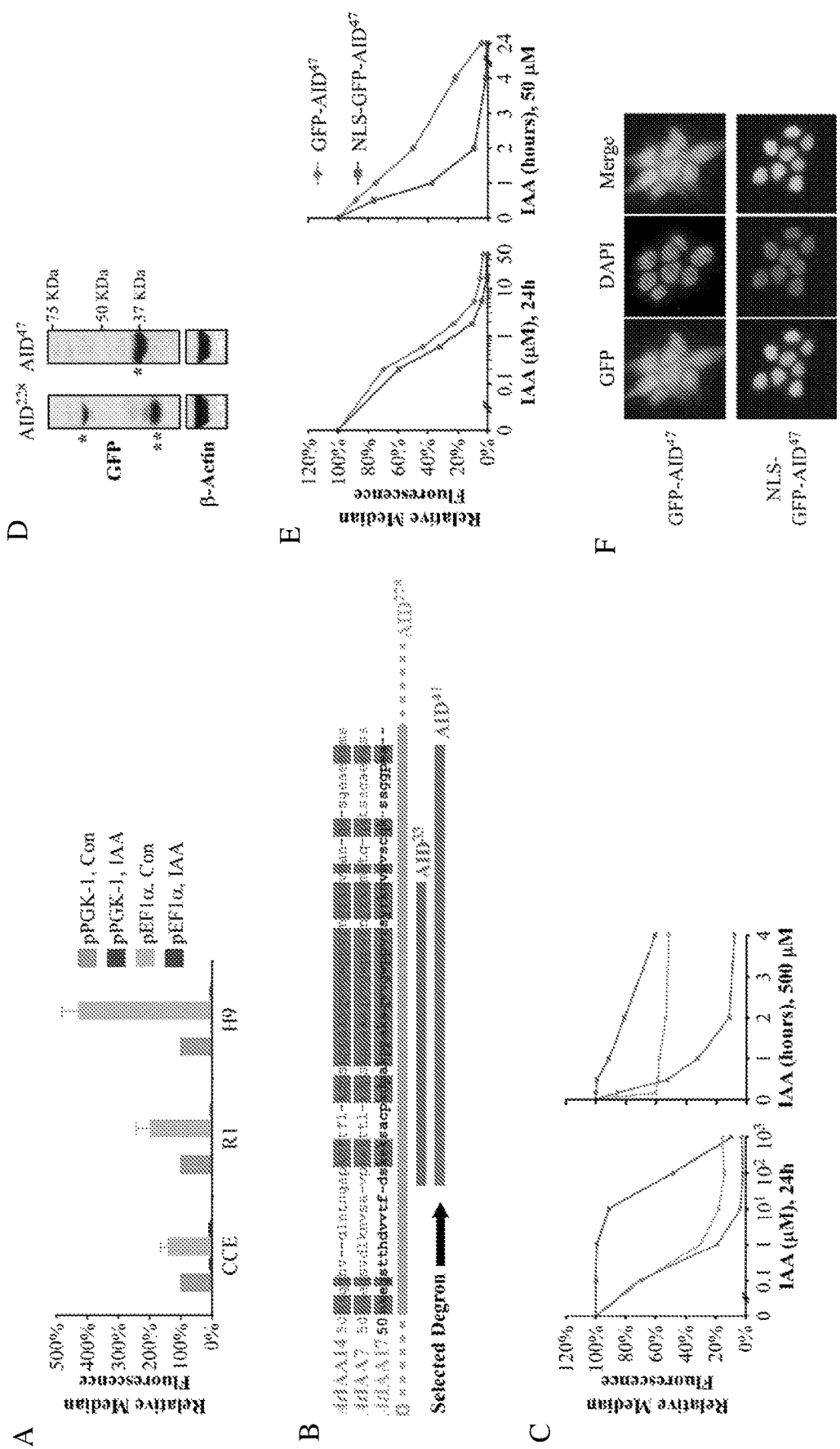
FIGS. 2A-2F show the optimization and characterization of pRAIDRS.

The full-length AtIAA17, originally used in pAID (Nishimura et al., "An Auxin-based Degron System for the Rapid Depletion of Proteins in Nonplant Cells," *Nat. Methods* 6:917-922 (2009), which is hereby incorporated by reference in its entirety), is imperfect as a degron due to its large size (228 amino acids), its propensity to confer nuclear localization (Arase et al., "IAA8 Involved in Lateral Root Formation Interacts with the TIR1 Auxin Receptor and ARF Transcription Factors in *Arabidopsis*, "*PLoS ONE* 7:e43414 (2012), which is hereby incorporated by reference in its entirety) and other potentially undesirable activities it possesses as a plant transcription factor. Therefore, the minimal required AID degron was mapped to a 47-AA region ("AID$^{47}$") spanning AtIAA17 residues 63-109 (FIGS. 2B-2C), which mostly overlaps with a previously reported shortened AID degron (Morawska et al., "An Expanded Tool Kit for the Auxin-inducible Degron System in Budding Yeast," Yeast 30:341-351 (2013), which is hereby incorporated by reference in its entirety). Notably, in pRAIDRS-transfected HEK-293T cells, green fluorescent protein ("GFP") spontaneously cleaved from the full-length AtIAA17 degron ("AID$^{228}$"), but not from AID$^{47}$ (FIGS. 2C-2D), suggesting that a shorter degron might also be more cleavage resistant. However, as other labs who have used AID$^{228}$ did not report spontaneous cleavage, this phenomenon might be cell line-specific, POI-specific or due to the vector architecture. The degradation of cytoplasmic and nuclear POIs was compared by analyzing the effect of a nuclear localization signal ("NLS") on the degradation of GFP-AID$^{47}$. The use of a NLS was found to be highly effective, but resulted in faster NLS-GFP-AID$^{47}$ degradation (FIGS. 2E-2F).

Example 2—pRAIDRS Enables Rapid and Titratable Conditional Regulation

Figures 3A, 3B, 3C, 3D:
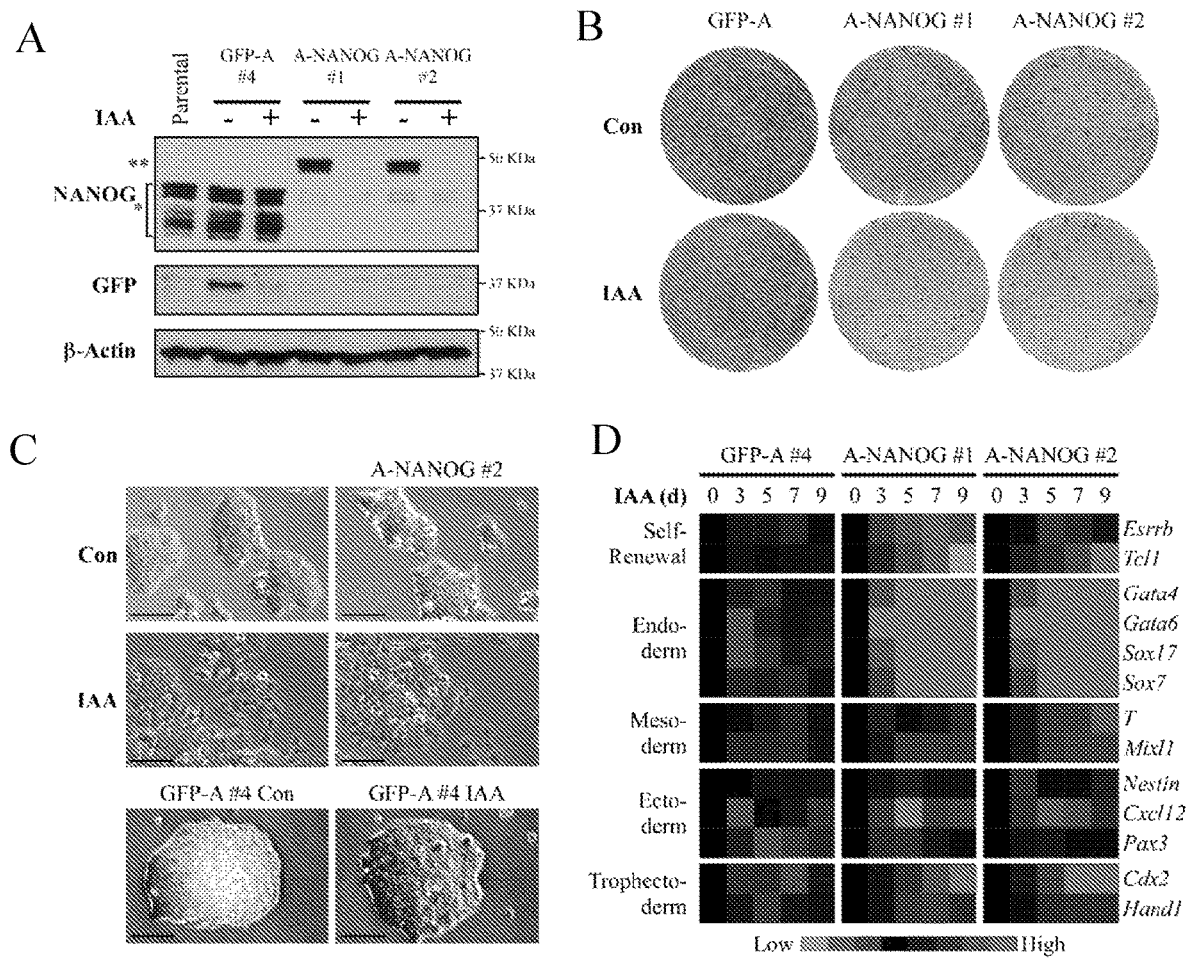
Figures 4A, 4B, 4C, 4D, 4E, 4F:
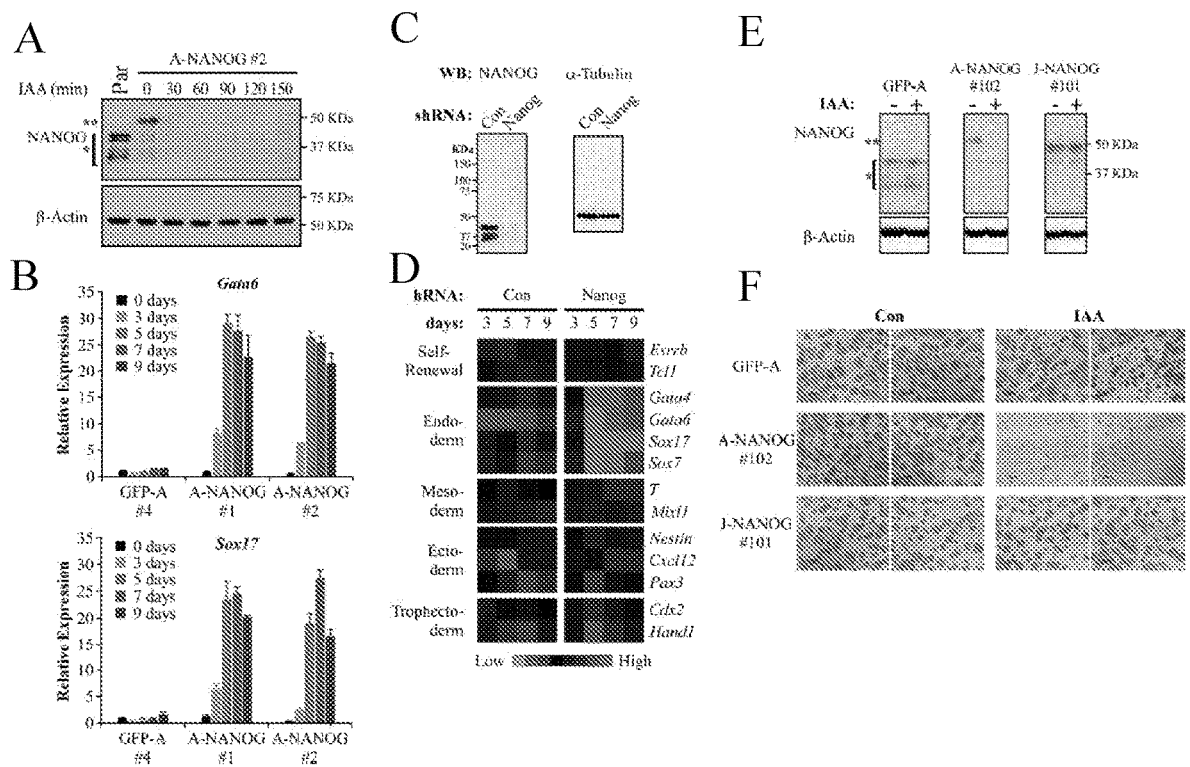
FIGS. 4A-4F illustrate an auxin-degradable NANOG rescue system in mESCs.

To demonstrate the applicability of pRAIDRS as a rescue system in mammalian stem cells, mouse ESCs ("mESCs") in which the protein level of NANOG is controlled by auxin were engineered. mESCs were infected with pRAIDRS harboring an shRNA targeting the 3'-untranslated region (3'-UTR) of Nanog mRNA and an AID$^{47}$-fused Nanog coding sequence (A-NANOG) lacking UTRs. As a control, mESCs were infected with pRAIDRS containing only GFP-AID$^{47}$ (GFP-A). Post-selection clones demonstrated effective silencing of endogenous NANOG by the shRNA, whereas exogenous A-NANOG, which was expressed at levels comparable to endogenous NANOG in control cells, was effectively and rapidly depleted following auxin treatment (FIG. 3A and FIG. 4A). Phenotypically, auxin treatment of A-NANOG mESCs, but not GFP-A mESCs, resulted in depletion of alkaline phosphatase ("AP") positive colonies, loss of ESC morphology and a transcriptional program characteristic of NANOG inactivation (Ivanova et al., "Dissecting Self-Renewal in Stem Cells with RNA Interference," Nature 442:533-538 (2006), which is hereby incorporated by reference in its entirety), namely downregulation of self-renewal genes and induction of endodermal differentiation markers (FIGS. 3B-3D and FIG. 4B). A similar transcriptional response was elicited by shRNA-mediated NANOG depletion (FIGS. 4C-4D). In contrast, mESCs infected with pRAIDRS harboring a Nanog shRNA and a Nanog coding sequence fused to an irrelevant degron (OsJAZ$^{33}$, see below) did not respond to auxin treatment (FIGS. 4E-4F). These results demonstrate the applicability of pRAIDRS as a molecular switch that facilitates dissection of protein function in mESCs.

Figures 5A, 5B, 5C, 5D, 5E, 5F:
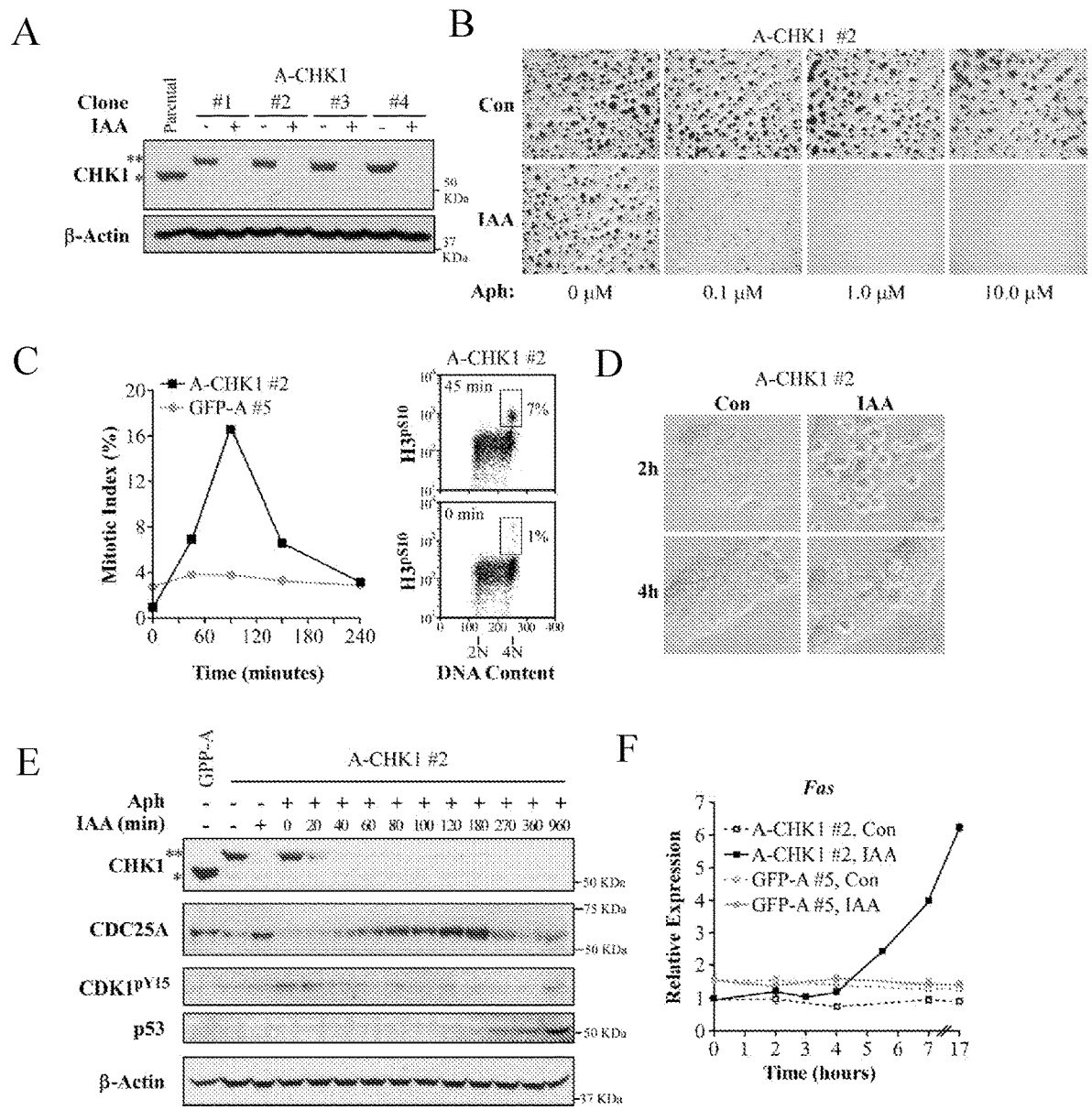
FIGS. 5A-5F show that rapid CHK1 depletion sensitizes mESCs to DNA damage.
Figures 6A, 6B, 6C, 6D, 6E:
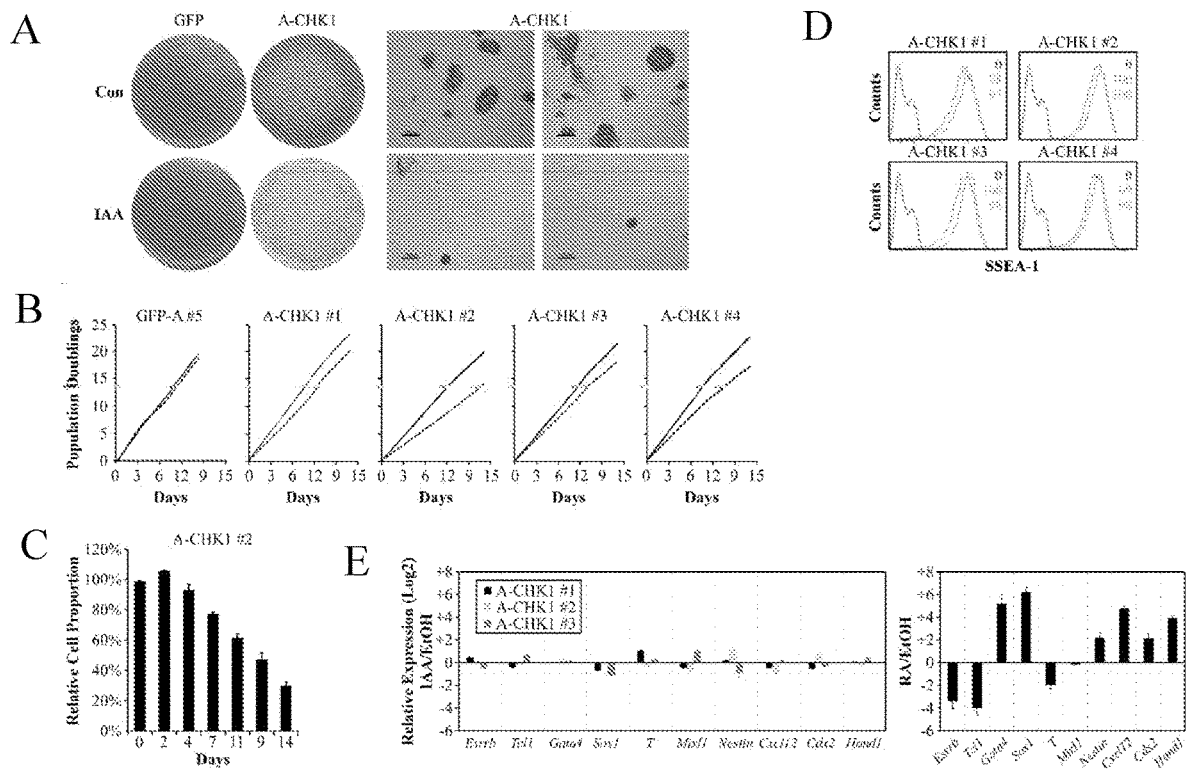
FIGS. 6A-6E show CHK1 depletion under normal growth conditions in mESCs.

To exemplify the rapidity of degradation enabled by pRAIDRS, a rescue system for the checkpoint kinase CHK1 in mESCs was established. CHK1 is required for mouse development and its disruption severely impairs DNA damage responses (Liu et al., "Chk1 is an Essential Kinase that is Regulated by Atr and Required for the G2/M DNA Damage Checkpoint," Genes Dev. 14:1448-1459 (2000) and Takai et al., "Aberrant Cell Cycle Checkpoint Function and Early Embryonic Death in Chk1(−/−) Mice," Genes Dev. 14:1439-1447 (2000), which are hereby incorporated by reference in their entirety). Multiple roles are also attributed to CHK1 in normal cell cycle progression (Enders G H, "Expanded Roles for Chk1 in Genome Maintenance," J. Biol. Chem. 283:17749-17752 (2008) and Sorensen et al., "Safeguarding Genome Integrity: The Checkpoint Kinases ATR, CHK1 and WEE1 Restrain CDK Activity During Normal DNA Replication," Nucleic Acids Res. 40:477-486 (2012), which are hereby incorporated by reference in their entirety) and in mESC self-renewal (Lee et al., "Regulation of Embryonic and Induced Pluripotency by Aurora Kinase-p53 Signaling," Cell Stem Cell 11:179-194 (2012), which is hereby incorporated by refence in its entirety). mESCs were infected with pRAIDRS harboring a Chk1 30-UTR-targeting shRNA and an AID47-fused Chk1 coding sequence ("A-CHK1"). A western blot analysis of selected clones demonstrated efficient silencing of endogenous CHK1 and complete auxin-dependent degradation of A-CHK1 (FIG. 5A). Next, A-CHK1 cells were monitored for the effects of CHK1 depletion. When cells were infected and selected in the presence or absence of auxin, a marked auxin-dependent depletion of AP-positive colonies was observed (FIG. 6A), apparently supporting the reported roles of CHK1 in mESC self-renewal. However, CHK1 depletion in post-selection cells had only a marginal effect, if any, on proliferation rate, stage specific embryonic antigen-1 ("SSEA-1") levels, mRNA expression patterns or apoptosis (FIGS. 6, 7). These data imply that the initial effect of CHK1 depletion may reflect its role during cellular stress responses induced by viral infection or drug selection.

Figures 7A, 7B, 7C, 7D, 7E, 7F, 7G:
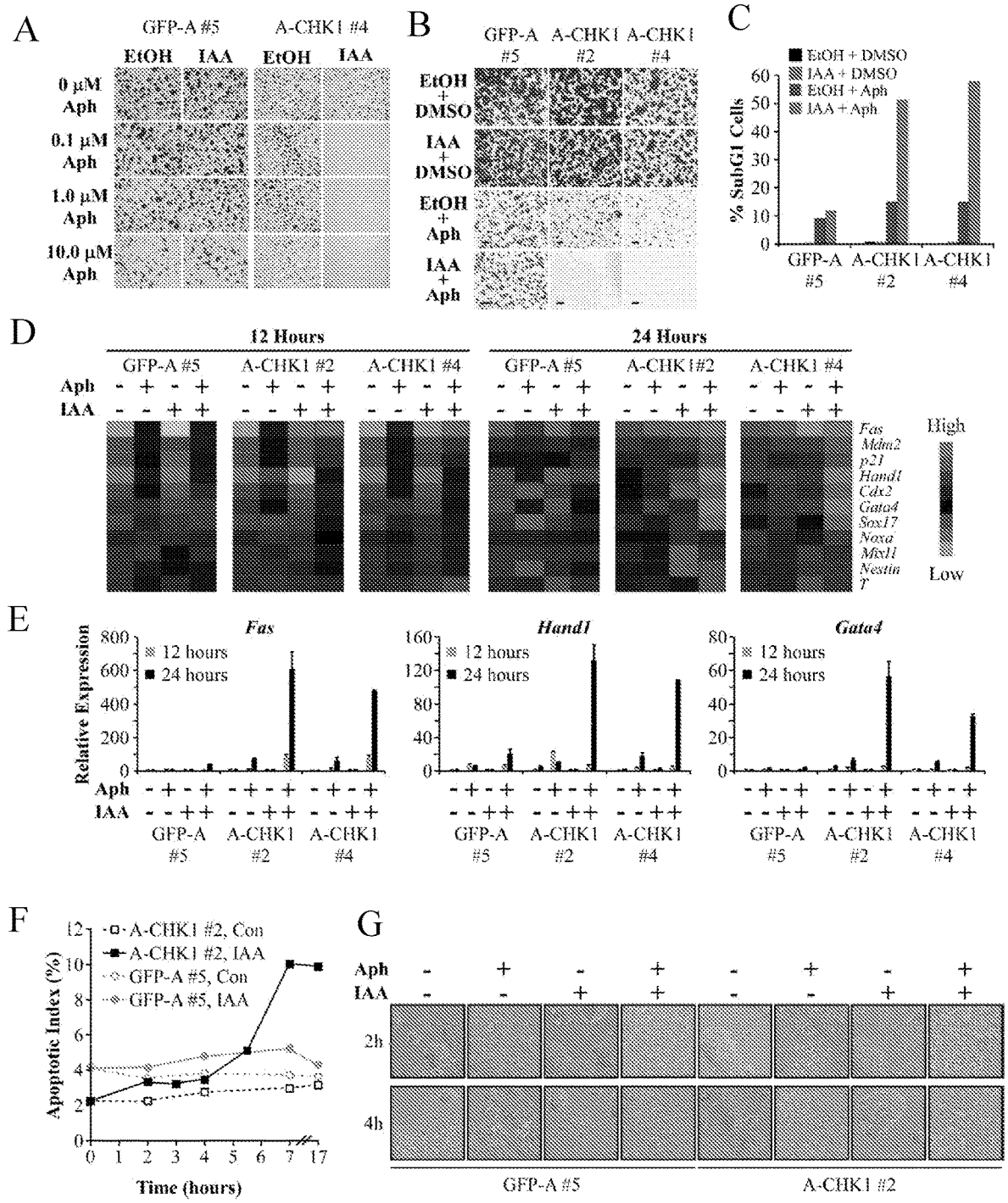
FIGS. 7A-7G show that CHK1 protects mESCs from aphidicolin-induced death and differentiation. CCE mESCs were infected with pRAIDRS A-CHK1 or GFP-A. Selected clones were analyzed for their CHK1-dependent response to aphidicolin treatment.

Next, pRAIDRS was used to study the role of CHK1 in the mESC DNA damage response. To this end, cells were treated with aphidicolin, a DNA polymerase inhibitor that induces DNA breaks and activates the ATR-CHK1 pathway (Feijoo et al., "Activation of Mammalian Chk1 During DNA Replication Arrest: A Role for Chk1 in the Intra-S Phase Checkpoint Monitoring Replication Origin Firing," J. Cell Biol. 154:913-923 (2001), which is hereby incorporated by reference in its entirety). CHK1 depletion dramatically sensitized mESCs to aphidicolin, as auxin-treated A-CHK1 cells died following treatment with 0.1 mM aphidicolin, whereas control cells survived following treatment with 100-fold higher concentrations of aphidicolin (FIG. 5B). This hypersensitivity was specific to CHK1 depletion as auxin and control-treated GFP-A cells responded indistinguishably to aphidicolin treatment (FIGS. 7A-7B). CHK1 depletion in aphidicolin-treated cells resulted in rapid induction of apoptosis, activation of a p53 ("TRP53") transcriptional response, predominantly of the p53 target Fas that encodes a death receptor (Owen-Schaub et al., "Wild-Type Human p53 and a Temperature-Sensitive Mutant Induce Fas/APO-1 Expression," Mol. Cell Biol. 15:3032-3040 (1995), which is hereby incorporated by reference in its entirety), as well as a later induction of differentiation (FIGS. 7C-7F). Applicants hypothesize that the aphidicolin susceptibility of CHK1-depleted cells stems from the ability of CHK1 to phosphorylate and induce the cytoplasmic sequestration or degradation of CDC25 phosphatases, which, in turn, augments the inhibitory Tyrl 5 phosphorylation of CDK1 ("CDK1$^{pY15}$"), preventing cell cycle progression (Boutros et al., "CDC25 Phosphatases in Cancer Cells: Key Players? Good Targets?," Nat. Rev. Cancer 7:495-507 (2007), which is hereby incorporated by reference in its entirety). Indeed, rapid (20 minutes) auxin-dependent depletion of CHK1 in aphidicolin-treated mESCs resulted in synchronous mitotic entry 45-90 minutes post-auxin treatment, paralleling CDC25A stabilization and the decrease in CDK1$^{pY15}$, and preceding p53 stabilization and the induction of Fas mRNA (FIGS. 5C-5F and FIG. 7G).

Thus, depleting CHK1 in DNA-damaged mESCs led to a series of consecutive phenotypes already observable 45 minutes post treatment. Moreover, by titrating down CHK1 levels in DNA-damaged mESCs, the applicability of pRAIDRS as a sensitive analogue tuner that enables fine-tuning of protein levels and their associated phenotypes (FIG. 8), facilitating in-depth analyses of protein dose responses was demonstrated.

Figures 9A, 9B, 9C, 9D:
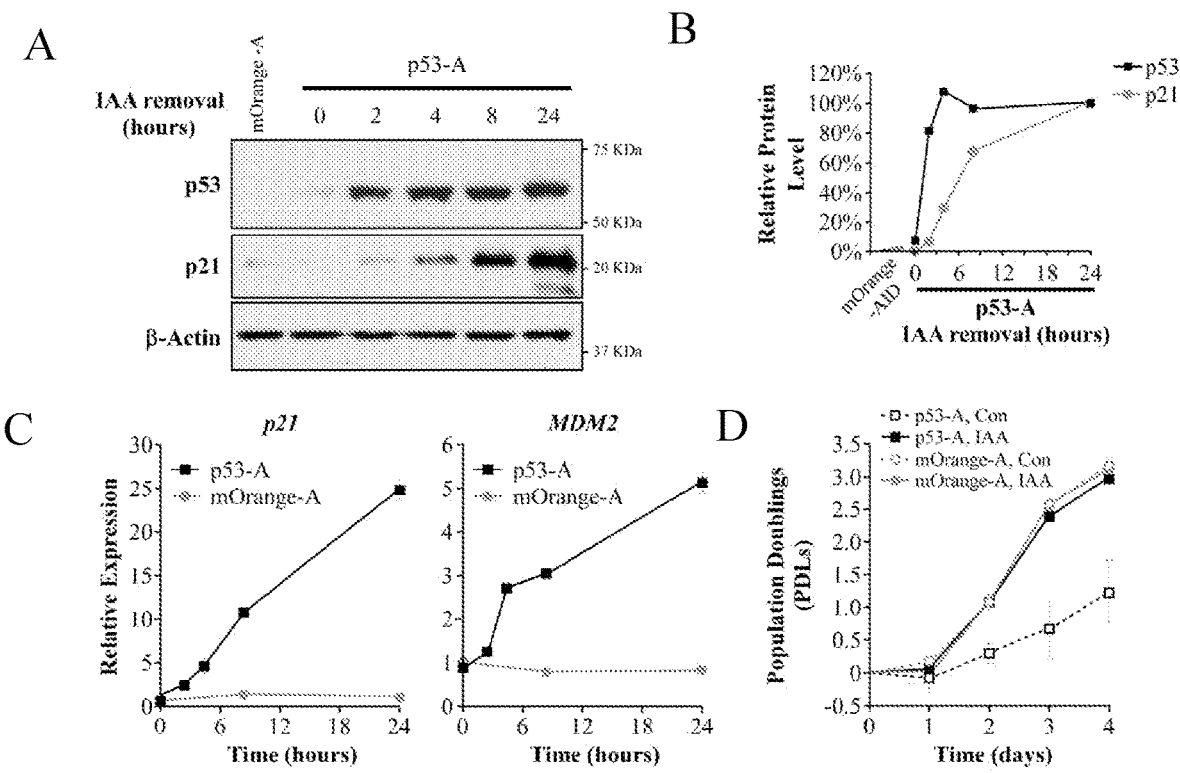
FIGS. 9A-9D show that pRAIDRS enables reversible regulation of protein level. NCI-H1299 p53-null lung adenocarcinoma cells were infected with pRAIDRS p53-AID$^{47}$ ("p53-A") or mOrange-AID$^{47}$ ("mOrange-A") as a control. Cells were maintained with 200 mM auxin, to constantly induce p53 degradation.

Auxin-induced degradation was shown to be reversible (Nishimura et al., "An Auxin-based Degron System for the Rapid Depletion of Proteins in Nonplant Cells," Nat. Methods 6:917-922 (2009), which is hereby incorporated by reference in its entirety). To demonstrate this for pRAIDRS, p53-null lung adenocarcinoma cells (NCI-H1299) expressing an auxin-degradable wild-type p53-AID47 (p53-A) were engineered. These cells were infected and cultured in the presence of auxin to prevent the stabilization of p53, known for its ability to inhibit cell growth (Brosh et al., "When Mutants Gain New Powers: News from the Mutant p53 Field," Nat. Rev. Cancer 9:701-713 (2009) and Brosh et al., "Transcriptional Control of the Proliferation Cluster by the Tumor Suppressor p53," Mol. Biosyst. 6:17-29 (2010), which are hereby incorporated by reference in their entirety). However, following auxin removal p53 was rapidly stabilized, leading to the induction of the p53 target genes p21 (CDKN1A) and MDM2, and resulting in growth retardation (FIG. 9). In sum, these data validate and exemplify pRAIDRS as an easy-to-use single-vector system enabling the construction of highly rapid, titratable, reversible and non-stressful molecular tuners in mESCs and other cell types.

Example 3—pJAZ Functions as a Coronatine-Induced Degradation Rescue System

Simultaneous conditional regulation of two proteins represents a powerful tool for complex analyses. Next, a second rescue system that harnesses the plant jasmonate-induced degradation response was engineered. As described above, in plants, isoleucine-conjugated jasmonate ("JA-Ile") mediates the binding of the F-box hormone receptor COI1 and the JAZ degron domain of target proteins, which are consequently ubiquitinated and degraded (Chini et al., "The JAZ Family of Repressors is the Missing Link in Jasmonate Signalling," Nature 448:666-671 (2007) and Owen-Schaub et al., "Wild-Type Human p53 and a Temperature-Sensitive Mutant Induce Fas/APO-1 Expression," Mol. CellBiol. 15:3032-3040 (1995), which are hereby incorporated by reference in their entirety) (FIG. 1A). Applicants believe that expression of COI1 in mammalian cells would enable hormone-dependent degradation of JAZ-fused POIs. As mammalian cells lack the pathway for JA-Ile conjugation, coronatine, a bacterial analogue of JA-Ile34 was used. Using the same architecture as pRAIDRS (FIG. 1B), pJAZ, a vector harboring a codon optimized A. thaliana COI1 receptor (AtCOI1) and a 23-amino acid JAZ degron (AtJAZ23, FIG. 10A) that was previously identified as the A. thaliana JAZ1 minimal degron motif (Sheard et al., "Jasmonate Perception by Inositol-phosphate-potentiated COI1-JAZ Co-Receptor," Nature 468:400-405 (2010), which is hereby incorporated by reference in its entirety) was constructed.

Figure 10A:
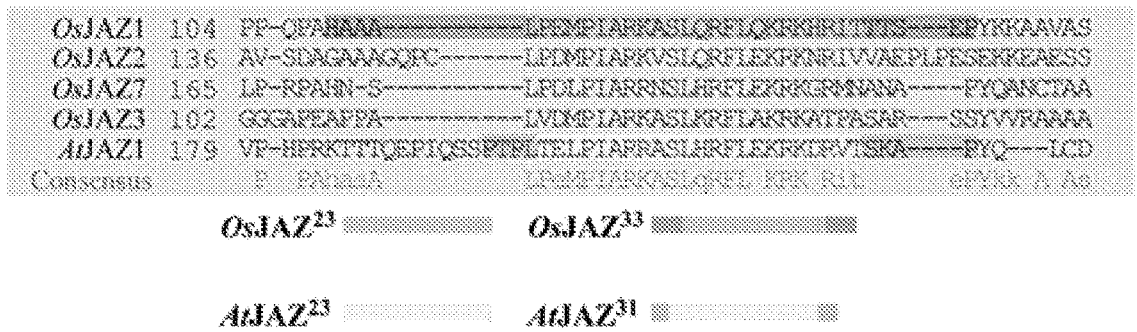
FIGS. 10A-10M shows the optimization and characterization of pJAZ.
Figure 10B:
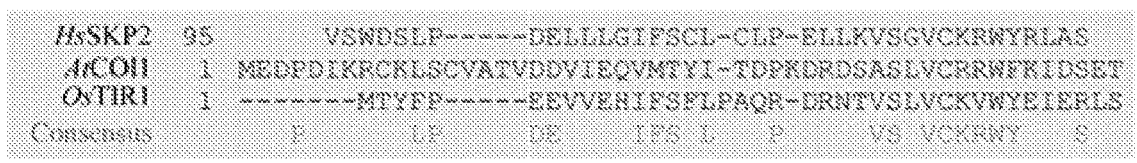
Figure 10C:
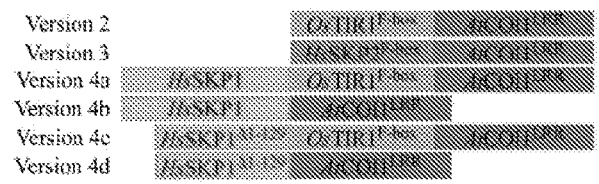
Figure 10D:
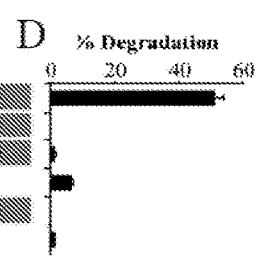
Figure 10E:
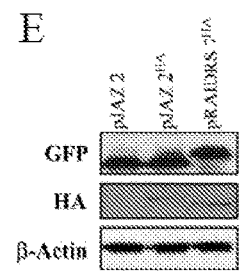
Figures 10F, 10G, 10H, 10I, 10J, 10K, 10L, 10M:
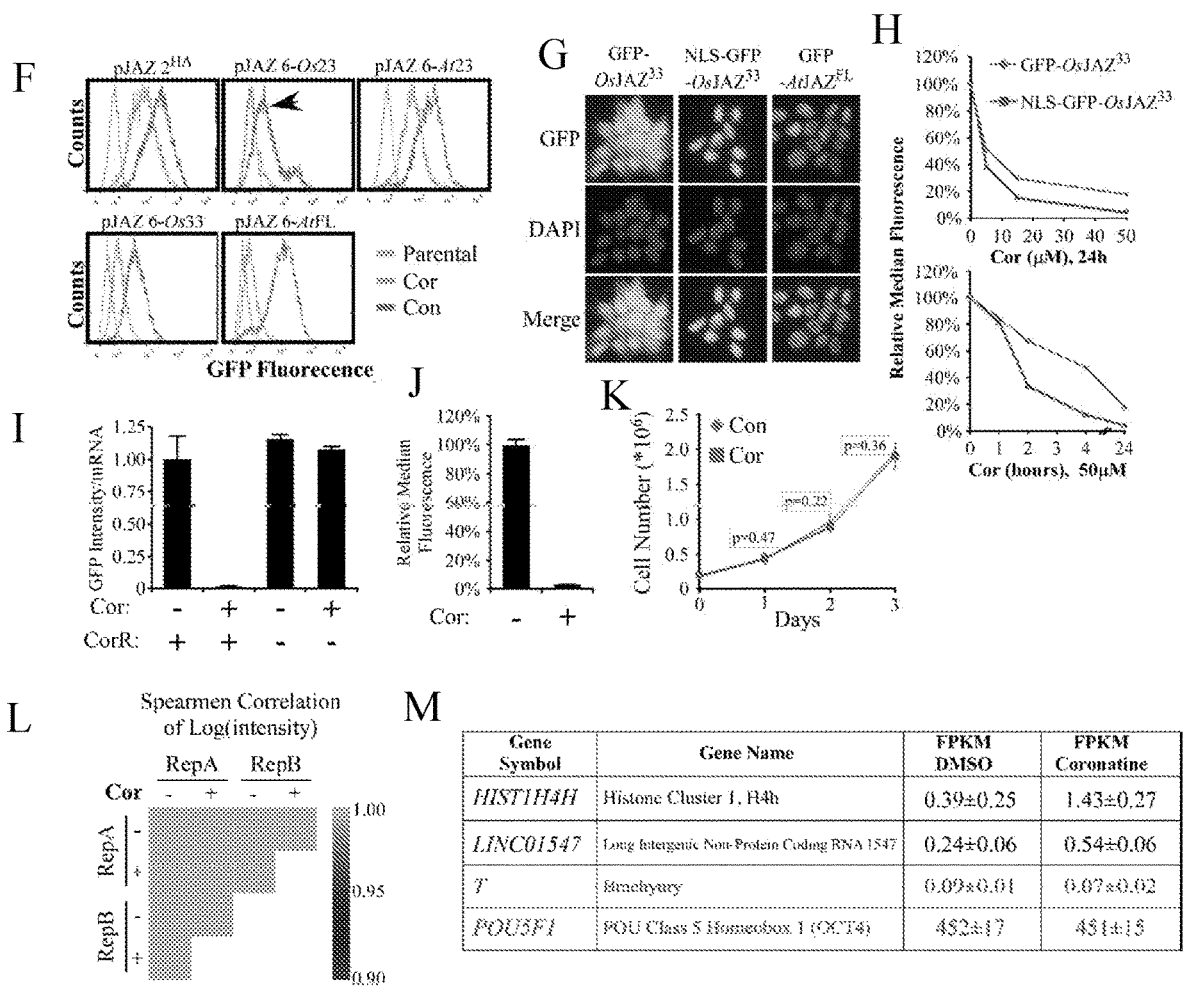
Figures 11A, 11B, 11C, 11D, 11E, 11F, 11G:
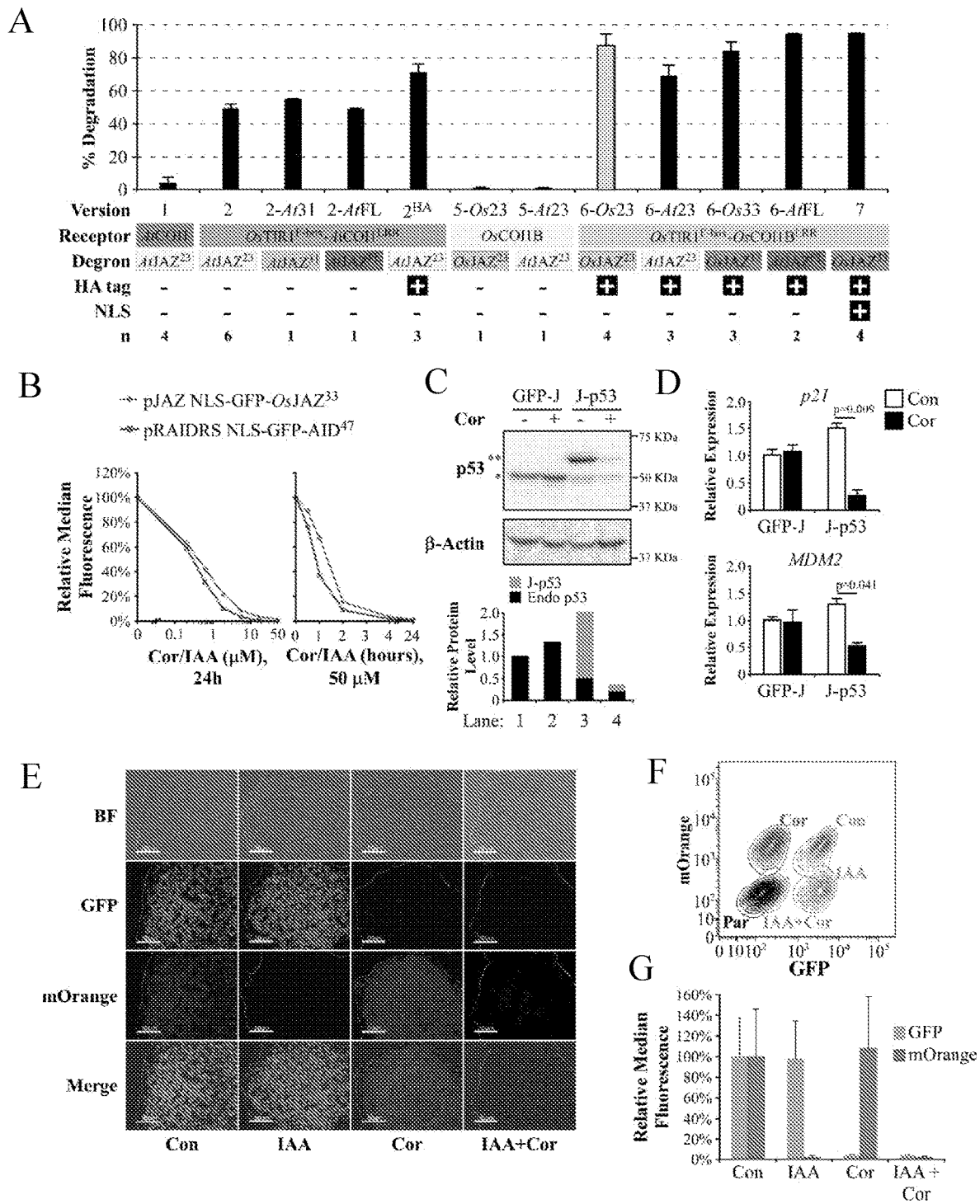
FIGS. 11A-11G illustrate a coronatine-induced degradation rescue system.
Figures 12A, 12B, 12C, 12D, 12E, 12F, 12G:
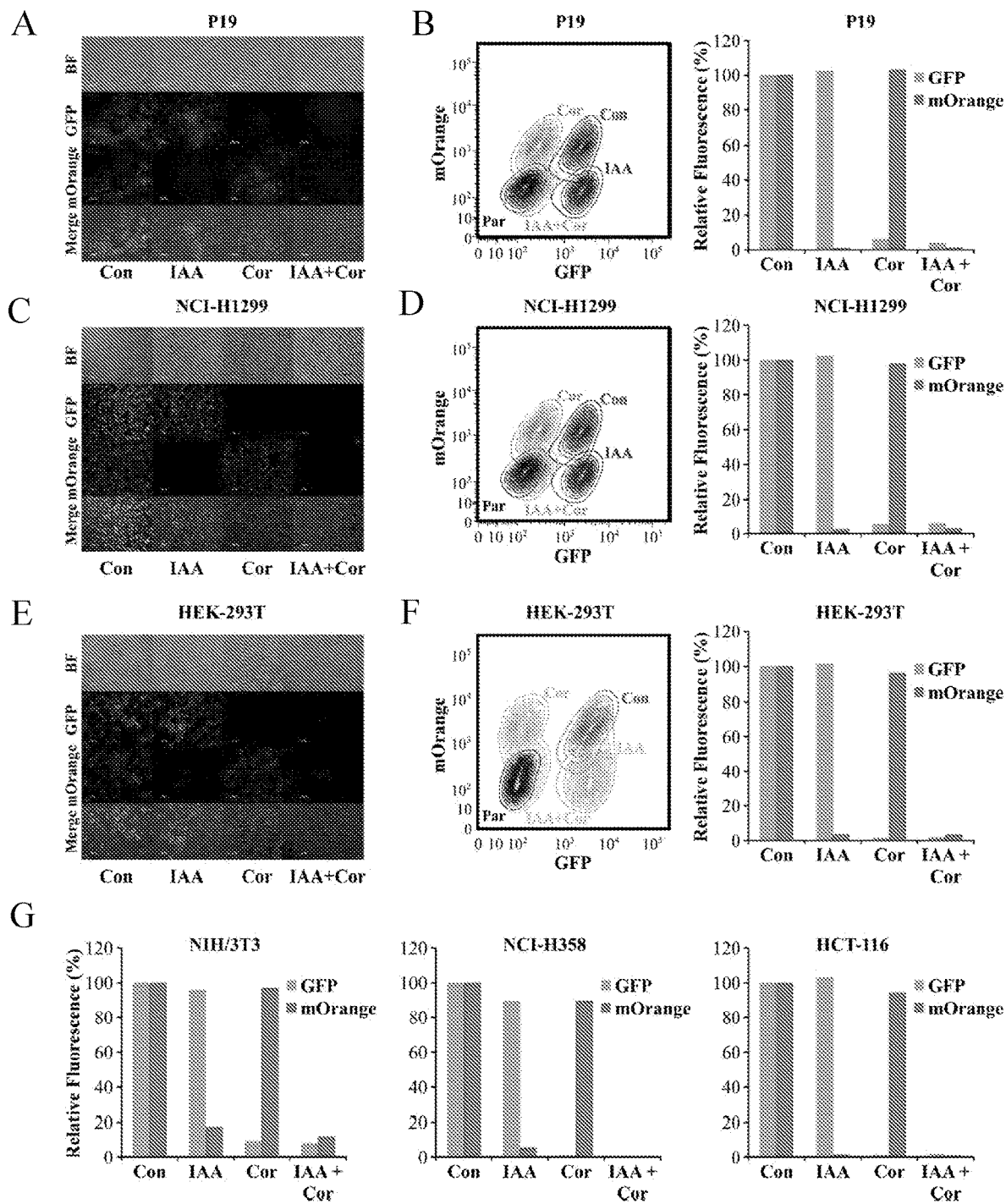
FIGS. 12A-12G show that pRAIDRS and pJAZ function independently and simultaneously in multiple cell types. P19 mouse embryonal carcinoma cells (FIGS. 12A-12B), NCI-H1299 human lung adenocarcinoma cells (FIGS. 12C-12D) and HEK-293T human embryonic kidney cells (FIGS. 12E-12F) were infected with pJAZ NLS-GFP-OsJAZ[33] (harboring PuroR) and pRAIDRS NLSmOrange-AID47 (harboring BSD) and selected with puromycin and blasticidin. Cells were treated with either EtOH and DMSO ("Con"), auxin and DMSO ("IAA"), EtOH and coronatine ("Cor"), or auxin and coronatine ("IAA+Cor"). After 24 hours, bright-field ("BF") and fluorescence microscope images were taken (FIGS. 12A, 12C, and 12E) and cells were subjected to flow cytometric fluorescence analysis (FIGS. 12B, 12D, and 12F, contour plots on the left; quantification on the right). Parental non-infected cells ("Par") for each cell type are presented as background auto-fluorescence controls.

For initial testing, HEK-293T cells were infected with pJAZ harboring GFP-AtJAZ$^{23}$ and treated with coronatine. Disappointingly, GFP degradation was extremely ineffective (FIG. 11A, version 1). pJAZ was then systematically and iteratively optimized by testing different COI1 orthologues and fusion proteins, and by altering the degron length and origin (FIG. 11A and FIGS. 10A-10M). It was hypothesized that the lack of coronatine-dependent degradation stems from insufficient binding of AtCOI1 to human SKP1 (HsSKP1). Accordingly, an OsTIR1$^{F-box}$-AtCOI1$^{LRR}$ chimera composed of OsTIR1 F-box domain (amino acids 1-39) (Tan et al., "Mechanism of Auxin Perception by the TIR1 Ubiquitin Ligase," Nature 446:640-645 (2007), which is hereby incorporated by reference in its entirety), which binds HsSKP1 effectively (Nishimura et al., "An Auxin-based Degron System for the Rapid Depletion of Proteins in Nonplant Cells," Nat. Methods 6:917-922 (2009), which is hereby incorporated by reference in its entirety), and AtCOI1 leucine-rich repeat (amino acids 52-592), the receptor region responsible for hormone and degron binding (Sheard et al., "Jasmonate Perception by Inositol-phosphate-potentiated COI1-JAZ Co-Receptor," Nature 468:400-405 (2010), which is hereby incorporated by reference in its entirety) was generated. Cells infected with pJAZ version 2 demonstrated ~50% coronatine-dependent GFP degradation. A similar chimeric receptor harboring HsSKP2$^{F-box}$ (version 3) and various AtCOI1-HsSKP1 fusions (versions 4a-d) failed to mediate coronatine-dependent degradation. Next, an extended 31-amino acid degron (AtJAZ$^{31}$), as well as AtJAZ$^{FL}$, the full-length A. thaliana JAZ1 protein were tested. Neither AtJAZ$^{31}$ nor AtJAZ$^{FL}$ enhanced pJAZ function. To test whether the OsTIR1$^{F-box}$-AtCOI1$^{LRR}$ receptor is sufficiently expressed, an amino-terminal haemagglutinin (HA) tag was added. The receptor level was found to be comparable to the level of HA-OsTIR1 in pRAIDRS-infected cells (FIG. 10E) and, hence, presumably sufficient. Unexpectedly, the HA tag boosted pJAZ efficiency to ~70% (version 2$^{HA}$), possibly by stabilizing the receptor (Morawska et al., "An Expanded Tool Kit for the Auxin-inducible Degron System in Budding Yeast," Yeast 30:341-351 (2013), which is hereby incorporated by reference in its entierty). It was next reasoned that at 37° C., a rice coronatine receptor (OsCOI1) might function better than AtCOI1, as reported for the auxin receptor (Nishimura et al., "An Auxin-based Degron System for the Rapid Depletion of Proteins in Nonplant Cells," Nat. Methods 6:917-922 (2009), which is hereby incorporated by reference in its entierty). Of the three OsCOI1 paralogues, OsCOI1B was chosen, as it binds a larger variety of JAZ proteins (Lee et al., "Oryza Sativa COI Homologues Restore Jasmonate Signal Transduction in Arabidopsis coil-1 Mutants," PLoS ONE 8:e52802 (2013), which is hereby incorporated by reference in its entiretly) and tested with either the AtJAZ23 degron or with a 23-amino acid rice degron, OsJAZ$^{23}$ (FIG. 10A). Both versions (5-At23 and 5-Os23, respectively) were found to be nonfunctional. However, a chimeric receptor (OsTIR1$^{F-box}$-OsCOI1B$^{L}$R) comprising OsTIR1 F-box domain and OsCOI1B LRR (version 6-Os23) mediated nearly 90% degradation of GFP-OsJAZ$^{23}$. Nevertheless, this version probably suffered from coronatine-independent degradation, as most cells had low fluorescence levels (FIG. 10F). Switching to AtJAZ$^{23}$ or extending the rice degron to 33 AAs (OsJAZ$^{33}$) restored GFP levels, but attenuated the effect of coronatine (versions 6-At23 and 6-Os33, respectively). Notably, using AtJAZ$^{FL}$ resulted in high GFP expression and 95% coronatine-induced degradation (version 6-AtFL), while conferring nuclear localization to GFP (FIG. 10G), in accordance with JAZ1 localization in plants (Grunewald et al., "Expression of the Arabidopsis Jasmonate Signalling Repressor JAZ1/TIFY10A is Stimulated by Auxin." EMBO Reports 10:923-928 (2009), which is hereby incorporated by reference in its entirety), prompting applicants to believe that its degron efficiency partially derives from its nuclear localization. Accordingly, GFP-OsJAZ[33] targeted to the nucleus with an NLS (version 7) was found to enhance both dose- and time-dependent coronatine-induced degradation, reaching >95% with 50 mM coronatine (FIG. 10H). Thus, a chimeric OsTIR1$^{F-box}$-OsCOI1B$^{LRR}$ receptor can effectively mediate coronatine-dependent degradation of nuclear POIs fused to an OsJAZ[33] degron without evidence of coronatine-independent degradation, coronatine receptor-independent degradation, or coronatine toxicity (FIGS. 10I-10M). Importantly, pJAZ version 7 (henceforth pJAZ) functioned nearly as well as pRAIDRS in mediating hormone-dependent degradation of nuclear GFP (FIG. 11B) and, similar to pRAIDRS, pJAZ enabled the engineering of a molecular switch in which an endogenous protein was replaced with a coronatine-regulated exogenous protein, as demonstrated by engineering a p53 switch in human ESCs (hESCs; FIGS. 11C, 11D).

Next, cells expressing coronatine-degradable NLS-GFP-OsJAZ[33] and auxin-degradable NLS-mOrange-AID[47] were engineered using pJAZ and pRAIDRS harboring PuroR or BSD, respectively, and selecting these cells with puromycin and blasticidin. Flow cytometric and microscopic analyses demonstrated that pRAIDRS and pJAZ function effectively and independently in a variety of cell types, including hESCs (FIG. 11E-11G), P19 mouse embryonal carcinoma cells, H1299 lung adenocarcinoma cells, HEK-293T cells, NIH/3T3 mouse embryonic fibroblasts, NCI-H358 human non-small cell lung cancer cells and HCT-116 human colorectal carcinoma cells (FIGS. 12A-12G). Importantly, both hormones induced 90-99% degradation, depending on the cell type, and did not show any cross-reactivity or interference, suggesting that neither system saturates the shared ubiquitination machinery. These data validate the applicability of pRAIDRS and pJAZ as a dual analogue molecular tuner.

Example 4—A Dual Molecular Switch to Dissect the NOTCH1 Pathway

Figures 13A, 13B, 13C, 13D, 13E:
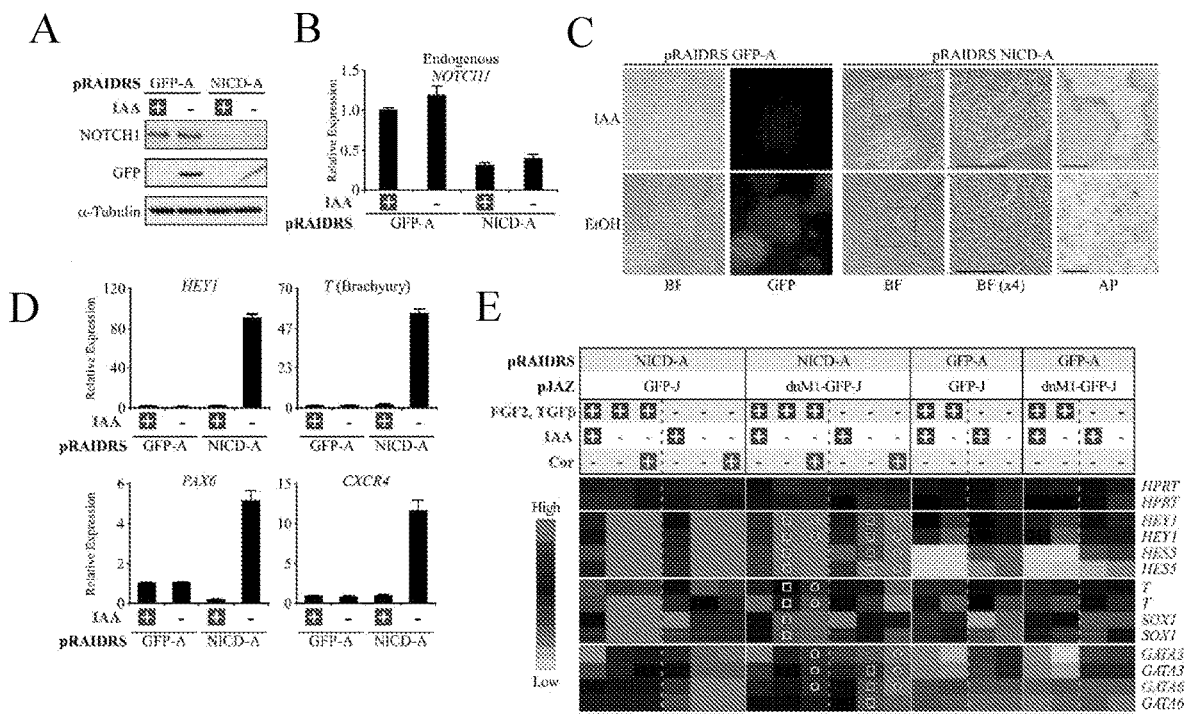
FIGS. 13A-13E illustrate a dual molecular switch to dissect NOTCH1 Function in hESCs.
Figures 14A, 14B, 14C:
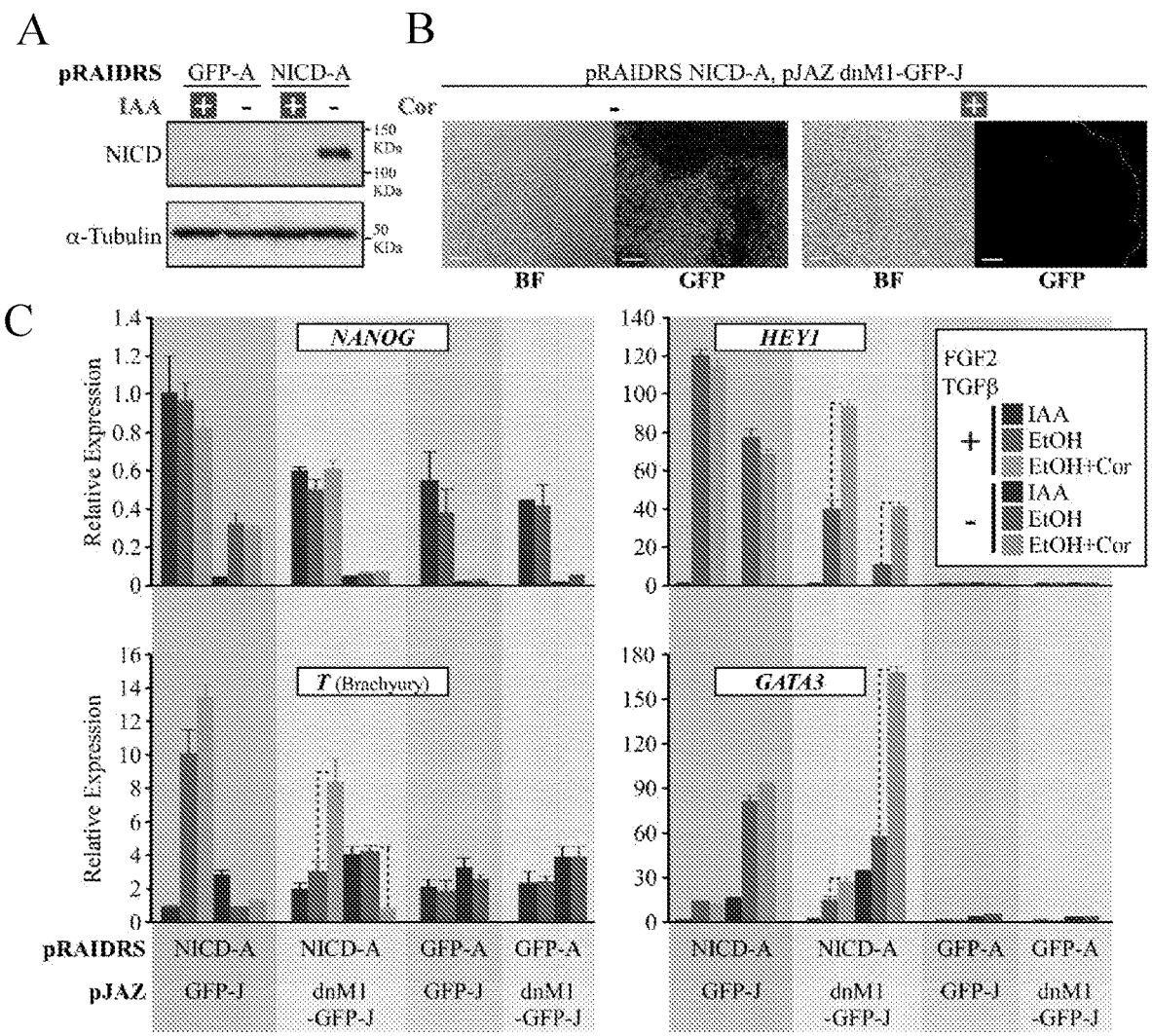
FIGS. 14A-14C illustrate a dual switch for dissection of NOTCH1 function in hESCs. H9 hESCs were infected with pRAIDRS harboring an shRNA targeting the full-length NOTCH1 receptor and an NICD-AID[47] CDS ("NICD-A"). As a control, cells were infected with pRAIDRS NLS-GFP-AID[47] ("GFP-A"). Cells were maintained with 250 µM auxin to prevent NICD-A accumulation. Following selection and isolation of colonies with ESC morphology, cells were infected with pJAZ dnMAML1-NLS-GFP-OsJAZ[33] ("dnM1-GFP-J") or pJAZ NLS-GFP-OsJAZ[33] ("GFP-J") as control and post-selection colonies were expanded.

NOTCH signaling, which is inactive in undifferentiated hESCs, participates in their differentiation into embryonic lineages (Noggle et al., "Notch Signaling is Inactive but Inducible in Human Embryonic Stem Cells," *Stem Cells* 24:1646-1653 (2006) and Yu et al., "Notch Signaling Activation in Human Embryonic Stem Cells is Required for Embryonic, but not Trophoblastic, Lineage Commitment," *Cell Stem Cell* 2:461-471 (2008), which are hereby incorporated by reference in their entirety). In mice, NOTCH was also implicated in trophectoderm formation (Rayon et al., "Notch and Hippo Converge on Cdx2 to Specify the Trophectoderm Lineage in the Mouse Blastocyst," *Dev. Cell* 30:410-422 (2014), which is hereby incorporated by reference in its entirety). Canonical NOTCH signaling involves ligand binding to the membrane receptor, leading to cleavage of the NOTCH intracellular domain ("NICD") and its translocation to the nucleus, where it binds CSL (RBPJ) and MAML1 to activate gene transcription (Andersen et al., "Non-canonical Notch Signaling: Emerging Role and Mechanism," *Trends Cell Biol.* 22:257-265 (2012), which is hereby incorporated by reference in its entirety). Applicants sought to construct a molecular switch to dissect NOTCH1 signaling in hESCs. hESCs were infected with pRAIDRS NICD-A, which harbors an shRNA targeting the full-length NOTCH1 receptor and an NICD-AID[47] CDS (FIGS. 13A-13B). These cells were maintained with auxin to prevent NICD-AID[47] accumulation, which occurs quickly following auxin removal (FIG. 14A) and induces robust differentiation (FIGS. 13C-13D). Next, these cells and their pRAIDRS GFP-A control counterparts were infected with pJAZ harboring a dominant-negative MAML1 (Yu et al., "Notch Signaling Activation in Human Embryonic Stem Cells is Required for Embryonic, but not Trophoblastic, Lineage Commitment," *Cell Stem Cell* 2:461-471 (2008), which is hereby incorporated by reference in its entirety) fused to NLS-GFP and OsJAZ[33] (dnMAML1-NLS-GFP-OsJAZ[33], abbreviated as dnM1-GFP-J), or with pJAZ NLS-GFP-OsJAZ[33] (GFP-J) as a control. Coronatine treatment effectively induced degradation of dnM1-GFP-J (FIG. 14B).

The effect of NICD-AID[47] accumulation following auxin removal in a self-renewal condition was analyzed in the presence of fibroblast growth factor 2 ("FGF2") and transforming growth factor-β (TGFβ) or in their absence (differentiation condition). As depicted in FIG. 14C and FIG. 13E, in pRAIDRS NICD-A hESCs, auxin removal led to the activation of the NOTCH targets HEY1 and HES5 in a manner largely independent of FGF2/TGFβ. However, the mesoderm marker T (Brachyury) and the ectoderm marker SOX1 were induced by NICD-A exclusively in the presence of FGF2/TGFβ, whereas the endoderm marker GATA6 and the trophectoderm marker GATA3 were induced by NICD-A primarily in the absence of FGF2/TGFβ. In nearly all cases, dnM1-GFP-J hindered NICD-A-dependent transactivation and coronatine treatment attenuated the effect of dnM1-GFP-J, restoring gene expression. Moreover, NANOG downregulation following FGF2/TGFβ withdrawal was also NICD dependent. Taken together, these data indicate that canonical NOTCH1 signaling can induce key lineage commitment transcription factors in hESCs, and that the identity of these factors depends on FGF2/TGFβ, unveiling a crosstalk between NOTCH1 signaling and the self-renewal circuitry. In addition, the induction of GATA3 implicates NOTCH1 in hESC trophectodermal differentiation. These data exemplify the applicability of pRAIDRS and pJAZ for the construction of dual molecular tuners capable of accurate dissection of signaling pathways in hESCs.

Discussion of Examples 1-4

Examples 1-4 demonstrate a molecular system that facilitates experiments that were previously unfeasible or very complicated in mammalian cells in general and ESCs in particular. Both pRAIDRS and pJAZ are easy-to-construct single vectors (FIG. 1 and FIG. 16), which deliver all the necessary elements for the construction of rapid and reversible analogue molecular tuners or, when combined, a dual tuner.

The iterative engineering of pRAIDRS and pJAZ was aimed at enhancing their functionality in ESCs. A 'hormone receptor/P2A/degron-fused POI/P2A/selectable marker' cassette that was codon optimized for human cells is transcriptionally driven by a PGK-1 or EF1a promoter. These promoters offer strong and stable expression in a wide variety of cells, with pPGK-1 being more stable in ESCs and pEF1a stronger (Norrman et al., "Quantitative Comparison of Constitutive Promoters in Human ES Cells," *PLoS ONE* 5:e12413 (2010); Xia et al., "Transgenes Delivered by Lentiviral Vector are Suppressed in Human Embryonic Stem Cells in a Promoter-dependent Manner," *Stem Cells Dev.* 16:167-176 (2007); and Qin et al., "Systematic Comparison of Constitutive Promoters and the Doxycycline-inducible Promoter," *PLoS ONE* 5:e10611 (2010), which are hereby incorporated by reference in their entirety). The P2A peptides separating the aforementioned components are the most effective 2A peptide in mammalian cells (Kim et al., "High Cleavage Efficiency of a 2A Peptide Derived from Porcine Teschovirus-1 in Human Cell Lines, Zebrafish and Mice," *PLoS ONE* 6:e18556 (2011), which is hereby incorporated by reference in its entirety). The AID degron was minimized fivefold, to reduce interference and spontaneous cleavage. To harness the jasmonate-induced degradation pathway, a chimeric receptor was engineered, as neither *A. thaliana* nor rice coronatine receptors function in mammalian cells, and identified the minimal rice JAZ degron motif compatible with this chimeric receptor. The use of selectable markers translated in-frame with the hormone receptor and POI should ensure that drug-resistant cells are hormone sensitive. Finally, the silencing of an endogenous gene-of-interest by the pU6-driven shRNA renders each lentiviral vector an independent rescue system.

A tetracycline-based complementation approach has proven useful for gene discovery and characterization in ESCs (Lee et al., "Regulation of Embryonic and Induced Pluripotency by Aurora Kinase-p53 Signaling," *Cell Stem Cell* 11:179-194 (2012); Ang et al., "Wdr5 Mediates Self-Renewal and Reprogramming Via the Embryonic Stem Cell Core Transcriptional Network," *Cell* 145:183-197 (2011); and Ivanova et al., "Dissecting Self-Renewal in Stem Cells with RNA Interference," *Nature* 442:533-538 (2006), which are hereby incorporated by reference in their entirety). Nevertheless, its slowness and the requirement for rtTA expression limit its use. Conversely, pAID enables rapid control of proteins, but does not offer endogenous gene inactivation, uses a large bioactive degron, and is inapplicable to mammalian stem cells (Table 1). Although auxin-dependent degradation was previously harnessed to generate molecular switches in somatic mammalian cells, this was achieved by sequential and laborious steps, such as TIR1 overexpression, POI-degron overexpression and gene-of-interest knockdown/out (Han et al., "Catalytic Assembly of the Mitotic Checkpoint Inhibitor BubR1-Cdc20 by a Mad2-Induced Functional Switch in Cdc20," *Mol. Cell* 51:92-104 (2013); Holland et al., "Inducible, Reversible System for the Rapid and Complete Degradation of Proteins in Mammalian Cells," *Proc. Natl. Acad. Sci. USA* 109:E3350-3357 (2012); and Rodriguez-Bravo et al., "Nuclear Pores Protect Genome Integrity by Assembling a Premitotic and Mad1-dependent Anaphase Inhibitor," *Cell* 156:1017-1031 (2014), which are hereby incorporated by reference in their entirety) or, alternatively, by genomic targeting of AID degrons to both alleles of the endogenous gene combined with TIR1 overexpression (Lambrus et al., "p53 Protects Against Genome Instability Following Centriole Duplication Failure," *J. Cell Biol.* 210:63-77 (2015), which is hereby incorporated by reference in its entirety). Although these approaches were effective in constructing single molecular tuners, the system of the present invention enables the engineering of a dual molecular tuner with unparalleled simplicity and quickness, and is particularly useful for studying ESCs, which are hard to otherwise manipulate genetically. Importantly, the rapidity of auxin-dependent protein depletion achieved with the pRAIDRS system (20-30 minutes for >95% degradation of NANOG and CHK1) is comparable with those reported by Han et al. (Han et al., "Catalytic Assembly of the Mitotic Checkpoint Inhibitor BubR1-Cdc20 by a Mad2-Induced Functional Switch in Cdc20," *Mol. Cell* 51:92-104 (2013), which is hereby incorporated by reference in its entirety) (~90 minutes), Holland et al. (Holland et al., "Inducible, Reversible System for the Rapid and Complete Degradation of Proteins in Mammalian Cells," *Proc. Natl. Acad. Sci. USA* 109:E3350-3357 (2012), which is hereby incorporated by reference in its entirety) (60-100 minutes), Rodriguez-Bravo et al. (Rodriguez-Bravo et al., "Nuclear Pores Protect Genome Integrity by Assembling a Premitotic and Mad1-dependent Anaphase Inhibitor," *Cell* 156:1017-1031 (2014), which is hereby incorporated by reference in its entirety) (>120 min) and Lambrus et al. (Lambrus et al., "p53 Protects Against Genome Instability Following Centriole Duplication Failure," *J. Cell Biol.* 210:63-77 (2015), which is hereby incorporated by reference in its entirety) (10-30 minutes) in mammalian cells.

pRAIDRS and pJAZ combine the advantages of the genetic complementation and hormone-induced degradation strategies, while averting their limitations, as each vector represents a fully functional rescue system specifically tailored to mammalian stem cells and both offer rapid, reversible and titratable control of protein levels. Importantly, combining endogenous gene silencing with conditional rescue ensures high-confidence genotype-to-phenotype causal linkages. Moreover, in contrast to other conditional protein degradation/activation systems (Bonger et al., "Small-Molecule Displacement of a Cryptic Degron Causes Conditional Protein Degradation," *Nat. Chem. Biol.* 7:531-537 (2011); Banaszynski et al., "A Rapid, Reversible, and Tunable Method to Regulate Protein Function in Living Cells Using Synthetic Small Molecules," *Cell* 126:995-1004 (2006); Neklesa et al., "Small-Molecule Hydrophobic Tagging-Induced Degradation of HaloTag Fusion Proteins," *Nat. Chem. Biol.* 7:538-543 (2011); and Braselmann et al., "A Selective Transcriptional Induction System for Mammalian Cells Based on Gal4-estrogen Receptor Fusion Proteins," *Proc. Natl. Acad. Sci. USA* 90:1657-1661 (1993), which are hereby incorporated by reference in their entirety), pRAIDRS and pJAZ degrons are extremely short, diminishing interference with POI localization and function. Other advantages of pRAIDRS and pJAZ are listed in Table 1. Of note, although both pRAIDRS and pJAZ enable hormone-dependent degradation of cytoplasmic and nuclear POIs, with both systems the degradation of nuclear POIs is faster and requires lower hormone concentrations.

As a proof-of-concept, a molecular switch for the ESC master regulator NANOG was constructed. This switch enabled conditional and nearly complete rapid depletion of NANOG, recapitulating its well-established roles in mESCs (Cavaleri et al., "Nanog: A New Recruit to the Embryonic Stem Cell Orchestra," *Cell* 113:551-552 (2003), which is hereby incorporated by reference in its entirety). By engineering a molecular switch for CHK1, a series of gene-specific phenotypes were elicited as early as 45 minutes following hormone treatment. This degree of rapidity can facilitate the distinction between primary and secondary events, and enables high-resolution kinetic studies. Furthermore, owing to the inert and specific nature of hormone-induced degradation, only minor effects were observed following CHK1 depletion in post-selection cells, contrasting with the current conception of the role of CHK1 in normal cycling cells (Enders G H, "Expanded Roles for Chk1 in Genome Maintenance," *J. Biol. Chem.* 283:17749-17752 (2008); Sorensen et al., "Safeguarding Genome Integrity: The Checkpoint Kinases ATR, CHK1 and WEE1 Restrain CDK Activity During Normal DNA Replication," *Nucleic Acids Res.* 40:477-486 (2012); and Niida et al., "Depletion of Chk1 Leads to Premature Activation of Cdc2-cyclin B and Mitotic Catastrophe," *J. Biol. Chem.* 280: 39246-39252 (2005), which are hereby incorporated by reference in their entirety) and in mESC self-renewal (Lee et al., "Regulation of Embryonic and Induced Pluripotency by Aurora Kinase-p53 Signaling," *Cell Stem Cell* 11:179-194 (2012), which is hereby incorporated by reference in its entirety). Conversely, it was demonstrated that CHK1 plays a crucial protective role in DNA-damaged mESCs by restricting mitotic entry, which otherwise leads to apoptosis or differentiation. The CHK1 molecular switch represents a unique tool for screening and characterizing CHK1 inhibitors and DNA-damage sensitizers, a rapidly growing category of anti-cancer drugs (Zhang et al., "Roles of Chk1 in Cell Biology and Cancer Therapy," *Int. J. Cancer* 134:1013-1023 (2014) and Ma et al., "Death by Releasing the Breaks: CHK1 Inhibitors as Cancer Therapeutics," *Trends Mol. Med.* 17:88-96 (2011), which are hereby incorporated by reference in their entirety).

Applicants also engineered cancer cells expressing hormone-degradable p53 and demonstrated its unleashing by auxin removal (Brosh et al., "Transcriptional Control of the Proliferation Cluster by the Tumor Suppressor p53," *Mol. Biosyst.* 6:17-29 (2010), which is hereby incorporated by reference in its entirety), highlighting the rapid reversibility of hormone-induced degradation. Stable ectopic expression of tumour suppressors is cumbersome, as cancer cells quickly evade their effects. However, effective auxin-induced p53 degradation enabled prolonged propagation of these cells without growth inhibition or transgene silencing.

Applicants further demonstrated how pRAIDRS and pJAZ allow titratable control of protein levels, a feature that enables studies of protein dose responses and threshold levels.

By engineering a coronatine-dependent p53 switch, the applicability of pJAZ for rapid and simple construction of molecular switches in hESCs was demonstrated. Moreover, applicants showed how combining pRAIDRS and pJAZ yields a dual molecular switch, where auxin and coronatine control two different proteins independently. Applying this method to hESCs, unknown aspects of the canonical NOTCH1 pathway and its integration with the hESC self-renewal network were unveiled. Thus, the generation of such dual switches (or tuners) is valuable for dissecting the function of proteins and regulatory networks.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A system for F-box hormone receptor regulated protein expression, said system comprising:
   a silencing nucleic acid molecule comprising a first promoter and an shRNA operably linked to the first promoter, wherein the shRNA silences expression of a target protein; and
   an expression nucleic acid molecule comprising a second promoter, an F-box hormone receptor operably linked to the second promoter, and a nucleic acid molecule encoding a fusion protein comprising an auxin induced degradation (AID) degron fused to the target protein, wherein the nucleic acid molecule encoding the fusion protein is operably linked to the second promoter.

2. The system of claim 1, wherein the first promoter is an RNA polymerase III promoter.

3. The system of claim 1, wherein the first promoter is a U6 promoter.

4. The system of claim 1, wherein the shRNA targets the 3'-UTR of the target protein.

5. The system of claim 1, wherein the shRNA targets a coding region of the target protein.

6. The system of claim 1, wherein the fusion protein is resistant to silencing by the shRNA.

7. The system of claim 1, wherein the second promoter is an RNA polymerase II promoter.

8. The system of claim 1, wherein the F-box hormone receptor is codon-optimized for expression in mammalian cells.

9. The system of claim 1, wherein the F-box hormone receptor is an auxin receptor.

10. The system of claim 1, wherein the F-box hormone receptor is Transport Inhibitor Response 1 (TIR1).

11. The system of claim 1, wherein the F-box hormone receptor is a chimeric F-box hormone receptor.

12. The system of claim 1, wherein the fusion protein comprises a target protein fused to the amino-terminus of the auxin induced degradation (AID) degron.

13. The system of claim 1, wherein the fusion protein comprises a target protein fused to the carboxyl-terminus of the auxin induced degradation (AID) degron.

14. The system of claim 1, wherein the expression nucleic acid molecule further encodes:
a selectable marker operably linked to the second promoter.

15. The system of claim 14, wherein the expression nucleic acid molecule further encodes:
a first self-cleaving peptide between the F-box hormone receptor and the fusion protein and a second self-cleaving peptide between the fusion protein and the selectable marker.

16. A vector comprising the system of claim 1, wherein the silencing nucleic acid molecule is coupled directly or indirectly to the expression nucleic acid molecule.

17. A mammalian cell infected with the vector of claim 16.

18. A method for F-box hormone receptor regulated protein degradation in a mammalian host cell comprising:
providing a mammalian host cell;
introducing the system of claim 1 into the mammalian host cell to produce a transgenic mammalian host cell;
culturing said transgenic mammalian host cell under conditions that result in (i) silencing expression of the target protein and (ii) expression of the fusion protein; and
contacting said transgenic mammalian host cell with a molecule that binds the F-box hormone receptor so that said fusion protein undergoes degradation.

19. A method for F-box hormone receptor regulated target protein degradation in a mammalian host cell comprising:
providing a mammalian host cell;
infecting, into the mammalian host cell, a first lentiviral vector comprising (i) a first silencing nucleic acid molecule comprising a primary first promoter and a first shRNA operably linked to the primary first promoter, wherein the first shRNA silences expression of a first target protein and (ii) a first expression nucleic acid molecule comprising a primary second promoter, a Transport Inhibitor Response 1 (TIR1) receptor operably linked to the primary second promoter, and a nucleic acid molecule encoding a first fusion protein comprising an auxin-induced degradation (AID) degron fused to a first target protein, wherein the nucleic acid molecule encoding the first fusion protein is operably linked to the primary second promoter;
infecting, into the mammalian host cell, a second lentiviral vector comprising (i) a second silencing nucleic acid molecule comprising a secondary first promoter and a second shRNA operably linked to the secondary first promoter, wherein the second shRNA silences expression of a second target protein and (ii) a second expression nucleic acid molecule comprising a secondary second promoter, a Coronatine Insensitive 1 (COI1) receptor operably linked to the secondary second promoter, and a nucleic acid molecule encoding a second fusion protein comprising a jasmonate ZIM-domain (JAZ) degron fused to a second target protein, wherein the nucleic acid molecule encoding the second fusion protein is operably linked to the secondary second promoter;
culturing said infected mammalian host cell under conditions that result in (i) silencing expression of the first and second target proteins and (ii) expression of the first and second fusion proteins;
contacting said infected mammalian host cell with a molecule that binds the TIR1 receptor so that said first fusion protein undergoes degradation; and
contacting said infected mammalian host cell with a molecule that binds the COI1 receptor so that said second fusion protein undergoes degradation.

20. The system of claim 1, wherein the auxin induced degradation (AID) degron comprises amino acids 63-109 of SEQ ID NO: 3 (AID$^{47}$).

21. The system of claim 1, wherein the auxin induced degradation (AID) degron consists of amino acids 63-109 of SEQ ID NO: 3 (AID$^{47}$).

22. The system of claim 8, wherein the F-box hormone receptor is a plant F-box hormone receptor.

* * * * *

SEQUENCE LISTING

<160> NUMBER OF SEQ ID NOS: 139

<210> SEQ ID NO 1
<211> LENGTH: 228
<212> TYPE: PRT
<213> ORGANISM: Arabidopsis thaliana

<400> SEQUENCE: 1

```
Met Asn Leu Lys Glu Thr Glu Leu Cys Leu Gly Leu Pro Gly Gly Thr
1               5                   10                  15

Glu Thr Val Glu Ser Pro Ala Lys Ser Gly Val Gly Asn Lys Arg Gly
            20                  25                  30

Phe Ser Glu Thr Val Asp Leu Lys Leu Asn Leu Gln Ser Asn Lys Gln
        35                  40                  45

Gly His Val Asp Leu Asn Thr Asn Gly Ala Pro Lys Glu Lys Thr Phe
    50                  55                  60

Leu Lys Asp Pro Ser Lys Pro Pro Ala Lys Ala Gln Val Val Gly Trp
65                  70                  75                  80

Pro Pro Val Arg Asn Tyr Arg Lys Asn Val Met Ala Asn Gln Lys Ser
                85                  90                  95

Gly Glu Ala Glu Glu Ala Met Ser Ser Gly Gly Gly Thr Val Ala Phe
            100                 105                 110

Val Lys Val Ser Met Asp Gly Ala Pro Tyr Leu Arg Lys Val Asp Leu
        115                 120                 125

Lys Met Tyr Thr Ser Tyr Lys Asp Leu Ser Asp Ala Leu Ala Lys Met
    130                 135                 140

Phe Ser Ser Phe Thr Met Gly Ser Tyr Gly Ala Gln Gly Met Ile Asp
145                 150                 155                 160

Phe Met Asn Glu Ser Lys Val Met Asp Leu Leu Asn Ser Ser Glu Tyr
                165                 170                 175

Val Pro Ser Tyr Glu Asp Lys Asp Gly Asp Trp Met Leu Val Gly Asp
            180                 185                 190

Val Pro Trp Pro Met Phe Val Glu Ser Cys Lys Arg Leu Arg Ile Met
        195                 200                 205

Lys Gly Ser Glu Ala Ile Gly Leu Ala Pro Arg Ala Met Glu Lys Phe
    210                 215                 220
```

Lys Asn Arg Ser
225

<210> SEQ ID NO 2
<211> LENGTH: 243
<212> TYPE: PRT
<213> ORGANISM: Arabidopsis thaliana

<400> SEQUENCE: 2

Met Ile Gly Gln Leu Met Asn Leu Lys Ala Thr Glu Leu Cys Leu Gly
1               5                   10                  15

Leu Pro Gly Gly Ala Glu Ala Val Glu Ser Pro Ala Lys Ser Ala Val
            20                  25                  30

Gly Ser Lys Arg Gly Phe Ser Glu Thr Val Asp Leu Met Leu Asn Leu
        35                  40                  45

Gln Ser Asn Lys Glu Gly Ser Val Asp Leu Lys Asn Val Ser Ala Val
    50                  55                  60

Pro Lys Glu Lys Thr Thr Leu Lys Asp Pro Ser Lys Pro Pro Ala Lys
65                  70                  75                  80

Ala Gln Val Val Gly Trp Pro Pro Val Arg Asn Tyr Arg Lys Asn Met
                85                  90                  95

Met Thr Gln Gln Lys Thr Ser Ser Gly Ala Glu Glu Ala Ser Ser Glu
            100                 105                 110

Lys Ala Gly Asn Phe Gly Gly Ala Ala Gly Ala Gly Leu Val Lys
        115                 120                 125

Val Ser Met Asp Gly Ala Pro Tyr Leu Arg Lys Val Asp Leu Lys Met
    130                 135                 140

Tyr Lys Ser Tyr Gln Asp Leu Ser Asp Ala Leu Ala Lys Met Phe Ser
145                 150                 155                 160

Ser Phe Thr Met Gly Asn Tyr Gly Ala Gln Gly Met Ile Asp Phe Met
                165                 170                 175

Asn Glu Ser Lys Leu Met Asn Leu Leu Asn Ser Ser Glu Tyr Val Pro
            180                 185                 190

Ser Tyr Glu Asp Lys Asp Gly Asp Trp Met Leu Val Gly Asp Val Pro
        195                 200                 205

Trp Glu Met Phe Val Glu Ser Cys Lys Arg Leu Arg Ile Met Lys Gly
    210                 215                 220

Ser Glu Ala Val Gly Leu Ala Pro Arg Ala Met Glu Lys Tyr Cys Lys
225                 230                 235                 240

Asn Arg Ser

<210> SEQ ID NO 3
<211> LENGTH: 229
<212> TYPE: PRT
<213> ORGANISM: Arabidopsis thaliana

<400> SEQUENCE: 3

Met Met Gly Ser Val Glu Leu Asn Leu Arg Glu Thr Glu Leu Cys Leu
1               5                   10                  15

Gly Leu Pro Gly Gly Asp Thr Val Ala Pro Val Thr Gly Asn Lys Arg
            20                  25                  30

Gly Phe Ser Glu Thr Val Asp Leu Lys Leu Asn Leu Asn Asn Glu Pro
        35                  40                  45

Ala Asn Lys Glu Gly Ser Thr Thr His Asp Val Val Thr Phe Asp Ser
    50                  55                  60

Lys Glu Lys Ser Ala Cys Pro Lys Asp Pro Ala Lys Pro Pro Ala Lys
65                  70                  75                  80

Ala Gln Val Val Gly Trp Pro Pro Val Arg Ser Tyr Arg Lys Asn Val
                85                  90                  95

Met Val Ser Cys Gln Lys Ser Ser Gly Gly Pro Glu Ala Ala Ala Phe
            100                 105                 110

Val Lys Val Ser Met Asp Gly Ala Pro Tyr Leu Arg Lys Ile Asp Leu
        115                 120                 125

Arg Met Tyr Lys Ser Tyr Asp Glu Leu Ser Asn Ala Leu Ser Asn Met
    130                 135                 140

Phe Ser Ser Phe Thr Met Gly Lys His Gly Gly Glu Glu Gly Met Ile
145                 150                 155                 160

Asp Phe Met Asn Glu Arg Lys Leu Met Asp Leu Val Asn Ser Trp Asp
                165                 170                 175

Tyr Val Pro Ser Tyr Glu Asp Lys Asp Gly Asp Trp Met Leu Val Gly
            180                 185                 190

Asp Val Pro Trp Pro Met Phe Val Asp Thr Cys Lys Arg Leu Arg Leu
        195                 200                 205

Met Lys Gly Ser Asp Ala Ile Gly Leu Ala Pro Arg Ala Met Glu Lys
    210                 215                 220

Cys Lys Ser Arg Ala
225

<210> SEQ ID NO 4
<211> LENGTH: 171
<212> TYPE: PRT
<213> ORGANISM: Oryza sativa

<400> SEQUENCE: 4

Met Ala Ala Ala Gly Ser Ser Arg Phe Ala Val Thr Cys Gly Leu
1               5                   10                  15

Leu Ser Gln Tyr Met Arg Glu Arg Gln Gln Pro Gln Pro Val Thr
                20                  25                  30

Val Leu Glu Ala Val Ala Glu Glu Glu Glu Asp Ala Arg Thr
            35                  40                  45

Met Gln Leu Phe Pro Pro Arg Ala Ala Ala Asp Gly Val Ala Thr
    50                  55                  60

Pro Ser Ala Gly Thr Ala Pro Leu Thr Ile Phe Tyr Asp Gly Arg Met
65                  70                  75                  80

Val Val Val Asp Asp Val Pro Val Glu Lys Ala Ala Glu Leu Met Arg
                85                  90                  95

Leu Ala Gly Ser Ala Cys Ser Pro Pro Gln Pro Ala His Ala Ala Ala
            100                 105                 110

Leu Pro Glu Met Pro Ile Ala Arg Lys Ala Ser Leu Gln Arg Phe Leu
        115                 120                 125

Gln Lys Arg Lys His Arg Ile Thr Thr Thr Ser Glu Pro Tyr Lys Lys
    130                 135                 140

Ala Ala Val Ala Ser Pro Ala Pro Glu Lys Ser Phe Ala Val Ala Pro
145                 150                 155                 160

Val Lys Asp Glu Pro Ala Thr Trp Leu Gly Leu
                165                 170

<210> SEQ ID NO 5
<211> LENGTH: 209
<212> TYPE: PRT
<213> ORGANISM: Oryza sativa

<400> SEQUENCE: 5

```
Met Ala Gly Ser Ser Glu Gln Gln Leu Val Ala Asn Ala Ala Ala Thr
1               5                   10                  15

Thr Val Ala Gly Asn Gly Ser Arg Phe Ala Val Thr Cys Gly Leu Leu
            20                  25                  30

Arg Gln Tyr Met Lys Glu His Ser Gly Ser Asn Gly Gly Gly Gly Phe
        35                  40                  45

Leu Pro Ala Val Thr Ala Met Ser Leu Met Thr Gly Gly Ala Asp Ala
    50                  55                  60

Glu Glu Glu Ala Pro Glu Val Arg Lys Thr Met Glu Leu Phe Pro Gln
65                  70                  75                  80

Gln Ala Gly Thr Leu Lys Asp Thr Gln Glu Arg Lys Glu Ile Thr Glu
                85                  90                  95

Lys Ala Gln Leu Thr Ile Phe Tyr Gly Gly Ser Val Val Phe Asp
            100                 105                 110

Asp Phe Pro Ala Glu Lys Ala Gly Glu Leu Met Lys Leu Ala Gly Ser
        115                 120                 125

Arg Asp Ser Thr Ala Ala Ala Val Ser Asp Ala Gly Ala Ala Ala
130                 135                 140

Gly Gln Pro Cys Leu Pro Asp Met Pro Ile Ala Arg Lys Val Ser Leu
145                 150                 155                 160

Gln Arg Phe Leu Glu Lys Arg Lys Asn Arg Ile Val Val Ala Glu Pro
                165                 170                 175

Leu Pro Glu Ser Glu Lys Lys Glu Ala Glu Ser Ser Lys Arg Ala Lys
            180                 185                 190

Lys Asp Asp Gly Gly Ala Ser Trp Leu Gln Val Asn Pro Thr Leu Ser
        195                 200                 205

Leu
```

<210> SEQ ID NO 6
<211> LENGTH: 232
<212> TYPE: PRT
<213> ORGANISM: Oryza sativa

<400> SEQUENCE: 6

```
Met Ala Gly Arg Ala Thr Ala Thr Ala Thr Ala Gly Lys Asp Arg
1               5                   10                  15

Ser Ser Phe Ala Val Thr Cys Ser Leu Leu Ser Gln Phe Leu Lys Glu
            20                  25                  30

Lys Lys Gly Gly Gly Gly Leu Gln Gly Leu Gly Leu Gly Leu Arg
        35                  40                  45

Pro Ala Pro Ala Ala Pro Pro Ala Ala Gly Ala Gly Gly Ala Phe Arg
    50                  55                  60

Pro Pro Pro Thr Thr Met Asn Leu Leu Ser Gly Leu Asp Ala Pro Ala
65                  70                  75                  80

Val Glu Val Glu Pro Asn Thr Ala Glu Ala Ala Asp Glu Leu Pro
                85                  90                  95

Leu Ile Lys Ala Pro Ala Asp Gln Gln Ser Asp Glu Ser Ala Ser Glu
            100                 105                 110

Ala Ala Gly Glu Lys Ala Gln Gln Leu Thr Ile Phe Tyr Gly Gly Lys
        115                 120                 125

Val Val Val Phe Glu Asn Phe Pro Ser Thr Lys Val Lys Asp Leu Leu
    130                 135                 140
```

Gln Ile Val Ser Thr Gly Asp Gly Val Asp Lys Asn Thr Gly Thr Ala
145                 150                 155                 160

Ala Thr Gln Ser Leu Pro Arg Pro Ala His Asn Ser Leu Pro Asp Leu
            165                 170                 175

Pro Ile Ala Arg Arg Asn Ser Leu His Arg Phe Leu Glu Lys Arg Lys
        180                 185                 190

Gly Arg Met Asn Ala Asn Ala Pro Tyr Gln Ala Asn Cys Thr Ala Ala
    195                 200                 205

Pro Ser Lys Gln Ala Asn Gly Asp Lys Ser Trp Leu Gly Phe Gly Gln
210                 215                 220

Glu Met Thr Ile Lys Gln Glu Ile
225                 230

<210> SEQ ID NO 7
<211> LENGTH: 179
<212> TYPE: PRT
<213> ORGANISM: Oryza sativa

<400> SEQUENCE: 7

Met Ala Ser Thr Asp Pro Met Thr Arg Arg Phe Ala Val Ala Cys Gly
1               5                   10                  15

Val Leu Ser Gln Tyr Val Lys Ala Asn Ser Ser Gln Pro Ser Thr Ala
            20                  25                  30

Ala Pro Val Ala Gln Gly Val Ser Gly Leu Met Ala Ala Ala Ala Ala
        35                  40                  45

Ala Ala Ala Ala Pro Val Val Gln Glu Pro Gly Cys Glu Val Asp Gly
    50                  55                  60

Gly Gly Gln Gln Phe Thr Ile Phe Tyr Ala Gly Lys Val Val Val Ile
65                  70                  75                  80

Asp Arg Cys Thr Pro Ala Met Ala Ala Glu Leu Met Arg Phe Ala Ser
                85                  90                  95

Ala Ala Gln Gly Gly Gly Gly Ala Pro Glu Ala Pro Pro Ala Leu Val
            100                 105                 110

Asp Met Pro Ile Ala Arg Lys Ala Ser Leu Lys Arg Phe Leu Ala Lys
        115                 120                 125

Arg Lys Ala Thr Pro Ala Ser Ala Arg Ser Ser Tyr Val Val Arg Ala
    130                 135                 140

Ala Ala Ala Glu Glu Gln Pro Pro Ala Lys Lys Ala Lys Ala Ala
145                 150                 155                 160

Val Glu Arg Arg Glu Asp Trp Leu Ala Leu Gly Ser Leu Gly His Met
                165                 170                 175

His Ser Arg

<210> SEQ ID NO 8
<211> LENGTH: 253
<212> TYPE: PRT
<213> ORGANISM: Arabidopsis thaliana

<400> SEQUENCE: 8

Met Ser Ser Ser Met Glu Cys Ser Glu Phe Val Gly Ser Arg Arg Phe
1               5                   10                  15

Thr Gly Lys Lys Pro Ser Phe Ser Gln Thr Cys Ser Arg Leu Ser Gln
            20                  25                  30

Tyr Leu Lys Glu Asn Gly Ser Phe Gly Asp Leu Ser Leu Gly Met Ala
        35                  40                  45

Cys Lys Pro Asp Val Asn Gly Thr Leu Gly Asn Ser Arg Gln Pro Thr

```
            50                  55                  60
Thr Thr Met Ser Leu Phe Pro Cys Glu Ala Ser Asn Met Asp Ser Met
 65                  70                  75                  80

Val Gln Asp Val Lys Pro Thr Asn Leu Phe Pro Arg Gln Pro Ser Phe
                     85                  90                  95

Ser Ser Ser Ser Ser Ser Leu Pro Lys Glu Asp Val Leu Lys Met Thr
                100                 105                 110

Gln Thr Thr Arg Ser Val Lys Pro Glu Ser Gln Thr Ala Pro Leu Thr
                115                 120                 125

Ile Phe Tyr Ala Gly Gln Val Ile Val Phe Asn Asp Phe Ser Ala Glu
            130                 135                 140

Lys Ala Lys Glu Val Ile Asn Leu Ala Ser Lys Gly Thr Ala Asn Ser
145                 150                 155                 160

Leu Ala Lys Asn Gln Thr Asp Ile Arg Ser Asn Ile Ala Thr Ile Ala
                165                 170                 175

Asn Gln Val Pro His Pro Arg Lys Thr Thr Thr Gln Glu Pro Ile Gln
                180                 185                 190

Ser Ser Pro Thr Pro Leu Thr Glu Leu Pro Ile Ala Arg Arg Ala Ser
                195                 200                 205

Leu His Arg Phe Leu Glu Lys Arg Lys Asp Arg Val Thr Ser Lys Ala
            210                 215                 220

Pro Tyr Gln Leu Cys Asp Pro Ala Lys Ala Ser Ser Asn Pro Gln Thr
225                 230                 235                 240

Thr Gly Asn Met Ser Trp Leu Gly Leu Ala Ala Glu Ile
                245                 250

<210> SEQ ID NO 9
<211> LENGTH: 424
<212> TYPE: PRT
<213> ORGANISM: Homo sapiens

<400> SEQUENCE: 9

Met His Arg Lys His Leu Gln Glu Ile Pro Asp Leu Ser Ser Asn Val
 1               5                  10                  15

Ala Thr Ser Phe Thr Trp Gly Trp Asp Ser Ser Lys Thr Ser Glu Leu
                 20                  25                  30

Leu Ser Gly Met Gly Val Ser Ala Leu Glu Lys Glu Glu Pro Asp Ser
                 35                  40                  45

Glu Asn Ile Pro Gln Glu Leu Leu Ser Asn Leu Gly His Pro Glu Ser
 50                  55                  60

Pro Pro Arg Lys Arg Leu Lys Ser Lys Gly Ser Asp Lys Asp Phe Val
 65                  70                  75                  80

Ile Val Arg Arg Pro Lys Leu Asn Arg Glu Asn Phe Pro Gly Val Ser
                 85                  90                  95

Trp Asp Ser Leu Pro Asp Glu Leu Leu Leu Gly Ile Phe Ser Cys Leu
                100                 105                 110

Cys Leu Pro Glu Leu Leu Lys Val Ser Gly Val Cys Lys Arg Trp Tyr
                115                 120                 125

Arg Leu Ala Ser Asp Glu Ser Leu Trp Gln Thr Leu Asp Leu Thr Gly
            130                 135                 140

Lys Asn Leu His Pro Asp Val Thr Gly Arg Leu Leu Ser Gln Gly Val
145                 150                 155                 160

Ile Ala Phe Arg Cys Pro Arg Ser Phe Met Asp Gln Pro Leu Ala Glu
                165                 170                 175
```

```
His Phe Ser Pro Phe Arg Val Gln His Met Asp Leu Ser Asn Ser Val
            180                 185                 190

Ile Glu Val Ser Thr Leu His Gly Ile Leu Ser Gln Cys Ser Lys Leu
        195                 200                 205

Gln Asn Leu Ser Leu Glu Gly Leu Arg Leu Ser Asp Pro Ile Val Asn
    210                 215                 220

Thr Leu Ala Lys Asn Ser Asn Leu Val Arg Leu Asn Leu Ser Gly Cys
225                 230                 235                 240

Ser Gly Phe Ser Glu Phe Ala Leu Gln Thr Leu Leu Ser Ser Cys Ser
                245                 250                 255

Arg Leu Asp Glu Leu Asn Leu Ser Trp Cys Phe Asp Phe Thr Glu Lys
            260                 265                 270

His Val Gln Val Ala Val Ala His Val Ser Glu Thr Ile Thr Gln Leu
        275                 280                 285

Asn Leu Ser Gly Tyr Arg Lys Asn Leu Gln Lys Ser Asp Leu Ser Thr
    290                 295                 300

Leu Val Arg Arg Cys Pro Asn Leu Val His Leu Asp Leu Ser Asp Ser
305                 310                 315                 320

Val Met Leu Lys Asn Asp Cys Phe Gln Glu Phe Phe Gln Leu Asn Tyr
                325                 330                 335

Leu Gln His Leu Ser Leu Ser Arg Cys Tyr Asp Ile Ile Pro Glu Thr
            340                 345                 350

Leu Leu Glu Leu Gly Glu Ile Pro Thr Leu Lys Thr Leu Gln Val Phe
        355                 360                 365

Gly Ile Val Pro Asp Gly Thr Leu Gln Leu Leu Lys Glu Ala Leu Pro
    370                 375                 380

His Leu Gln Ile Asn Cys Ser His Phe Thr Thr Ile Ala Arg Pro Thr
385                 390                 395                 400

Ile Gly Asn Lys Lys Asn Gln Glu Ile Trp Gly Ile Lys Cys Arg Leu
                405                 410                 415

Thr Leu Gln Lys Pro Ser Cys Leu
            420

<210> SEQ ID NO 10
<211> LENGTH: 592
<212> TYPE: PRT
<213> ORGANISM: Arabidopsis thaliana

<400> SEQUENCE: 10

Met Glu Asp Pro Asp Ile Lys Arg Cys Lys Leu Ser Cys Val Ala Thr
1               5                   10                  15

Val Asp Asp Val Ile Glu Gln Val Met Thr Tyr Ile Thr Asp Pro Lys
                20                  25                  30

Asp Arg Asp Ser Ala Ser Leu Val Cys Arg Arg Trp Phe Lys Ile Asp
            35                  40                  45

Ser Glu Thr Arg Glu His Val Thr Met Ala Leu Cys Tyr Thr Ala Thr
        50                  55                  60

Pro Asp Arg Leu Ser Arg Arg Phe Pro Asn Leu Arg Ser Leu Lys Leu
65                  70                  75                  80

Lys Gly Lys Pro Arg Ala Ala Met Phe Asn Leu Ile Pro Glu Asn Trp
                85                  90                  95

Gly Gly Tyr Val Thr Pro Trp Val Thr Glu Ile Ser Asn Asn Leu Arg
            100                 105                 110

Gln Leu Lys Ser Val His Phe Arg Arg Met Ile Val Ser Asp Leu Asp
        115                 120                 125
```

```
Leu Asp Arg Leu Ala Lys Ala Arg Ala Asp Leu Glu Thr Leu Lys
    130                 135                 140

Leu Asp Lys Cys Ser Gly Phe Thr Thr Asp Gly Leu Leu Ser Ile Val
145                 150                 155                 160

Thr His Cys Arg Lys Ile Lys Thr Leu Leu Met Glu Glu Ser Ser Phe
                165                 170                 175

Ser Glu Lys Asp Gly Lys Trp Leu His Glu Leu Ala Gln His Asn Thr
                180                 185                 190

Ser Leu Glu Val Leu Asn Phe Tyr Met Thr Glu Phe Ala Lys Ile Ser
            195                 200                 205

Pro Lys Asp Leu Glu Thr Ile Ala Arg Asn Cys Arg Ser Leu Val Ser
    210                 215                 220

Val Lys Val Gly Asp Phe Glu Ile Leu Glu Leu Val Gly Phe Phe Lys
225                 230                 235                 240

Ala Ala Ala Asn Leu Glu Glu Phe Cys Gly Gly Ser Leu Asn Glu Asp
                245                 250                 255

Ile Gly Met Pro Glu Lys Tyr Met Asn Leu Val Phe Pro Arg Lys Leu
                260                 265                 270

Cys Arg Leu Gly Leu Ser Tyr Met Gly Pro Asn Glu Met Pro Ile Leu
            275                 280                 285

Phe Pro Phe Ala Ala Gln Ile Arg Lys Leu Asp Leu Leu Tyr Ala Leu
    290                 295                 300

Leu Glu Thr Glu Asp His Cys Thr Leu Ile Gln Lys Cys Pro Asn Leu
305                 310                 315                 320

Glu Val Leu Glu Thr Arg Asn Val Ile Gly Asp Arg Gly Leu Glu Val
                325                 330                 335

Leu Ala Gln Tyr Cys Lys Gln Leu Lys Arg Leu Arg Ile Glu Arg Gly
            340                 345                 350

Ala Asp Glu Gln Gly Met Glu Asp Glu Glu Gly Leu Val Ser Gln Arg
    355                 360                 365

Gly Leu Ile Ala Leu Ala Gln Gly Cys Gln Glu Leu Glu Tyr Met Ala
370                 375                 380

Val Tyr Val Ser Asp Ile Thr Asn Glu Ser Leu Glu Ser Ile Gly Thr
385                 390                 395                 400

Tyr Leu Lys Asn Leu Cys Asp Phe Arg Leu Val Leu Leu Asp Arg Glu
                405                 410                 415

Glu Arg Ile Thr Asp Leu Pro Leu Asp Asn Gly Val Arg Ser Leu Leu
                420                 425                 430

Ile Gly Cys Lys Lys Leu Arg Arg Phe Ala Phe Tyr Leu Arg Gln Gly
            435                 440                 445

Gly Leu Thr Asp Leu Gly Leu Ser Tyr Ile Gly Gln Tyr Ser Pro Asn
    450                 455                 460

Val Arg Trp Met Leu Leu Gly Tyr Val Gly Glu Ser Asp Glu Gly Leu
465                 470                 475                 480

Met Glu Phe Ser Arg Gly Cys Pro Asn Leu Gln Lys Leu Glu Met Arg
                485                 490                 495

Gly Cys Cys Phe Ser Glu Arg Ala Ile Ala Ala Val Thr Lys Leu
                500                 505                 510

Pro Ser Leu Arg Tyr Leu Trp Val Gln Gly Tyr Arg Ala Ser Met Thr
            515                 520                 525

Gly Gln Asp Leu Met Gln Met Ala Arg Pro Tyr Trp Asn Ile Glu Leu
    530                 535                 540
```

```
Ile Pro Ser Arg Arg Val Pro Glu Val Asn Gln Gln Gly Glu Ile Arg
545                 550                 555                 560

Glu Met Glu His Pro Ala His Ile Leu Ala Tyr Tyr Ser Leu Ala Gly
            565                 570                 575

Gln Arg Thr Asp Cys Pro Thr Thr Val Arg Val Leu Lys Glu Pro Ile
            580                 585                 590

<210> SEQ ID NO 11
<211> LENGTH: 575
<212> TYPE: PRT
<213> ORGANISM: Oryza sativa

<400> SEQUENCE: 11

Met Thr Tyr Phe Pro Glu Glu Val Val Glu His Ile Phe Ser Phe Leu
1               5                   10                  15

Pro Ala Gln Arg Asp Arg Asn Thr Val Ser Leu Val Cys Lys Val Trp
            20                  25                  30

Tyr Glu Ile Glu Arg Leu Ser Arg Arg Gly Val Phe Val Gly Asn Cys
        35                  40                  45

Tyr Ala Val Arg Ala Gly Arg Val Ala Ala Arg Phe Pro Asn Val Arg
50                  55                  60

Ala Leu Thr Val Lys Gly Lys Pro His Phe Ala Asp Phe Asn Leu Val
65                  70                  75                  80

Pro Pro Asp Trp Gly Gly Tyr Ala Gly Pro Trp Ile Glu Ala Ala Ala
            85                  90                  95

Arg Gly Cys His Gly Leu Glu Glu Leu Arg Met Lys Arg Met Val Val
            100                 105                 110

Ser Asp Glu Ser Leu Glu Leu Leu Ala Arg Ser Phe Pro Arg Phe Arg
        115                 120                 125

Ala Leu Val Leu Ile Ser Cys Glu Gly Phe Ser Thr Asp Gly Leu Ala
    130                 135                 140

Ala Val Ala Ser His Cys Lys Leu Leu Arg Glu Leu Asp Leu Gln Glu
145                 150                 155                 160

Asn Glu Val Glu Asp Arg Gly Pro Arg Trp Leu Ser Cys Phe Pro Asp
            165                 170                 175

Ser Cys Thr Ser Leu Val Ser Leu Asn Phe Ala Cys Ile Lys Gly Glu
        180                 185                 190

Val Asn Ala Gly Ser Leu Glu Arg Leu Val Ser Arg Ser Pro Asn Leu
    195                 200                 205

Arg Ser Leu Arg Leu Asn Arg Ser Val Ser Val Asp Thr Leu Ala Lys
210                 215                 220

Ile Leu Leu Arg Thr Pro Asn Leu Glu Asp Leu Gly Thr Gly Asn Leu
225                 230                 235                 240

Thr Asp Asp Phe Gln Thr Glu Ser Tyr Phe Lys Leu Thr Ser Ala Leu
            245                 250                 255

Glu Lys Cys Lys Met Leu Arg Ser Leu Ser Gly Phe Trp Asp Ala Ser
        260                 265                 270

Pro Val Cys Leu Ser Phe Ile Tyr Pro Leu Cys Ala Gln Leu Thr Gly
    275                 280                 285

Leu Asn Leu Ser Tyr Ala Pro Thr Leu Asp Ala Ser Asp Leu Thr Lys
    290                 295                 300

Met Ile Ser Arg Cys Val Lys Leu Gln Arg Leu Trp Val Leu Asp Cys
305                 310                 315                 320

Ile Ser Asp Lys Gly Leu Gln Val Val Ala Ser Ser Cys Lys Asp Leu
            325                 330                 335
```

Gln Glu Leu Arg Val Phe Pro Ser Asp Phe Tyr Val Ala Gly Tyr Ser
            340                 345                 350

Ala Val Thr Glu Glu Gly Leu Val Ala Val Ser Leu Gly Cys Pro Lys
            355                 360                 365

Leu Asn Ser Leu Leu Tyr Phe Cys His Gln Met Thr Asn Ala Ala Leu
        370                 375                 380

Val Thr Val Ala Lys Asn Cys Pro Asn Phe Thr Arg Phe Arg Leu Cys
385                 390                 395                 400

Ile Leu Glu Pro Gly Lys Pro Asp Val Val Thr Ser Gln Pro Leu Asp
            405                 410                 415

Glu Gly Phe Gly Ala Ile Val Arg Glu Cys Lys Gly Leu Gln Arg Leu
            420                 425                 430

Ser Ile Ser Gly Leu Leu Thr Asp Lys Val Phe Met Tyr Ile Gly Lys
        435                 440                 445

Tyr Ala Lys Gln Leu Glu Met Leu Ser Ile Ala Phe Ala Gly Asp Ser
    450                 455                 460

Asp Lys Gly Met Met His Val Met Asn Gly Cys Lys Asn Leu Arg Lys
465                 470                 475                 480

Leu Glu Ile Arg Asp Ser Pro Phe Gly Asp Ala Ala Leu Leu Gly Asn
            485                 490                 495

Phe Ala Arg Tyr Glu Thr Met Arg Ser Leu Trp Met Ser Ser Cys Asn
            500                 505                 510

Val Thr Leu Lys Gly Cys Gln Val Leu Ala Ser Lys Met Pro Met Leu
        515                 520                 525

Asn Val Glu Val Ile Asn Glu Arg Asp Gly Ser Asn Glu Met Glu Glu
530                 535                 540

Asn His Gly Asp Leu Pro Lys Val Glu Lys Leu Tyr Val Tyr Arg Thr
545                 550                 555                 560

Thr Ala Gly Ala Arg Asp Asp Ala Pro Asn Phe Val Lys Ile Leu
            565                 570                 575

<210> SEQ ID NO 12
<211> LENGTH: 1791
<212> TYPE: DNA
<213> ORGANISM: Artificial
<220> FEATURE:
<223> OTHER INFORMATION: OsTIR1 (codon optimized)

<400> SEQUENCE: 12
atgggcggag aggcccctga ggctcggaga ctggatagag ccatgagctt tggcggagcc      60
ggcagcatcc ctgaagaggc cctgcatctg gtgctgggct acgtggacga ccccagagac     120
agagaagccg tgtccctcgt gtgccggcgg tggcacagaa tcgatgccct gaccagaaag     180
cacgtgaccg tgcctttctg ctacgccgcc agccctgctc atctgctggc cagattcccc     240
cggctggaaa gcctggccgt gaagggaaaa cccagagccg ctatgtacgg cctgatcccc     300
gaagattggg gcgcctacgc tagaccttgg gtggccgaac tggccgctcc tctggaatgt     360
ctgaaagccc tgcacctgag gcggatggtc gtgaccgacg atgatctggc tgccctcgtg     420
cgggccagag acacatgct gcaggaactg aagctggaca gtgcagcgg cttcagcacc     480 gacgccctga ctggtggc cagaagctgc agaagcctgc ggaccctgtt cctggaagag     540
tgctctatcg ccgacaacgg caccgagtgg ctgcacgacc tggctgtgaa caaccctgtg     600
ctggaaaccc tgaacttcca catgaccgag ctgaccgtgg tgcccgccga tctgaactg     660 ctggctaaga agtgcaagag cctgatcagc ctgaagatca gcgactgcga cttcagcgac     720

```
ctgatcggct tcttccggat ggccgcatct ctgcaggaat ttgccggcgg agccttcatc      780
gagcagggcg agctgactaa gtacggcaac gtgaagttcc ccagcagact gtgcagcctg      840
ggcctgacct acatgggcac caacgagatg cccattatct cccattcag cgccctgctg       900 aagaagctgg atctgcagta caccttcctg accaccgagg accactgcca gctgatcgcc      960
aagtgcccca acctgctggt gctggccgtg cggaatgtga tcggcgacag aggactgggc     1020
gtggtggcca tacctgcaa gaaactgcag aggctgcggg tggaacgggg cgacgacgat      1080
cctggactgc aggaagaaca gggcggcgtg tcacaagtgg gactgaccac agtggccgtg     1140
ggctgcagag agctggagta tatcgccgcc tacgtgtccg acatcaccaa cggcgccctg     1200
gaatctatcg gcaccttctg caagaacctg tgcgacttta ctggtgct gctggaccgg       1260 gaagagagaa tcaccgacct gcccctggac aacggcgtgc gggctctgct gagaggctgt     1320
accaagctgc ggagattcgc cctgtatctg aggcctggcg gcctgagcga tacaggcctg     1380
ggctacatcg ccagtacag cggcatcatc cagtacatgc tgctgggcaa tgtgggcgag     1440
acagacgacg gactgatccg ctttgccctg ggctgcgaga acctgagaaa gctggaactg     1500
agaagctgct gctttagcga gcaggccctg gccagagcca tcagatccat gcccagcctg     1560
agatacgtgt gggtgcaggg atacaaggcc agcaagaccg ccacgacct gatgctgatg     1620 gccagaccct tctggaacat cgagttcacc cccccagca gcgagaacgc caaccggatg      1680
agagaggacg gcgagccttg cgtggactcc caggctcaga tcctggccta ctactccctg     1740
gccggcaaga aagcgactg ccccagatct gtggtgcccc tgtatcctgc c                1791
```

<210> SEQ ID NO 13
<211> LENGTH: 597
<212> TYPE: PRT
<213> ORGANISM: Oryza sativa

<400> SEQUENCE: 13

```
Met Gly Gly Glu Ala Pro Glu Ala Arg Arg Leu Asp Arg Ala Met Ser
1               5                   10                  15

Phe Gly Gly Ala Gly Ser Ile Pro Glu Glu Ala Leu His Leu Val Leu
                20                  25                  30

Gly Tyr Val Asp Asp Pro Arg Asp Arg Glu Ala Val Ser Leu Val Cys
            35                  40                  45

Arg Arg Trp His Arg Ile Asp Ala Leu Thr Arg Lys His Val Thr Val
        50                  55                  60

Pro Phe Cys Tyr Ala Ala Ser Pro Ala His Leu Leu Ala Arg Phe Pro
65                  70                  75                  80

Arg Leu Glu Ser Leu Ala Val Lys Gly Lys Pro Arg Ala Ala Met Tyr
                85                  90                  95

Gly Leu Ile Pro Glu Asp Trp Gly Ala Tyr Ala Arg Pro Trp Val Ala
            100                 105                 110

Glu Leu Ala Ala Pro Leu Glu Cys Leu Lys Ala Leu His Leu Arg Arg
        115                 120                 125

Met Val Val Thr Asp Asp Leu Ala Ala Leu Val Arg Ala Arg Gly
    130                 135                 140

His Met Leu Gln Glu Lys Leu Asp Lys Cys Ser Gly Phe Ser Thr
145                 150                 155                 160

Asp Ala Leu Arg Leu Val Ala Arg Ser Cys Arg Ser Leu Arg Thr Leu
                165                 170                 175

Phe Leu Glu Glu Cys Ser Ile Ala Asp Asn Gly Thr Glu Trp Leu His
```

```
                180                 185                 190
Asp Leu Ala Val Asn Asn Pro Val Leu Glu Thr Leu Asn Phe His Met
            195                 200                 205

Thr Glu Leu Thr Val Val Pro Ala Asp Leu Glu Leu Leu Ala Lys Lys
            210                 215                 220

Cys Lys Ser Leu Ile Ser Leu Lys Ile Ser Asp Cys Asp Phe Ser Asp
225                 230                 235                 240

Leu Ile Gly Phe Phe Arg Met Ala Ala Ser Leu Gln Glu Phe Ala Gly
            245                 250                 255

Gly Ala Phe Ile Glu Gln Gly Glu Leu Thr Lys Tyr Gly Asn Val Lys
            260                 265                 270

Phe Pro Ser Arg Leu Cys Ser Leu Gly Leu Thr Tyr Met Gly Thr Asn
            275                 280                 285

Glu Met Pro Ile Ile Phe Pro Phe Ser Ala Leu Leu Lys Lys Leu Asp
            290                 295                 300

Leu Gln Tyr Thr Phe Leu Thr Thr Glu Asp His Cys Gln Leu Ile Ala
305                 310                 315                 320

Lys Cys Pro Asn Leu Leu Val Leu Ala Val Arg Asn Val Ile Gly Asp
            325                 330                 335

Arg Gly Leu Gly Val Val Ala Asp Thr Cys Lys Lys Leu Gln Arg Leu
            340                 345                 350

Arg Val Glu Arg Gly Asp Asp Pro Gly Leu Gln Glu Glu Gln Gly
            355                 360                 365

Gly Val Ser Gln Val Gly Leu Thr Thr Val Ala Val Gly Cys Arg Glu
            370                 375                 380

Leu Glu Tyr Ile Ala Ala Tyr Val Ser Asp Ile Thr Asn Gly Ala Leu
385                 390                 395                 400

Glu Ser Ile Gly Thr Phe Cys Lys Asn Leu Cys Asp Phe Arg Leu Val
            405                 410                 415

Leu Leu Asp Arg Glu Glu Arg Ile Thr Asp Leu Pro Leu Asp Asn Gly
            420                 425                 430

Val Arg Ala Leu Leu Arg Gly Cys Thr Lys Leu Arg Arg Phe Ala Leu
            435                 440                 445

Tyr Leu Arg Pro Gly Gly Leu Ser Asp Thr Gly Leu Gly Tyr Ile Gly
            450                 455                 460

Gln Tyr Ser Gly Ile Ile Gln Tyr Met Leu Leu Gly Asn Val Gly Glu
465                 470                 475                 480

Thr Asp Asp Gly Leu Ile Arg Phe Ala Leu Gly Cys Glu Asn Leu Arg
            485                 490                 495

Lys Leu Glu Leu Arg Ser Cys Cys Phe Ser Glu Gln Ala Leu Ala Arg
            500                 505                 510

Ala Ile Arg Ser Met Pro Ser Leu Arg Tyr Val Trp Val Gln Gly Tyr
            515                 520                 525

Lys Ala Ser Lys Thr Gly His Asp Leu Met Leu Met Ala Arg Pro Phe
            530                 535                 540

Trp Asn Ile Glu Phe Thr Pro Pro Ser Ser Glu Asn Ala Asn Arg Met
545                 550                 555                 560

Arg Glu Asp Gly Glu Pro Cys Val Asp Ser Gln Ala Gln Ile Leu Ala
            565                 570                 575

Tyr Tyr Ser Leu Ala Gly Lys Arg Ser Asp Cys Pro Arg Ser Val Val
            580                 585                 590

Pro Leu Tyr Pro Ala
            595
```

<210> SEQ ID NO 14
<211> LENGTH: 587
<212> TYPE: PRT
<213> ORGANISM: Artificial
<220> FEATURE:
<223> OTHER INFORMATION: OsTIR1F-Box-OsCOI1BLRR

<400> SEQUENCE: 14

```
Met Tyr Pro Tyr Asp Val Pro Asp Tyr Ala Thr Tyr Phe Pro Glu Glu
1               5                   10                  15

Val Val Glu His Ile Phe Ser Phe Leu Pro Ala Gln Arg Asp Arg Asn
            20                  25                  30

Thr Val Ser Leu Val Cys Lys Val Trp Tyr Glu Ile Glu Arg Leu Ser
        35                  40                  45

Arg Lys His Val Thr Val Pro Phe Cys Tyr Ala Ala Ser Pro Ala His
    50                  55                  60

Leu Leu Ala Arg Phe Pro Arg Leu Glu Ser Leu Ala Val Lys Gly Lys
65                  70                  75                  80

Pro Arg Ala Ala Met Tyr Gly Leu Ile Pro Glu Asp Trp Gly Ala Tyr
                85                  90                  95

Ala Arg Pro Trp Val Ala Glu Leu Ala Ala Pro Leu Glu Cys Leu Lys
            100                 105                 110

Ala Leu His Leu Arg Arg Met Val Val Thr Asp Asp Leu Ala Ala
        115                 120                 125

Leu Val Arg Ala Arg Gly His Met Leu Gln Glu Leu Lys Leu Asp Lys
    130                 135                 140

Cys Ser Gly Phe Ser Thr Asp Ala Leu Arg Leu Val Ala Arg Ser Cys
145                 150                 155                 160

Arg Ser Leu Arg Thr Leu Phe Leu Glu Glu Cys Ser Ile Ala Asp Asn
                165                 170                 175

Gly Thr Glu Trp Leu His Asp Leu Ala Val Asn Asn Pro Val Leu Glu
            180                 185                 190

Thr Leu Asn Phe His Met Thr Glu Leu Thr Val Val Pro Ala Asp Leu
        195                 200                 205

Glu Leu Leu Ala Lys Lys Cys Lys Ser Leu Ile Ser Leu Lys Ile Ser
    210                 215                 220

Asp Cys Asp Phe Ser Asp Leu Ile Gly Phe Phe Arg Met Ala Ala Ser
225                 230                 235                 240

Leu Gln Glu Phe Ala Gly Gly Ala Phe Ile Glu Gln Gly Glu Leu Thr
                245                 250                 255

Lys Tyr Gly Asn Val Lys Phe Pro Ser Arg Leu Cys Ser Leu Gly Leu
            260                 265                 270

Thr Tyr Met Gly Thr Asn Glu Met Pro Ile Ile Phe Pro Phe Ser Ala
        275                 280                 285

Leu Leu Lys Lys Leu Asp Leu Gln Tyr Thr Phe Leu Thr Thr Glu Asp
    290                 295                 300

His Cys Gln Leu Ile Ala Lys Cys Pro Asn Leu Leu Val Leu Ala Val
305                 310                 315                 320

Arg Asn Val Ile Gly Asp Arg Gly Leu Gly Val Val Ala Asp Thr Cys
                325                 330                 335

Lys Lys Leu Gln Arg Leu Arg Val Glu Arg Gly Asp Asp Pro Gly
            340                 345                 350

Leu Gln Glu Glu Gln Gly Gly Val Ser Gln Val Gly Leu Thr Thr Val
        355                 360                 365
```

```
Ala Val Gly Cys Arg Glu Leu Glu Tyr Ile Ala Ala Tyr Val Ser Asp
        370                 375                 380

Ile Thr Asn Gly Ala Leu Glu Ser Ile Gly Thr Phe Cys Lys Asn Leu
385                 390                 395                 400

Cys Asp Phe Arg Leu Val Leu Leu Asp Arg Glu Glu Arg Ile Thr Asp
                405                 410                 415

Leu Pro Leu Asp Asn Gly Val Arg Ala Leu Leu Arg Gly Cys Thr Lys
                420                 425                 430

Leu Arg Arg Phe Ala Leu Tyr Leu Arg Pro Gly Gly Leu Ser Asp Thr
            435                 440                 445

Gly Leu Gly Tyr Ile Gly Gln Tyr Ser Gly Ile Ile Gln Tyr Met Leu
    450                 455                 460

Leu Gly Asn Val Gly Glu Thr Asp Asp Gly Leu Ile Arg Phe Ala Leu
465                 470                 475                 480

Gly Cys Glu Asn Leu Arg Lys Leu Glu Leu Arg Ser Cys Cys Phe Ser
                485                 490                 495

Glu Gln Ala Leu Ala Arg Ala Ile Arg Ser Met Pro Ser Leu Arg Tyr
                500                 505                 510

Val Trp Val Gln Gly Tyr Lys Ala Ser Lys Thr Gly His Asp Leu Met
            515                 520                 525

Leu Met Ala Arg Pro Phe Trp Asn Ile Glu Phe Thr Pro Pro Ser Ser
    530                 535                 540

Glu Asn Ala Asn Arg Met Arg Glu Asp Gly Glu Pro Cys Val Asp Ser
545                 550                 555                 560

Gln Ala Gln Ile Leu Ala Tyr Tyr Ser Leu Ala Gly Lys Arg Ser Asp
                565                 570                 575

Cys Pro Arg Ser Val Val Pro Leu Tyr Pro Ala
                580                 585

<210> SEQ ID NO 15
<211> LENGTH: 33
<212> TYPE: PRT
<213> ORGANISM: Artificial
<220> FEATURE:
<223> OTHER INFORMATION: OsJAZ33

<400> SEQUENCE: 15

His Ala Ala Ala Leu Pro Glu Met Pro Ile Ala Arg Lys Ala Ser Leu
1               5                   10                  15

Gln Arg Phe Leu Gln Lys Arg Lys His Arg Ile Thr Thr Thr Ser Glu
            20                  25                  30

Pro

<210> SEQ ID NO 16
<211> LENGTH: 43
<212> TYPE: PRT
<213> ORGANISM: Artificial
<220> FEATURE:
<223> OTHER INFORMATION: OsJAZ43

<400> SEQUENCE: 16

Pro Pro Gln Pro Ala His Ala Ala Ala Leu Pro Glu Met Pro Ile Ala
1               5                   10                  15

Arg Lys Ala Ser Leu Gln Arg Phe Leu Gln Lys Arg Lys His Arg Ile
            20                  25                  30

Thr Thr Thr Ser Glu Pro Tyr Lys Lys Ala Ala
        35                  40
```

```
<210> SEQ ID NO 17
<211> LENGTH: 7
<212> TYPE: PRT
<213> ORGANISM: Artificial
<220> FEATURE:
<223> OTHER INFORMATION: SV40 NLS

<400> SEQUENCE: 17

Pro Lys Lys Lys Arg Lys Val
1               5

<210> SEQ ID NO 18
<211> LENGTH: 20
<212> TYPE: DNA
<213> ORGANISM: Artificial
<220> FEATURE:
<223> OTHER INFORMATION: Forward primer

<400> SEQUENCE: 18
acccactcct ccacctttga                                              20

<210> SEQ ID NO 19
<211> LENGTH: 22
<212> TYPE: DNA
<213> ORGANISM: Artificial
<220> FEATURE:
<223> OTHER INFORMATION: Reverse primer

<400> SEQUENCE: 19
ctgttgctgt agccaaattc gt                                           22

<210> SEQ ID NO 20
<211> LENGTH: 20
<212> TYPE: DNA
<213> ORGANISM: Artificial
<220> FEATURE:
<223> OTHER INFORMATION: Forward primer

<400> SEQUENCE: 20
gaccagtcaa caggggacat                                              20

<210> SEQ ID NO 21
<211> LENGTH: 20
<212> TYPE: DNA
<213> ORGANISM: Artificial
<220> FEATURE:
<223> OTHER INFORMATION: Reverse primer

<400> SEQUENCE: 21
cctgaccaag gaaagcaaag                                              20

<210> SEQ ID NO 22
<211> LENGTH: 23
<212> TYPE: DNA
<213> ORGANISM: Artificial
<220> FEATURE:
<223> OTHER INFORMATION: Forward primer

<400> SEQUENCE: 22
gaatcatcgg actcaggtac atc                                          23

<210> SEQ ID NO 23
<211> LENGTH: 23
<212> TYPE: DNA
<213> ORGANISM: Artificial
```

```
<220> FEATURE:
<223> OTHER INFORMATION: Reverse primer

<400> SEQUENCE: 23
tctgtctcac taattgctct cct                                          23

<210> SEQ ID NO 24
<211> LENGTH: 19
<212> TYPE: DNA
<213> ORGANISM: Artificial
<220> FEATURE:
<223> OTHER INFORMATION: Forward primer

<400> SEQUENCE: 24
tgtccgtcag aacccatgc                                               19

<210> SEQ ID NO 25
<211> LENGTH: 21
<212> TYPE: DNA
<213> ORGANISM: Artificial
<220> FEATURE:
<223> OTHER INFORMATION: Reverse primer

<400> SEQUENCE: 25
aaagtcgaag ttccatcgct c                                            21

<210> SEQ ID NO 26
<211> LENGTH: 20
<212> TYPE: DNA
<213> ORGANISM: Artificial
<220> FEATURE:
<223> OTHER INFORMATION: Forward primer

<400> SEQUENCE: 26
aggagagtgc ggacgagaat                                              20

<210> SEQ ID NO 27
<211> LENGTH: 21
<212> TYPE: DNA
<213> ORGANISM: Artificial
<220> FEATURE:
<223> OTHER INFORMATION: Reverse primer

<400> SEQUENCE: 27
aacctagagc cgaactcaag t                                            21

<210> SEQ ID NO 28
<211> LENGTH: 19
<212> TYPE: DNA
<213> ORGANISM: Artificial
<220> FEATURE:
<223> OTHER INFORMATION: Forward primer

<400> SEQUENCE: 28
accgcatcaa cagcagcat                                               19

<210> SEQ ID NO 29
<211> LENGTH: 21
<212> TYPE: DNA
<213> ORGANISM: Artificial
<220> FEATURE:
<223> OTHER INFORMATION: Reverse primer

<400> SEQUENCE: 29
gaaggctttg ctgtgcttca g                                            21
```

<210> SEQ ID NO 30
<211> LENGTH: 26
<212> TYPE: DNA
<213> ORGANISM: Artificial
<220> FEATURE:
<223> OTHER INFORMATION: Forward primer

<400> SEQUENCE: 30
cagtggcagt ctcaggttaa gaagga        26

<210> SEQ ID NO 31
<211> LENGTH: 21
<212> TYPE: DNA
<213> ORGANISM: Artificial
<220> FEATURE:
<223> OTHER INFORMATION: Reverse primer

<400> SEQUENCE: 31
cgctactgca ggtgtgagca a        21

<210> SEQ ID NO 32
<211> LENGTH: 18
<212> TYPE: DNA
<213> ORGANISM: Artificial
<220> FEATURE:
<223> OTHER INFORMATION: Forward primer

<400> SEQUENCE: 32
tttcccctcg ctttctca        18

<210> SEQ ID NO 33
<211> LENGTH: 18
<212> TYPE: DNA
<213> ORGANISM: Artificial
<220> FEATURE:
<223> OTHER INFORMATION: Reverse primer

<400> SEQUENCE: 33
tgcaggctga attcggtt        18

<210> SEQ ID NO 34
<211> LENGTH: 19
<212> TYPE: DNA
<213> ORGANISM: Artificial
<220> FEATURE:
<223> OTHER INFORMATION: Forward primer

<400> SEQUENCE: 34
gcccctcatt aagcccaag        19

<210> SEQ ID NO 35
<211> LENGTH: 21
<212> TYPE: DNA
<213> ORGANISM: Artificial
<220> FEATURE:
<223> OTHER INFORMATION: Reverse primer

<400> SEQUENCE: 35
ttgtggtggt ctgacagttc g        21

<210> SEQ ID NO 36
<211> LENGTH: 20
<212> TYPE: DNA
<213> ORGANISM: Artificial
<220> FEATURE:
<223> OTHER INFORMATION: Forward primer

<400> SEQUENCE: 36
gcgggctcta cagcaagatg                                               20

<210> SEQ ID NO 37
<211> LENGTH: 21
<212> TYPE: DNA
<213> ORGANISM: Artificial
<220> FEATURE:
<223> OTHER INFORMATION: Reverse primer

<400> SEQUENCE: 37
acagttggca caggacaatc c                                             21

<210> SEQ ID NO 38
<211> LENGTH: 22
<212> TYPE: DNA
<213> ORGANISM: Artificial
<220> FEATURE:
<223> OTHER INFORMATION: Forward primer

<400> SEQUENCE: 38
cctgaagacg tgtgaagatg ag                                            22

<210> SEQ ID NO 39
<211> LENGTH: 22
<212> TYPE: DNA
<213> ORGANISM: Artificial
<220> FEATURE:
<223> OTHER INFORMATION: Reverse primer

<400> SEQUENCE: 39
gctgattagg ctccaaccat ac                                            22

<210> SEQ ID NO 40
<211> LENGTH: 21
<212> TYPE: DNA
<213> ORGANISM: Artificial
<220> FEATURE:
<223> OTHER INFORMATION: Forward primer

<400> SEQUENCE: 40
aggtattacg agactggctc c                                             21

<210> SEQ ID NO 41
<211> LENGTH: 22
<212> TYPE: DNA
<213> ORGANISM: Artificial
<220> FEATURE:
<223> OTHER INFORMATION: Reverse primer

<400> SEQUENCE: 41
tcccgcttat actgggctat tt                                            22

<210> SEQ ID NO 42
<211> LENGTH: 21
<212> TYPE: DNA
<213> ORGANISM: Artificial
<220> FEATURE:
<223> OTHER INFORMATION: Forward primer

<400> SEQUENCE: 42
atgaaggaac cctgtttccg t                                             21

<210> SEQ ID NO 43

```
<211> LENGTH: 22
<212> TYPE: DNA
<213> ORGANISM: Artificial
<220> FEATURE:
<223> OTHER INFORMATION: Reverse primer

<400> SEQUENCE: 43
agatgatgga gtagatggtg gg                                          22

<210> SEQ ID NO 44
<211> LENGTH: 20
<212> TYPE: DNA
<213> ORGANISM: Artificial
<220> FEATURE:
<223> OTHER INFORMATION: Forward primer

<400> SEQUENCE: 44
cctgcccgtt cttgaaatgt                                             20

<210> SEQ ID NO 45
<211> LENGTH: 21
<212> TYPE: DNA
<213> ORGANISM: Artificial
<220> FEATURE:
<223> OTHER INFORMATION: Reverse primer

<400> SEQUENCE: 45
ggagcatctt cttcggaacc t                                           21

<210> SEQ ID NO 46
<211> LENGTH: 21
<212> TYPE: DNA
<213> ORGANISM: Artificial
<220> FEATURE:
<223> OTHER INFORMATION: Forward primer

<400> SEQUENCE: 46
caaggacgtg agcatgtatc c                                           21

<210> SEQ ID NO 47
<211> LENGTH: 21
<212> TYPE: DNA
<213> ORGANISM: Artificial
<220> FEATURE:
<223> OTHER INFORMATION: Reverse primer

<400> SEQUENCE: 47
gtaaccaccg tagtccgggt a                                           21

<210> SEQ ID NO 48
<211> LENGTH: 21
<212> TYPE: DNA
<213> ORGANISM: Artificial
<220> FEATURE:
<223> OTHER INFORMATION: Forward primer

<400> SEQUENCE: 48
tgcatcagtg acggtaaacc a                                           21

<210> SEQ ID NO 49
<211> LENGTH: 21
<212> TYPE: DNA
<213> ORGANISM: Artificial
<220> FEATURE:
<223> OTHER INFORMATION: Reverse primer

<400> SEQUENCE: 49
```
ttcttcagcc gtgcaacaat c                                            21

<210> SEQ ID NO 50
<211> LENGTH: 19
<212> TYPE: DNA
<213> ORGANISM: Artificial
<220> FEATURE:
<223> OTHER INFORMATION: Forward primer

<400> SEQUENCE: 50
caggcaagga tgacagacg                                               19

<210> SEQ ID NO 51
<211> LENGTH: 20
<212> TYPE: DNA
<213> ORGANISM: Artificial
<220> FEATURE:
<223> OTHER INFORMATION: Reverse primer

<400> SEQUENCE: 51
gagacagcac gaaggactgc                                              20

<210> SEQ ID NO 52
<211> LENGTH: 21
<212> TYPE: DNA
<213> ORGANISM: Artificial
<220> FEATURE:
<223> OTHER INFORMATION: Forward primer

<400> SEQUENCE: 52
tatcaaggag gcccattttg c                                            21

<210> SEQ ID NO 53
<211> LENGTH: 23
<212> TYPE: DNA
<213> ORGANISM: Artificial
<220> FEATURE:
<223> OTHER INFORMATION: Reverse primer

<400> SEQUENCE: 53
tgtttccact tctaaaccat gct                                          23

<210> SEQ ID NO 54
<211> LENGTH: 20
<212> TYPE: DNA
<213> ORGANISM: Artificial
<220> FEATURE:
<223> OTHER INFORMATION: Forward primer

<400> SEQUENCE: 54
agaacatcat ccctgcatcc                                              20

<210> SEQ ID NO 55
<211> LENGTH: 20
<212> TYPE: DNA
<213> ORGANISM: Artificial
<220> FEATURE:
<223> OTHER INFORMATION: Reverse primer

<400> SEQUENCE: 55
cacattgggg gtaggaacac                                              20

<210> SEQ ID NO 56
<211> LENGTH: 19
<212> TYPE: DNA

```
<213> ORGANISM: Artificial
<220> FEATURE:
<223> OTHER INFORMATION: Forward primer

<400> SEQUENCE: 56
ccctacccag cctacatgg                                                        19

<210> SEQ ID NO 57
<211> LENGTH: 22
<212> TYPE: DNA
<213> ORGANISM: Artificial
<220> FEATURE:
<223> OTHER INFORMATION: Reverse primer

<400> SEQUENCE: 57
acatatcgag attggggtgt ct                                                    22

<210> SEQ ID NO 58
<211> LENGTH: 20
<212> TYPE: DNA
<213> ORGANISM: Artificial
<220> FEATURE:
<223> OTHER INFORMATION: Forward primer

<400> SEQUENCE: 58
ttgctccggt aacagcagtg                                                       20

<210> SEQ ID NO 59
<211> LENGTH: 21
<212> TYPE: DNA
<213> ORGANISM: Artificial
<220> FEATURE:
<223> OTHER INFORMATION: Reverse primer

<400> SEQUENCE: 59
gtggtcgctt gtgtagaagg a                                                     21

<210> SEQ ID NO 60
<211> LENGTH: 20
<212> TYPE: DNA
<213> ORGANISM: Artificial
<220> FEATURE:
<223> OTHER INFORMATION: Forward primer

<400> SEQUENCE: 60
cccctcttcc gtcctcttac                                                       20

<210> SEQ ID NO 61
<211> LENGTH: 20
<212> TYPE: DNA
<213> ORGANISM: Artificial
<220> FEATURE:
<223> OTHER INFORMATION: Reverse primer

<400> SEQUENCE: 61
ctgcgagtgg tcacactgat                                                       20

<210> SEQ ID NO 62
<211> LENGTH: 21
<212> TYPE: DNA
<213> ORGANISM: Artificial
<220> FEATURE:
<223> OTHER INFORMATION: Forward primer

<400> SEQUENCE: 62
tgtctgtgtc taccgagggt g                                                     21
```

<210> SEQ ID NO 63
<211> LENGTH: 23
<212> TYPE: DNA
<213> ORGANISM: Artificial
<220> FEATURE:
<223> OTHER INFORMATION: Reverse primer

<400> SEQUENCE: 63
tccaacggac tttaacaact tca                                              23

<210> SEQ ID NO 64
<211> LENGTH: 20
<212> TYPE: DNA
<213> ORGANISM: Artificial
<220> FEATURE:
<223> OTHER INFORMATION: Forward primer

<400> SEQUENCE: 64
atccgcccgg accctccaaa                                                  20

<210> SEQ ID NO 65
<211> LENGTH: 23
<212> TYPE: DNA
<213> ORGANISM: Artificial
<220> FEATURE:
<223> OTHER INFORMATION: Reverse primer

<400> SEQUENCE: 65
tcggttctgg aaccacacct gga                                              23

<210> SEQ ID NO 66
<211> LENGTH: 27
<212> TYPE: DNA
<213> ORGANISM: Artificial
<220> FEATURE:
<223> OTHER INFORMATION: Forward primer

<400> SEQUENCE: 66
aggagaagaa gaaccaagaa tggagga                                          27

<210> SEQ ID NO 67
<211> LENGTH: 21
<212> TYPE: DNA
<213> ORGANISM: Artificial
<220> FEATURE:
<223> OTHER INFORMATION: Reverse primer

<400> SEQUENCE: 67
tcggcttctg gacctcccag t                                                21

<210> SEQ ID NO 68
<211> LENGTH: 21
<212> TYPE: DNA
<213> ORGANISM: Artificial
<220> FEATURE:
<223> OTHER INFORMATION: Forward primer

<400> SEQUENCE: 68
aaaagagcag gatgaggagc c                                                21

<210> SEQ ID NO 69
<211> LENGTH: 21
<212> TYPE: DNA
<213> ORGANISM: Artificial
<220> FEATURE:

```
<223> OTHER INFORMATION: Reverse primer

<400> SEQUENCE: 69
gtccttcaag tctgctggca c                                        21

<210> SEQ ID NO 70
<211> LENGTH: 19
<212> TYPE: DNA
<213> ORGANISM: Artificial
<220> FEATURE:
<223> OTHER INFORMATION: Forward primer

<400> SEQUENCE: 70
cctggtgatg tccgacctg                                           19

<210> SEQ ID NO 71
<211> LENGTH: 19
<212> TYPE: DNA
<213> ORGANISM: Artificial
<220> FEATURE:
<223> OTHER INFORMATION: Reverse primer

<400> SEQUENCE: 71
ccatgagcgc atcgcaatc                                           19

<210> SEQ ID NO 72
<211> LENGTH: 20
<212> TYPE: DNA
<213> ORGANISM: Artificial
<220> FEATURE:
<223> OTHER INFORMATION: Forward primer

<400> SEQUENCE: 72
gcagcgcagg agcagaacca                                          20

<210> SEQ ID NO 73
<211> LENGTH: 20
<212> TYPE: DNA
<213> ORGANISM: Artificial
<220> FEATURE:
<223> OTHER INFORMATION: Reverse primer

<400> SEQUENCE: 73
gcactcgggc ctcggtaagc                                          20

<210> SEQ ID NO 74
<211> LENGTH: 20
<212> TYPE: DNA
<213> ORGANISM: Artificial
<220> FEATURE:
<223> OTHER INFORMATION: Forward primer

<400> SEQUENCE: 74
atgcaccgct acgacatggg                                          20

<210> SEQ ID NO 75
<211> LENGTH: 22
<212> TYPE: DNA
<213> ORGANISM: Artificial
<220> FEATURE:
<223> OTHER INFORMATION: Reverse primer

<400> SEQUENCE: 75
gctccgactt gaccagagat cc                                       22
```

```
<210> SEQ ID NO 76
<211> LENGTH: 20
<212> TYPE: DNA
<213> ORGANISM: Artificial
<220> FEATURE:
<223> OTHER INFORMATION: Forward primer

<400> SEQUENCE: 76
cgcacggaat tcgaacagta                                              20

<210> SEQ ID NO 77
<211> LENGTH: 20
<212> TYPE: DNA
<213> ORGANISM: Artificial
<220> FEATURE:
<223> OTHER INFORMATION: Reverse primer

<400> SEQUENCE: 77
gtcaaatgtc ggggtagttg                                              20

<210> SEQ ID NO 78
<211> LENGTH: 22
<212> TYPE: DNA
<213> ORGANISM: Artificial
<220> FEATURE:
<223> OTHER INFORMATION: Forward primer

<400> SEQUENCE: 78
cccccgacct tcagggaca ag                                            22

<210> SEQ ID NO 79
<211> LENGTH: 22
<212> TYPE: DNA
<213> ORGANISM: Artificial
<220> FEATURE:
<223> OTHER INFORMATION: Reverse primer

<400> SEQUENCE: 79
ggacagtgtc agcgccttcc at                                           22

<210> SEQ ID NO 80
<211> LENGTH: 23
<212> TYPE: DNA
<213> ORGANISM: Artificial
<220> FEATURE:
<223> OTHER INFORMATION: Forward primer

<400> SEQUENCE: 80
gcttcaagga gctaactaac gag                                          23

<210> SEQ ID NO 81
<211> LENGTH: 22
<212> TYPE: DNA
<213> ORGANISM: Artificial
<220> FEATURE:
<223> OTHER INFORMATION: Reverse primer

<400> SEQUENCE: 81
ccagcaagaa agagtacatg gc                                           22

<210> SEQ ID NO 82
<211> LENGTH: 20
<212> TYPE: DNA
<213> ORGANISM: Artificial
<220> FEATURE:
<223> OTHER INFORMATION: Forward primer
```

<400> SEQUENCE: 82
aaattccagg tgatcttgcg                                          20

<210> SEQ ID NO 83
<211> LENGTH: 20
<212> TYPE: DNA
<213> ORGANISM: Artificial
<220> FEATURE:
<223> OTHER INFORMATION: Reverse primer

<400> SEQUENCE: 83
tgtccttggg gtacagttgc                                          20

<210> SEQ ID NO 84
<211> LENGTH: 20
<212> TYPE: DNA
<213> ORGANISM: Artificial
<220> FEATURE:
<223> OTHER INFORMATION: Forward primer

<400> SEQUENCE: 84
agccgctacc ccgaccacat                                          20

<210> SEQ ID NO 85
<211> LENGTH: 20
<212> TYPE: DNA
<213> ORGANISM: Artificial
<220> FEATURE:
<223> OTHER INFORMATION: Reverse primer

<400> SEQUENCE: 85
cggttcacca gggtgtcgcc                                          20

<210> SEQ ID NO 86
<211> LENGTH: 20
<212> TYPE: DNA
<213> ORGANISM: Artificial
<220> FEATURE:
<223> OTHER INFORMATION: Forward primer

<400> SEQUENCE: 86
gacggcgacg taaacggcca                                          20

<210> SEQ ID NO 87
<211> LENGTH: 20
<212> TYPE: DNA
<213> ORGANISM: Artificial
<220> FEATURE:
<223> OTHER INFORMATION: Reverse primer

<400> SEQUENCE: 87
cagcttgccg gtggtgcaga                                          20

<210> SEQ ID NO 88
<211> LENGTH: 41
<212> TYPE: DNA
<213> ORGANISM: Artificial
<220> FEATURE:
<223> OTHER INFORMATION: Primer

<400> SEQUENCE: 88 caggggatc gtcgacgcca ccatgaccta cttccccgag g                   41

<210> SEQ ID NO 89
<211> LENGTH: 41

<212> TYPE: DNA
<213> ORGANISM: Artificial
<220> FEATURE:
<223> OTHER INFORMATION: Primer

<400> SEQUENCE: 89
gggccattgt cacatgctcg cggctcagtc tctcgatctc g         41

<210> SEQ ID NO 90
<211> LENGTH: 44
<212> TYPE: DNA
<213> ORGANISM: Artificial
<220> FEATURE:
<223> OTHER INFORMATION: Primer

<400> SEQUENCE: 90
atattacccg ggcctacacc tctgacagag ctgcctatcg ccag       44

<210> SEQ ID NO 91
<211> LENGTH: 43
<212> TYPE: DNA
<213> ORGANISM: Artificial
<220> FEATURE:
<223> OTHER INFORMATION: Primer

<400> SEQUENCE: 91
atactatcta gaaggagcct tgctggtcac tctgtccttc cgc        43

<210> SEQ ID NO 92
<211> LENGTH: 32
<212> TYPE: DNA
<213> ORGANISM: Artificial
<220> FEATURE:
<223> OTHER INFORMATION: Primer

<400> SEQUENCE: 92
acgtggcccg ggatgtcgag ttctatggaa tg                   32

<210> SEQ ID NO 93
<211> LENGTH: 33
<212> TYPE: DNA
<213> ORGANISM: Artificial
<220> FEATURE:
<223> OTHER INFORMATION: Primer

<400> SEQUENCE: 93
cgcggctcta gatatttcag ctgctaaacc gag                  33

<210> SEQ ID NO 94
<211> LENGTH: 47
<212> TYPE: DNA
<213> ORGANISM: Artificial
<220> FEATURE:
<223> OTHER INFORMATION: Primer

<400> SEQUENCE: 94
tatattcccg ggcacgccgc tgccctgcct gagatgccta tcgccag    47

<210> SEQ ID NO 95
<211> LENGTH: 46
<212> TYPE: DNA
<213> ORGANISM: Artificial
<220> FEATURE:
<223> OTHER INFORMATION: Primer

<400> SEQUENCE: 95
tgactgtcta gatggctcgc ttgtggtggt gattctgtgc ttccgc        46

<210> SEQ ID NO 96
<211> LENGTH: 67
<212> TYPE: DNA
<213> ORGANISM: Artificial
<220> FEATURE:
<223> OTHER INFORMATION: Primer

<400> SEQUENCE: 96
gtctgagtcg acgccaccat gtacccatac gatgttccag attacgctac ctacttcccc     60
gaggaag        67

<210> SEQ ID NO 97
<211> LENGTH: 27
<212> TYPE: DNA
<213> ORGANISM: Artificial
<220> FEATURE:
<223> OTHER INFORMATION: Primer

<400> SEQUENCE: 97
atcttattcg aagggccgg ggttctc        27

<210> SEQ ID NO 98
<211> LENGTH: 44
<212> TYPE: DNA
<213> ORGANISM: Artificial
<220> FEATURE:
<223> OTHER INFORMATION: Primer

<400> SEQUENCE: 98 caggggatc gtcgacgcca ccatgtaccc atacgatgtt ccag        44

<210> SEQ ID NO 99
<211> LENGTH: 41
<212> TYPE: DNA
<213> ORGANISM: Artificial
<220> FEATURE:
<223> OTHER INFORMATION: Primer

<400> SEQUENCE: 99
aaggcacggt cacgtgcttt ctgctcagtc tctcgatctc g        41

<210> SEQ ID NO 100
<211> LENGTH: 54
<212> TYPE: DNA
<213> ORGANISM: Artificial
<220> FEATURE:
<223> OTHER INFORMATION: Primer

<400> SEQUENCE: 100
gcagccgcta gcccaaaaaa gaaagaaaa gttatggtga gcaagggcga ggag        54

<210> SEQ ID NO 101
<211> LENGTH: 33
<212> TYPE: DNA
<213> ORGANISM: Artificial
<220> FEATURE:
<223> OTHER INFORMATION: Primer

<400> SEQUENCE: 101
gatgtgcccg ggcttgtaca gctcgtccat gcc        33

<210> SEQ ID NO 102
<211> LENGTH: 32

```
<212> TYPE: DNA
<213> ORGANISM: Artificial
<220> FEATURE:
<223> OTHER INFORMATION: Primer

<400> SEQUENCE: 102
atcagtcccg ggcttgtaca gctcgtccat gc                                    32

<210> SEQ ID NO 103
<211> LENGTH: 33
<212> TYPE: DNA
<213> ORGANISM: Artificial
<220> FEATURE:
<223> OTHER INFORMATION: Primer

<400> SEQUENCE: 103
gatgtggcta gcatggtgag caagggcgag gag                                   33

<210> SEQ ID NO 104
<211> LENGTH: 33
<212> TYPE: DNA
<213> ORGANISM: Artificial
<220> FEATURE:
<223> OTHER INFORMATION: Primer

<400> SEQUENCE: 104
atcagagcta gcatggtgag caagggcgag gag                                   33

<210> SEQ ID NO 105
<211> LENGTH: 42
<212> TYPE: DNA
<213> ORGANISM: Artificial
<220> FEATURE:
<223> OTHER INFORMATION: Primer

<400> SEQUENCE: 105
ggggatcgtc gacgccacca tggtttcatg ggactcccct cc                         42

<210> SEQ ID NO 106
<211> LENGTH: 40
<212> TYPE: DNA
<213> ORGANISM: Artificial
<220> FEATURE:
<223> OTHER INFORMATION: Primer

<400> SEQUENCE: 106
ttgtcacatg ctcgcgtgtc tcagacgcta ggcgatacca                            40

<210> SEQ ID NO 107
<211> LENGTH: 46
<212> TYPE: DNA
<213> ORGANISM: Artificial
<220> FEATURE:
<223> OTHER INFORMATION: Primer

<400> SEQUENCE: 107 caggggatc gtcgacgcca ccatgccttc aattaagttg cagagt                       46

<210> SEQ ID NO 108
<211> LENGTH: 42
<212> TYPE: DNA
<213> ORGANISM: Artificial
<220> FEATURE:
<223> OTHER INFORMATION: Primer

<400> SEQUENCE: 108
```

```
ccacttcctc ggggaagtag gtcttctctt cacaccactg gt                    42

<210> SEQ ID NO 109
<211> LENGTH: 42
<212> TYPE: DNA
<213> ORGANISM: Artificial
<220> FEATURE:
<223> OTHER INFORMATION: Primer

<400> SEQUENCE: 109
gggccattgt cacatgctcg cgcttctctt cacaccactg gt                    42

<210> SEQ ID NO 110
<211> LENGTH: 44
<212> TYPE: DNA
<213> ORGANISM: Artificial
<220> FEATURE:
<223> OTHER INFORMATION: Primer

<400> SEQUENCE: 110
ccacttcctc ggggaagtag gtccccttga tcatattggc aaca                  44

<210> SEQ ID NO 111
<211> LENGTH: 44
<212> TYPE: DNA
<213> ORGANISM: Artificial
<220> FEATURE:
<223> OTHER INFORMATION: Primer

<400> SEQUENCE: 111
gggccattgt cacatgctcg cgccccttga tcatattggc aaca                  44

<210> SEQ ID NO 112
<211> LENGTH: 38
<212> TYPE: DNA
<213> ORGANISM: Artificial
<220> FEATURE:
<223> OTHER INFORMATION: Primer

<400> SEQUENCE: 112
actttggccg cggctcgagg ggctccggtg cccgtcag                         38

<210> SEQ ID NO 113
<211> LENGTH: 42
<212> TYPE: DNA
<213> ORGANISM: Artificial
<220> FEATURE:
<223> OTHER INFORMATION: Primer

<400> SEQUENCE: 113
catggtggcg tcgacgatcc cctcacgaca cctgaaatgg aa                    42

<210> SEQ ID NO 114
<211> LENGTH: 32
<212> TYPE: DNA
<213> ORGANISM: Artificial
<220> FEATURE:
<223> OTHER INFORMATION: Primer

<400> SEQUENCE: 114
tgtcagtcta gaatgagtgt gggtcttcct gg                               32

<210> SEQ ID NO 115
<211> LENGTH: 31
<212> TYPE: DNA
<213> ORGANISM: Artificial
```

<220> FEATURE:
<223> OTHER INFORMATION: Primer

<400> SEQUENCE: 115
tgtcagggat cctatttcac ctggtggagt c              31

<210> SEQ ID NO 116
<211> LENGTH: 32
<212> TYPE: DNA
<213> ORGANISM: Artificial
<220> FEATURE:
<223> OTHER INFORMATION: Primer

<400> SEQUENCE: 116
tgtcagttcg aaatgactgc catggaggag tc             32

<210> SEQ ID NO 117
<211> LENGTH: 32
<212> TYPE: DNA
<213> ORGANISM: Artificial
<220> FEATURE:
<223> OTHER INFORMATION: Primer

<400> SEQUENCE: 117
tgtcaggcta gcgtctgagt caggccccac tt             32

<210> SEQ ID NO 118
<211> LENGTH: 31
<212> TYPE: DNA
<213> ORGANISM: Artificial
<220> FEATURE:
<223> OTHER INFORMATION: Primer

<400> SEQUENCE: 118
ggtcagtcta gaatggcagt gcctttttgtg g             31

<210> SEQ ID NO 119
<211> LENGTH: 31
<212> TYPE: DNA
<213> ORGANISM: Artificial
<220> FEATURE:
<223> OTHER INFORMATION: Primer

<400> SEQUENCE: 119
ggtcagggat cctgtaacag gaaaccaaac c              31

<210> SEQ ID NO 120
<211> LENGTH: 37
<212> TYPE: DNA
<213> ORGANISM: Artificial
<220> FEATURE:
<223> OTHER INFORMATION: Primer

<400> SEQUENCE: 120
gaggggtcgg caattgaagc ggtgcctaga gaaggtg       37

<210> SEQ ID NO 121
<211> LENGTH: 37
<212> TYPE: DNA
<213> ORGANISM: Artificial
<220> FEATURE:
<223> OTHER INFORMATION: Primer

<400> SEQUENCE: 121
caccttctct aggcaccgct tcaattgccg acccctc       37

```
<210> SEQ ID NO 122
<211> LENGTH: 64
<212> TYPE: DNA
<213> ORGANISM: Artificial
<220> FEATURE:
<223> OTHER INFORMATION: Primer

<400> SEQUENCE: 122
gtctgagtcg acgccaccat ggactacaaa gacgatgacg acaagaccta cttccccgag    60
gaag                                                                 64

<210> SEQ ID NO 123
<211> LENGTH: 148
<212> TYPE: DNA
<213> ORGANISM: Artificial
<220> FEATURE:
<223> OTHER INFORMATION: Primer

<400> SEQUENCE: 123
gtctgagtcg acgccaccat ggagcagaaa ctcattagcg aggaggacct gaacagcgaa    60
cagaaactca tttccgaaga ggatctcaac tccgagcaga agctgatcag cgaggaggac   120
ctgagatcca cctacttccc cgaggaag                                      148

<210> SEQ ID NO 124
<211> LENGTH: 33
<212> TYPE: DNA
<213> ORGANISM: Artificial
<220> FEATURE:
<223> OTHER INFORMATION: Primer

<400> SEQUENCE: 124
attctagcta gcatgcggcg gcagcatggc cag                                 33

<210> SEQ ID NO 125
<211> LENGTH: 32
<212> TYPE: DNA
<213> ORGANISM: Artificial
<220> FEATURE:
<223> OTHER INFORMATION: Primer

<400> SEQUENCE: 125
ctcggatacg tacttgaagg cctccggaat gc                                  32

<210> SEQ ID NO 126
<211> LENGTH: 33
<212> TYPE: DNA
<213> ORGANISM: Artificial
<220> FEATURE:
<223> OTHER INFORMATION: Primer

<400> SEQUENCE: 126
attctattcg aactgccgcg gcacagcgcg gtc                                 33

<210> SEQ ID NO 127
<211> LENGTH: 32
<212> TYPE: DNA
<213> ORGANISM: Artificial
<220> FEATURE:
<223> OTHER INFORMATION: Primer

<400> SEQUENCE: 127
attaaagcta gcgtgcttcc cggcgcgctt gg                                  32
```

```
<210> SEQ ID NO 128
<211> LENGTH: 29
<212> TYPE: DNA
<213> ORGANISM: Artificial
<220> FEATURE:
<223> OTHER INFORMATION: Primer

<400> SEQUENCE: 128
agcttctaga atggaggagc cgcagtcag                               29

<210> SEQ ID NO 129
<211> LENGTH: 30
<212> TYPE: DNA
<213> ORGANISM: Artificial
<220> FEATURE:
<223> OTHER INFORMATION: Primer

<400> SEQUENCE: 129
agctggatcc gtctgagtca ggcccttctg                              30

<210> SEQ ID NO 130
<211> LENGTH: 58
<212> TYPE: DNA
<213> ORGANISM: Artificial
<220> FEATURE:
<223> OTHER INFORMATION: Primer

<400> SEQUENCE: 130
ccgggccaac ctgtactatg tttaactcga gttaaacata gtacaggttg gcttttg    58

<210> SEQ ID NO 131
<211> LENGTH: 58
<212> TYPE: DNA
<213> ORGANISM: Artificial
<220> FEATURE:
<223> OTHER INFORMATION: Primer

<400> SEQUENCE: 131
aattcaaaaa gccaacctgt actatgttta actcgagtta aacatagtac aggttggc    58

<210> SEQ ID NO 132
<211> LENGTH: 57
<212> TYPE: DNA
<213> ORGANISM: Artificial
<220> FEATURE:
<223> OTHER INFORMATION: Primer

<400> SEQUENCE: 132
ccggcccatg tagtagtatc actttctcga gaaagtgata ctactacatg ggttttt    57

<210> SEQ ID NO 133
<211> LENGTH: 57
<212> TYPE: DNA
<213> ORGANISM: Artificial
<220> FEATURE:
<223> OTHER INFORMATION: Primer

<400> SEQUENCE: 133
aattaaaaac ccatgtagta gtatcacttt ctcgagaaag tgatactact acatggg    57

<210> SEQ ID NO 134
<211> LENGTH: 58
<212> TYPE: DNA
<213> ORGANISM: Artificial
<220> FEATURE:
<223> OTHER INFORMATION: Primer
```

```
<400> SEQUENCE: 134
ccggctttgt tcaggttca gtattctcga gaatactgaa cctgaaacaa agtttttg      58

<210> SEQ ID NO 135
<211> LENGTH: 58
<212> TYPE: DNA
<213> ORGANISM: Artificial
<220> FEATURE:
<223> OTHER INFORMATION: Primer

<400> SEQUENCE: 135
aattcaaaaa ctttgtttca ggttcagtat tctcgagaat actgaacctg aaacaaag    58

<210> SEQ ID NO 136
<211> LENGTH: 54
<212> TYPE: DNA
<213> ORGANISM: Artificial
<220> FEATURE:
<223> OTHER INFORMATION: Primer

<400> SEQUENCE: 136
ccggcttacg ctgagtactt cgactcgagt cgaagtactc agcgtaagtt tttg         54

<210> SEQ ID NO 137
<211> LENGTH: 54
<212> TYPE: DNA
<213> ORGANISM: Artificial
<220> FEATURE:
<223> OTHER INFORMATION: Primer

<400> SEQUENCE: 137
aattcaaaaa cttacgctga gtacttcgac tcgagtcgaa gtactcagcg taag         54

<210> SEQ ID NO 138
<211> LENGTH: 58
<212> TYPE: DNA
<213> ORGANISM: Artificial
<220> FEATURE:
<223> OTHER INFORMATION: Primer

<400> SEQUENCE: 138
ccgggaggga tgtttgggag atgtactcga gtacatctcc caaacatccc tcttttg     58

<210> SEQ ID NO 139
<211> LENGTH: 58
<212> TYPE: DNA
<213> ORGANISM: Artificial
<220> FEATURE:
<223> OTHER INFORMATION: Primer

<400> SEQUENCE: 139
aattcaaaaa gagggatgtt tgggagatgt actcgagtac atctcccaaa catccctc   58
```